(12) United States Patent
Willems et al.

(10) Patent No.: US 8,258,175 B2
(45) Date of Patent: Sep. 4, 2012

(54) ISOINDOLIN-1-ONE DERIVATIVES

(75) Inventors: Hendrika Maria Gerarda Willems, Histon (GB); Per Kallblad, Stockholm (SE); Ian Robert Hardcastle, Tyne (GB); Roger John Griffin, Tyne (GB); Bernard Thomas Golding, Tyne (GB); John Lunec, Tyne (GB); Martin E. M. Noble, Oxford (GB); David R. Newell, Tyne (GB); Alan H. Calvert, Tyne (GB)

(73) Assignee: Cancer Research Technology Limited, London (GB)

( * ) Notice: Subject to any disclaimer, the term of this patent is extended or adjusted under 35 U.S.C. 154(b) by 618 days.

(21) Appl. No.: 11/574,531

(22) PCT Filed: Aug. 26, 2005

(86) PCT No.: PCT/GB2005/003345
§ 371 (c)(1),
(2), (4) Date: Jul. 1, 2008

(87) PCT Pub. No.: WO2006/024837
PCT Pub. Date: Mar. 9, 2006

(65) Prior Publication Data
US 2008/0261917 A1 Oct. 23, 2008

(30) Foreign Application Priority Data
Sep. 2, 2004 (GB) .................................... 0419481.7

(51) Int. Cl.
*A61K 31/4015* (2006.01)
*C07D 209/46* (2006.01)

(52) U.S. Cl. ........................................ 514/416; 548/485
(58) Field of Classification Search .................... 548/485
See application file for complete search history.

(56) References Cited

U.S. PATENT DOCUMENTS

| 3,466,298 A | | 9/1969 | Sulkowski | |
|---|---|---|---|---|
| 4,244,966 A | * | 1/1981 | Lippman et al. | 514/416 |
| 4,331,600 A | * | 5/1982 | Golec et al. | 548/472 |

FOREIGN PATENT DOCUMENTS

| JP | 2004-217591 | 8/2004 |
|---|---|---|
| JP | 2005-255660 | 9/2005 |

OTHER PUBLICATIONS

Document No. 55:60933 retrieved from CAPLUS on Jan. 29, 2010.*
Prodrug [online], [retrieved on Mar. 11, 2007]. Retrieved from the Internet, URL;http://en.wikipedia.org/wiki/Prodrug.*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Document 95:150329 retrieved from CAPLUS on May 21, 2010.*
Document 93:220149 retrieved from CAPLUS on May 21, 2010.*
Bioorganic & Medicinal Chemistry 8 (2000) 2629-2641.*
Tetrahedron 56 (2000) 4837-4844.*
Schon, Oliver et al., Molecular Mechanism of the Interaction between MDM2 and p53; JMB; J. Mol. Viol., (2002) 323, 491-501.
Chene, Patrick et al.; A Small Synthetic Peptide, which Inhibits the p53-hdm2 Interaction, . . . ; JMB; J. Mol. Biol. (2000) 299, 245-253.
Ghosh, Mithua et al.; Overexpression of Mdm2 and MdmX Fusion Proteins Alters p53 Mediated Transactivation, . . . ; American Chemical Society; Biochemistry 2003, 42, 2291-2299.
Lane, D.P.; p53, guardian of the genome; Nature Publishing Group; vol. 358, Jul. 2, 1992.
Levine, Arnold J.; p53, the Cellular Gatekeeper for Growth and Division; Princeton University Review; Cell Press; vol. 88, 323-331; Feb. 7, 1997.
Oliner, J.D. et al.; Amplification of a gene encoding a p53-associated protein in human sarcomas; Nature Publishing Group; vol. 358; Jul. 2, 1992.
Toledo, Franck et ano; Regulating the p53 pathway: in vitro hypotheses, in vivo veritas; Nature Publishing Group; vol. 6, pp. 909-923; Dec. 2006.
Vassilev, Lyubomir T. et al.; in Vivo Activation of the p53 Pathway by Small-Molecule Antagonists of MDM2; Science Magazine; vol. 303, pp. 844-848; Feb. 6, 2004.

(Continued)

*Primary Examiner* — Shawquia Young
(74) *Attorney, Agent, or Firm* — Notaro, Michalos & Zaccaria P.C.

(57) ABSTRACT

A compound of formula

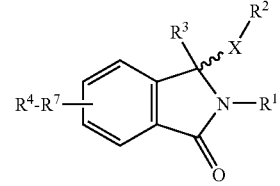

or a prodrug and/or a pharmaceutically acceptable salt thereof, wherein X is O, N or S; $R^1$ is hydrogen, halo, hydroxy, substituted or unsubstituted alkyl, substituted or unsubstituted hydroxyalkyl, substituted or unsubstituted alkylamine, alkoxy, substituted or unsubstituted aryl or heteroaryl, and substituted or unsubstituted aralkyl or heteroaralkyl; $R^2$ is hydrogen, halo, hydroxy, substituted or unsubstituted alkyl, substituted or unsubstituted hydroxyalkyl substituted or unsubstituted alkylamine, alkoxy, substituted or unsubstituted aryl or heteroaryl, and substituted or unsubstituted aralkyl or heteroalkyl; $R^3$ is hydrogen, halo, hydroxy, substituted or unsubstituted alloy substituted or unsubstituted hydroxyalkyl, substituted or unsubstituted alkylamine alkoxy, substituted or unsubstituted aryl or heteroaryl, and substituted or unsubstituted aralkyl or heteroalkyl; and $R^4$-$R^7$, is used to represent groups $R^4$, $R^5$, $R^6$ and $R^7$ which are H, OH, alkyl, alkoxy, alkylamine, hydroxyalkyl, halo, $CF_3$, $NH_2$, $NO_2$, COOH, C=O.

9 Claims, 1 Drawing Sheet

OTHER PUBLICATIONS

Donehower, Lawrence A. et al.; Mice deficient for p53 are developmentally normal . . . ; Nature Publishing Group; vol. 356, pp. 215-221; Mar. 19, 1992.

Makoto Inaba, Reversal of Resistance to Vincristine in P388 Leukemia by Various Polycycllic Clinical Drugs, with a Special Emphasis on Quinacrine, cancerres.aacrjournals.org, 1998.

Joon Seok Park, Noble 2-[3-(Cyclopentyloxy)-4-Methoxyphenyl]-1-Isoindolinone Derivatives. Part 1 . . . , Arch Pharm Res vol. 24, No. 5, 367-370, 2001.

Martin Croisy-Delcey, Diphenyl Quinolines and Isoquinolines: Synthesis and Primary Biological Evaluation, Bioorganic & Medicinal Chemistry 8 (2000) 2629-2641.

Jonathan Griffiths, Model Studies for Damage to Nucleic Acids Mediated by Thiyl Radicals, Tetrahadron, vol. 48, No. 26, pp. 5543-5556, 1992.

Price Truit, 3-Phenylphthalirniclines, New Compounds, J. Med Chem Sep. 1965.

Klrill V. Nikitin, Synthesis of 5-alkyl-and 5-aryl-1, 5-dihydro-2H-pyrrol-2-ones via coupling of 5 chloro-1, 5-dihdro-2H . . . , Canadian Journal of Chem. 78: 1285-1288, 2000.

Martin S. Kitching, Synthesis of 3-Alkoxy-and 3-Alkylarnino-2-alkyl-3-arylisoindolinones, Synlett, 997-999, 1999.

H.D. Bartfeld, 3-Oxo-Isoindole, Tetrahedron Letters No. 10, 757-760, 1970.

Rainer Liebl, Notiz zur Synthese von 3-[Alkyl(aryl)thiio]isoindolinonen aus 2-Formylbenzoesaure-methylester, Liebigs Ann. Chem, 1093-1094-1985.

V.A. Usov, Cyclic B-Aminovinylimines, Khimiya Geterotskilicheskikh Soedinenii, vol, 5, No. 4, 640-644, 1969.

K. Kormendy. Uber Reaktionen in Polyaminsynthesen, Mit, Phthaliminoalkylhaloiden, I. Acta Chimica, Apr. 1958.

Munir Ahmed, et al, Preparation of Some Isoindolo [2,1-f] phenanthridine Derivatives, J.Amer. Chem. Soc., 1936, 58, 1325.

* cited by examiner

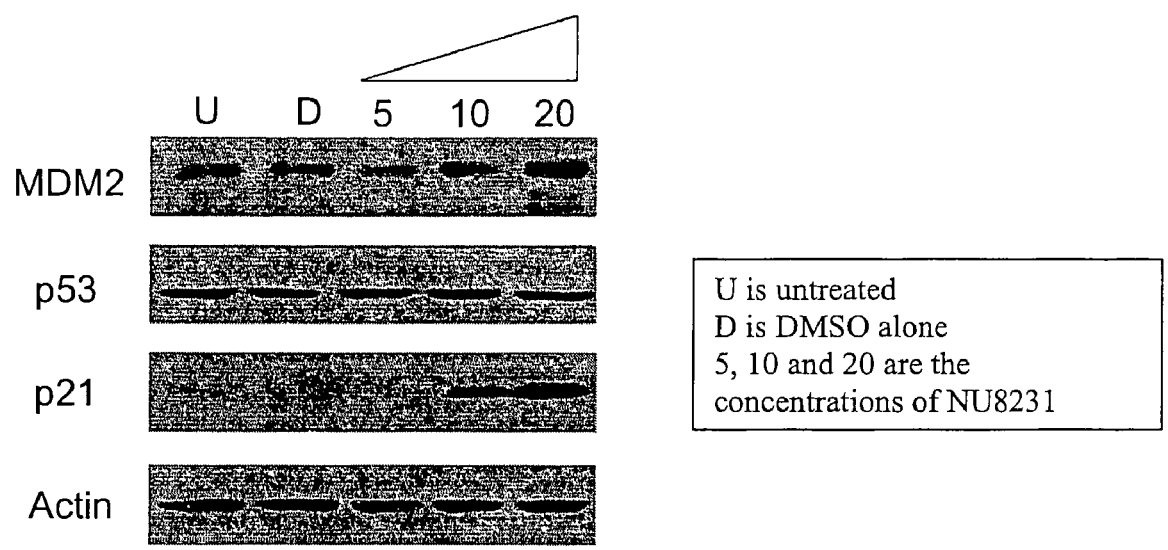

ISOINDOLIN-1-ONE DERIVATIVES

The present invention relates to a series of isoindolin-1-one derivatives which find particular utility in the treatment of cancer.

Under conditions of stress such as hypoxia and DNA damage it is known the cellular level of the protein p53 increases. P53 is known to initiate transcription of a number of genes which govern progression through the cell cycle, the initiation of DNA repair and programmed cell death[1,2]. Thus, p53 is a tumour suppressor.

The activity of p53 is tightly regulated by the MDM2 protein, the transcription of which is itself regulated by p53. P53 is inactivated when it becomes bound to the p53 transactivation domain of the MDM2 protein. Once inactivated the activities of p53 are repressed and the p53-MDM2 complex becomes a target for ubiquitylation.

In normal cells the balance between active p53 and inactive MDM2-bound p53 is maintained in an autoregulatory negative feed back loop[3,4]. That is to say that p53 can activate MDM2 expression, which in turn leads to the repression of p53.

It has been found that inactivation of p53 by mutation is common in around half of all tumours. Furthermore, in around 7% of tumours, over expression of MDM2 results in the loss of functional p53, thereby allowing malignant transformation and uncontrolled tumour growth[5].

X-ray crystal studies of the MDM2-p53 complex have been conducted and have revealed a hydrophobic pocket on the surface of MDM2 into which the side chains of Phe 19, Trp 23 and Leu 26 on p53 bind[6]. Therefore, inhibition of the MDM2-p53 binding interaction is an attractive target for researchers developing treatments for cancer as a means of restoring normal p53 activity in cells overexpressing MDM2 and thereby exerting an anti-tumour effect[7].

A number of inhibitors of the MDM2-p53 interaction have been discovered including peptide inhibitors, the natural product chlorofusion, and small molecules such as the imidazolines described in WO 03/051359[8-11].

The present invention describes a novel series of compounds which inhibit the MDM2-p53 interaction and which have exciting in vitro activity.

According to a first aspect of the present invention there is provided a compound of formula I

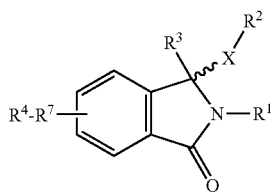

I or a prodrug and/or pharmaceutically acceptable salt thereof, wherein

X is selected from O, N or S;

$R^1$ is selected from hydrogen, halo, hydroxy, substituted or unsubstituted alkyl, substituted or unsubstituted hydroxyalkyl, substituted or unsubstituted alkylamine, alkoxy, substituted or unsubstituted aryl or heteroaryl, and substituted or unsubstituted aralkyl or heteroalkyl;

$R^2$ is selected from hydrogen, halo, hydroxy, substituted or unsubstituted alkyl, substituted or unsubstituted hydroxyalkyl substituted or unsubstituted alkylamine, alkoxy, substituted or unsubstituted aryl or heteroaryl, and substituted or unsubstituted aralkyl or heteroalkyl;

$R^3$ is selected from hydrogen, halo, hydroxy, substituted or unsubstituted alloy substituted or unsubstituted hydroxyalkyl, substituted or unsubstituted alkylamine alkoxy, substituted or unsubstituted aryl or heteroaryl, and substituted or unsubstituted aralkyl or heteroalkyl; and $R^4$-$R^7$, is used to represent groups $R^4$, $R^5$, $R^6$ and $R^7$ which are independently selected from H, OH, alkyl, alkoxy, alkylamine, hydroxyalkyl, halo, $CF_3$, $NH_2$, $NO_2$, COOH, C=O.

Advantageously, the compounds of the present invention have been shown to be good inhibitors of the formation of the MDM2-p53 complex.

The term "halo" is used herein to denote a halogen atom which is selected from fluorine, chlorine, bromine or iodine.

The term "alkyl" is used herein to denote a lower alkyl group i.e a cyclic, branched or straight chain hydrocarbon having one to eight carbon atoms.

The term "aryl" is used herein to denote a carbocyclic group or structure having at least one aromatic ring. The said ring may form part of a multiple condensed ring structure, for example phenyl, naphthalene, anthracene.

The term "aralkyl" is used herein to denote an alkyl, as hereinbefore defined, in which there is an aryl group, as hereinbefore defined, for example benzyl.

The term "heteroaryl" is used herein the denote an aryl group, as hereinbefore defined in which said group comprises at least one heteroatom, selected from, for example N, O or S, in said at least one aromatic ring. Suitable examples include, but are not limited to pyrindine, pyrrole, furan, thiophene and imidazole.

The term "heteroaralkyl" is used herein to denote an aralkyl substituents, as hereinbefore defined, in which said at least one aromatic ring comprises at least one heteroatom selected from, for example N, O or S. Suitable examples include, but are not limited to methyl pyrindine and methylfuran.

The term "substituted alkyl" is used herein to denote an alkyl substituents, as hereinbefore defined, which is substituted with one or more functional groups. Suitable examples include, but are not limited to, propanoic acid, butanal and butanone, phenyl amino ethane and ethane sulfonic acid.

The term "substituted aryl" is used herein to denote an aryl substituent, as hereinbefore defined, which is substituted with one or more functional groups. Suitable examples include, but are not limited to, benzoic acid and nitrobenzene.

The term "substituted heteroaryl" is used herein to denote a heteroaryl substituent, as hereinbefore defined, which is substituted with one or more functional groups.

The term "substituted aralkyl" is used herein to denote an aralkyl substituents, as hereinbefore defined, which is substituted with one or more functional groups.

The term "substituted heteroaralkyl" is used herein to denote a heteroaralkyl substituent, as hereinbefore defined, which is substituted with one or more functional groups.

The term "alkoxy" is used herein to denote an alkyl group, as hereinbefore defined, which is linked to a second chemical structure, which may be any of the foregoing, by way of an oxygen atom. The carbon chain of the alkyl group may be substituted with one or more functional groups to provide a "substituted alkoxy". Suitable examples include, but are not limited to, ethoxy, methoxy and propoxy.

The term "alkylamine" is used herein to denote an alkyl group, as hereinbefore defined, comprising at least one amine function. The carbon chain of the alkyl group may be substituted with one or more functional groups. The amine function may be primary, secondary or tertiary. Suitable examples include, but are not limited to, ethyl amine and diethyl amine. The amine function may form part of a cyclic or heroaromatic structure or another functionality for example amide.

As referred to herein suitable functional groups include, but are not limited to, any of the following which may be used alone or in combination: hydroxyl, hydroxyalkyl, acyl, acetamide, carboxyl, cyano, carboxamide (carbamoyl), sulfonamide, sulfone, sulfoxide, amino, alkoxy or silico ligand.

Compounds of particular interest are those in which $R^1$ is a substituted or unsubstituted alkyl group or a substituted or unsubstituted aryl group; $R^2$ is hydroxyalkyl, a substituted or unsubstituted heteroaralkyl group; $R^3$ is substituted or unsubstituted aryl group; and $R^4$, $R^5$ and $R^6$ are hydrogen atoms.

Preferably, $R^1$ is an alkyl group comprising 1 to 4 carbon atoms, a phenyl group or an alkyl group substituted with an acetamide functional group.

Preferably, $R^2$ is an aryl group having one or more functional groups, said functional groups being independently selected from alkoxy, hydroxyl and alkyl, hydroxyalkyl, or a heteroaralkyl group.

Most preferably, the alkoxy group is methoxy, the alkyl group is $^t$butyl, the hydroxyalkyl group is ethyl alcohol, and the heteroaralkyl group comprises a pyridine moiety.

Preferably, $R^3$ is a substituted or unsubstituted aryl group. Most preferably $R^3$ is selected from phenyl, 4-chlorophenyl or silylethoxymethoxyphenyl.

It will be understood that where reference is made in this specification to compounds of formula I such reference should be construed as extending also to their pharmaceutically acceptable salts and to other pharmaceutically acceptable bio precursors (prodrug forms) where relevant. The term "prodrug" is used in the present specification to denote modified forms or derivatives of a pharmacologically active compound which biodegrade or are modified in vivo so as to become converted into said active compound after administration, especially intravenous administration, in the course of therapeutic treatment of a mammal. Such prodrugs are commonly chosen because of an enhanced solubility of aqueous media which helps to overcome formulation problems, and also in some cases to give a relatively slow or controlled release of the active agent.

It should also be understood that where any of the compounds referred to can exist in more than one enantiomeric and/or diastereomeric form, all such forms, mixtures thereof, and their preparation and uses are within the scope of the invention. It should be noted, however, that stereo chemical considerations are likely to be important and there may be considerable selectivity such that different enantiomers or diastereoisomers have significantly different inhibitory activity.

In some compounds, one or more of $R^4$ to $R^7$ is H with two of the remaining R groups linked so as to form a 5 to 7 membered ring structure. The ring structure is preferably saturated and may comprise at least one heteroatom selected from N, O or S.

Examples of compounds which are at present of especial interest or preferred for use in carrying out the invention comprise the following:

| Number | Compound Descriptions | Structure | ELISA IC$_{50}$ (μM) |
|---|---|---|---|
| NU8033 | 3-(3-hydoxy-propoxy)-3-phenyl-2-propyl-2,3-dihydro-1H-isoindolin-1-one | 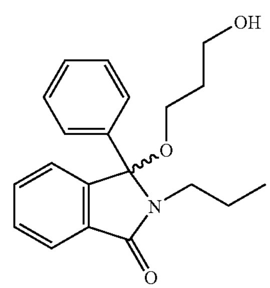 | >500 μM |
| NU8034 | 2-benzyl-3-(3-hydroxy-propoxy)-3-phenyl-2,3-dihydro-1H-isoindolin-1-one | 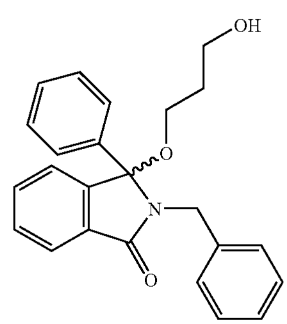 | 245 ± 11 |

-continued

| Number | Compound Descriptions | Structure | ELISA IC$_{50}$ ($\mu$M) |
|---|---|---|---|
| NU8104 | 4-$^t$butyl-N-[(2-propyl-3-oxo-1-(4-silylethoxymethoxyphenyl)-2,3-dihydro-1H-isoindolin-1-yl)oxy]benzamide | 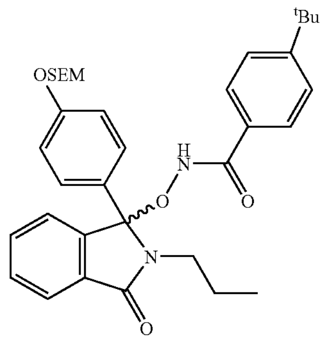 | 27 |
| NU8113 | 2-benzyl-3-(4-$^t$butylbenzyloxy)-3-phenyl-2,3-dihydro-isoindolin-1-one | 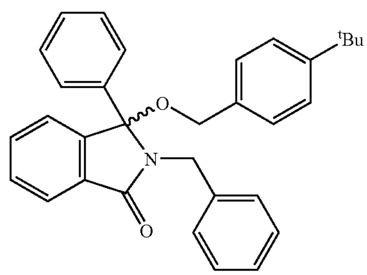 | 92 ± 11 |
| NU8133 | 2-benzyl-3-phenyl-3-(2-pyridin-2-yl-ethoxy]-2,3-dihydro-isoindolin-1-one | 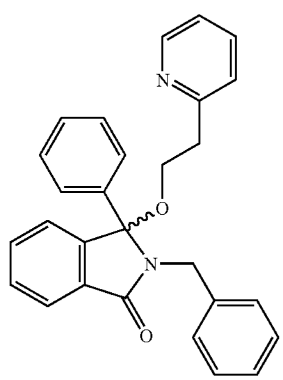 | 206 ± 130 |
| NU8170 | 2-benzyl-3-(4-chlorophenyl)-3-(2-pyridin-2-yl-ethoxy)-2,3-dihydroisoindolin-1-one | 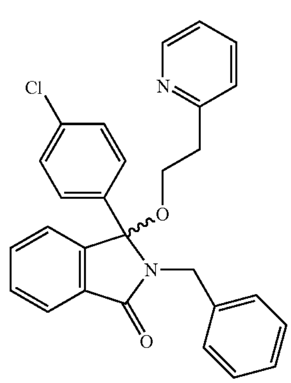 | 26.2 ± 4.2 |

-continued

| Number | Compound Descriptions | Structure | ELISA IC$_{50}$ (μM) |
|---|---|---|---|
| NU8200 | N-[2-Cyclohexylmethyl-1-(4-isobutoxy-phenyl)-3-oxo-2,3-dihydro-1H-isoindolin-1-yl]-benzamide<br>496.64<br>C$_{32}$H$_{36}$N$_2$O$_3$ | 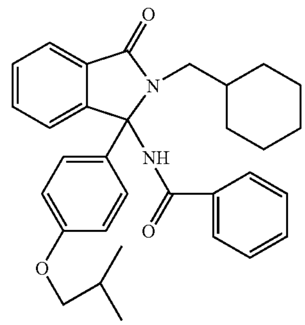 | 123 ± 30 |
| NU8201 | N-[2-cyclohexylmethyl 1-(4-ethoxy-phenyl)-3-oxo-2,3-dihydro-1H-isoindolin-1-yl]-benzamide<br>468.59<br>C$_{30}$H$_{32}$N$_2$O$_3$ | 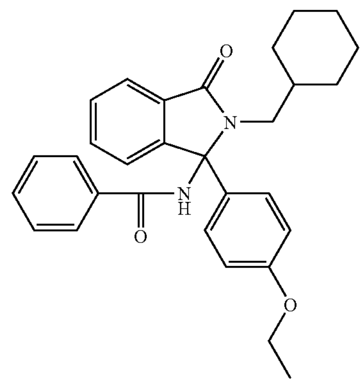 | 209 ± 28 |
| NU8202 | N-[2-cylohexylmethyl-1-(4-methylsulfanyl-phenyl)-3-oxo-2,3-dihydro-1H-isoindolin-1-yl]-benzamide<br>470.63<br>C$_{29}$H$_{30}$N$_2$O$_2$S | 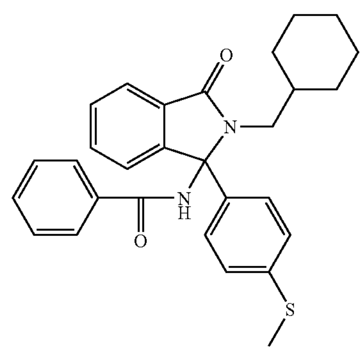 | 82 ± 16 |
| NU8203 | N-[2-(2-Benzyl-3-oxo-1-phenyl-2,3-dihydro-1H-isoindolin-1-yloxy)-ethyl]-2,4-dihydroxy-benzamide<br>494.54<br>C$_{30}$H$_{26}$N$_2$O$_5$ | 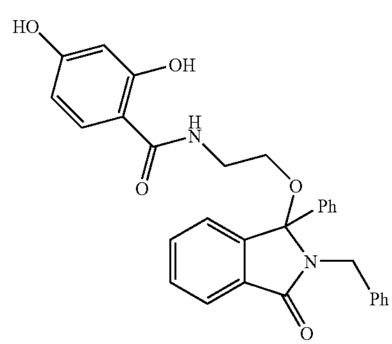 | 96 ± 30 |

-continued

| Number | Compound Descriptions | Structure | ELISA IC$_{50}$ ($\mu$M) |
|---|---|---|---|
| NU8204 | 2-Benzyl-3-phenyl-3-(2-phenylamino-ethoxy)-2,3-dihydro-isoindolin-1-one<br>434.53<br>C$_{29}$H$_{26}$N$_2$O$_2$ | 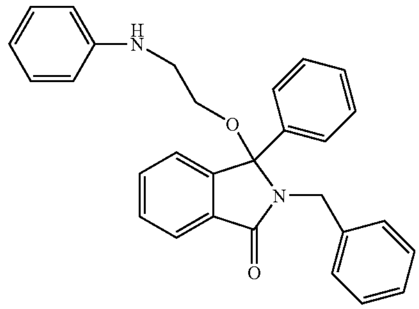 | 116 ± 20 |
| NU8205 | 2-Benzyl-3-(4-hydroxy-3,5-dimethoxy-benzyloxy)-3-phenyl-2,3-dihydro-isoindolin-1-one<br>481.54<br>C$_{30}$H$_{27}$NO$_5$ | 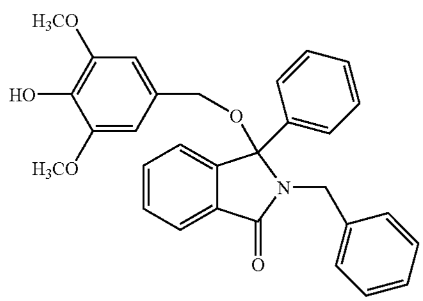 | 17.9 ± 0.3 |
| NU8206 | 2-(2-Hydroxy-ethyl)-3-phenyl-3-propoxy-2,3-dihydro-isoindolin-1-one<br>311.37<br>C$_{19}$H$_{21}$NO$_3$ | 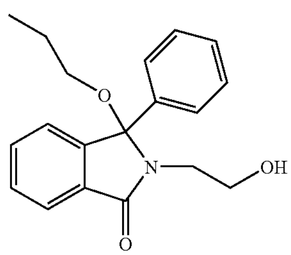 | >500 |
| NU8207 | 5-(2-Benzyl-3-oxo-1-phenyl-2,3-dihydro-1H-isoindolin-1-yloxymethyl)-furan-2-carbaldehyde<br>423.26<br>C$_{27}$H$_{21}$NO$_4$ | 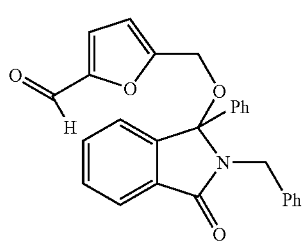 | 97 ± 30 |
| NU8208 | 2-Benzyl-3-(3-hydroxy-benzyloxy)-3-phenyl-2,3-dihydro-isoindolin-1-one<br>421.29<br>C$_{28}$H$_{23}$NO$_3$ | 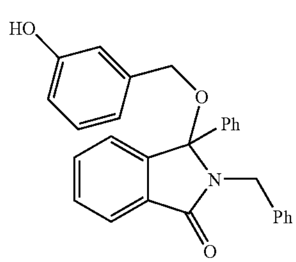 | 58 ± 14 |

| Number | Compound Descriptions | Structure | ELISA IC$_{50}$ ($\mu$M) |
|---|---|---|---|
| NU8209 | 3-(4-Methyl-3,5-dinitro-benzyloxy)-2-propyl-3-[4-(2-trimethylsilanyl-ethoxymethoxy)-phenyl]-2,3-dihydro-isoindolin-1-one<br>607.73<br>C$_{31}$H$_{37}$N$_3$O$_8$Si | 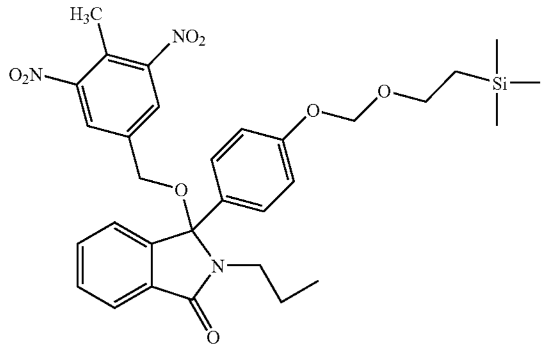 | 103 ± 44 |
| NU8210 | Sodium; 2-(2-benzyl-3-oxo-1-phenyl-2,3-dihydro-1H-isoindolin-1-yloxy)-ethanesulfonate<br>445.46<br>C$_{23}$H$_{20}$NNaO$_5$S | 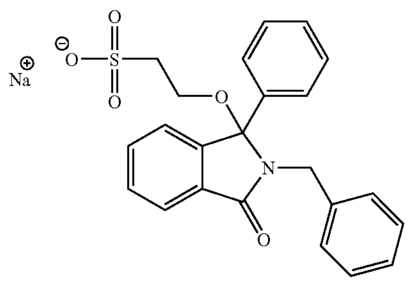 | 345 ± 55 |
| NU8211 | 2-Benzyl-3-phenyl-3-(2-piperazin-1-yl-ethoxy)-2,3-dihydro-isoindolin-1-one<br>427.54<br>C$_{27}$H$_{29}$N$_3$O$_2$ | 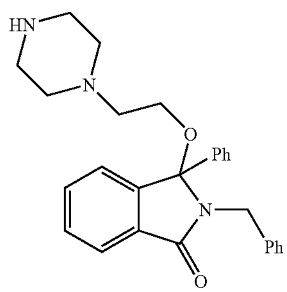 | 315 ± 72 |
| NU8212 | 2-Benzyl-3-(2-butyl-3H-imidazol-4-ylmethoxy)-3-phenyl-2,3-dihydro-isoindolin-1-one<br>451.23<br>C$_{29}$H$_{29}$N$_3$O$_2$ | 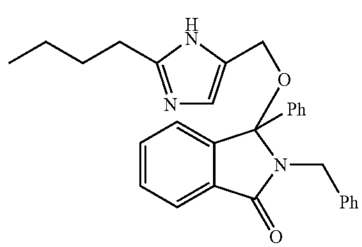 | 78 ± 16 |
| NU8213 | N-{2-[1-(4-tert-Butyl-benzyloxy)-3-oxo-1-phenyl-1,3-dihydro-isoindolin-2-yl]-ethyl}-acetamide<br>456.58<br>C$_{29}$H$_{32}$N$_2$O$_3$ | 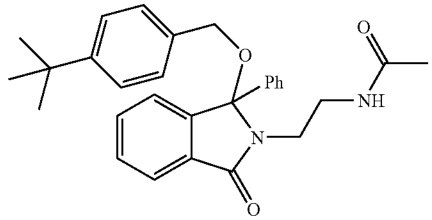 | 14.4 ± 0.3 |

-continued

| Number | Compound Descriptions | Structure | ELISA IC$_{50}$ ($\mu$M) |
|---|---|---|---|
| NU8214 | 3-(4-tert-Butyl-benzyloxy)-2-[2-(3H-imidazol-4-yl)-ethyl]-3-phenyl-2,3-dihydro-isoindolin-1-one<br>465.24<br>C$_{30}$H$_{31}$N$_2$O$_3$ | 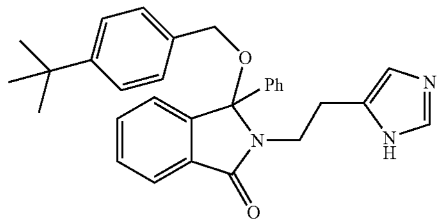 | 214 ± 56 |
| NU8215 | 2-Benzyl-3-(4-hydroxy-benzyloxy)-3-phenyl-2,3-dihydro-isoindolin-1-one<br>421.29<br>C$_{28}$H$_{23}$NO$_3$ | 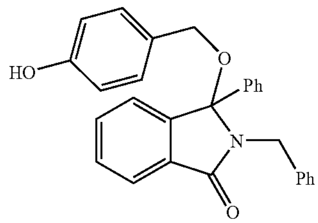 | 79 ± 11 |
| NU8216 | 2-Methyl-acrylic acid 2-[1-(2-hydroxy-1-hydroxymethyl-2-phenyl-ethylamino)-3-oxo-1-phenyl-1,3-dihydro-isoindolin-2-yl]-ethyl ester<br>486.56<br>C$_{29}$H$_{30}$N$_2$O$_5$ | 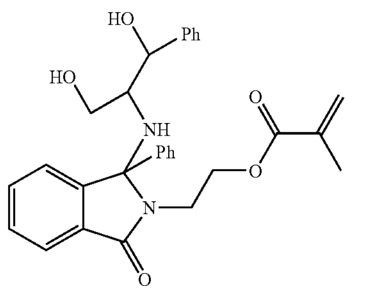 | 103 ± 43 |
| NU8217 | 2-(4,4-Dimethoxy-butyl)-3-phenyl-3-propoxy-2,3-dihydro-isoindolin-1-one<br>383.48<br>C$_{23}$H$_{29}$NO$_4$ | 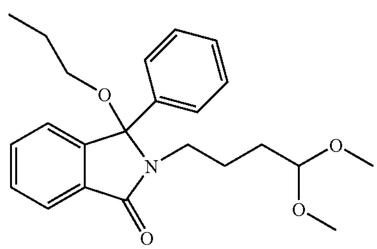 | 70 ± 6 |
| NU8218 | 3-[2-Hydroxy-2-(4-methoxyphenyl)-ethoxy]-2-(3-hydroxypropyl)-3-phenyl-2,3-dihydroisoindolin-1-one<br>433.50<br>C$_{26}$H$_{27}$NO$_5$ | 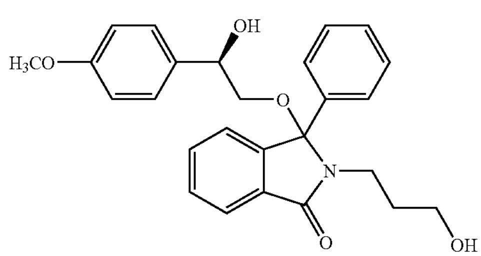 | 326 ± 64 |
| NU8219 | 2-Furan-2-ylmethyl-3-[2-hydroxy-2-(4-methoxyphenyl)-ethoxy]-3-phenyl-2,3-dihydroisoindolin-1-one<br>455.50<br>C$_{28}$H$_{25}$NO$_5$ | 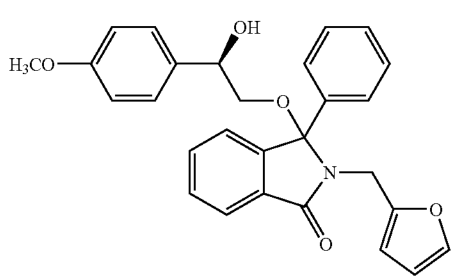 | 181 ± 46 |

-continued

| Number | Compound Descriptions | Structure | ELISA IC$_{50}$ ($\mu$M) |
|---|---|---|---|
| NU8220 | 2-Benzyl-3-(4-tert-butylbenzyloxy)-3-(4-chlorophenyl)-2,3-dihydroisoindolin-1-one<br>496.04<br>C$_{32}$H$_{30}$ClNO$_2$ | 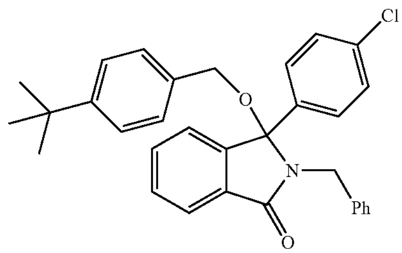 | 99 ± 18 |
| NU8221 | 3-(4-tert-Butylbenzyloxy)-3-(4-chlorophenyl)-2-propyl-2,3-dihydroisoindolin-1-one<br>448.00<br>C$_{28}$H$_{30}$ClNO$_2$ | 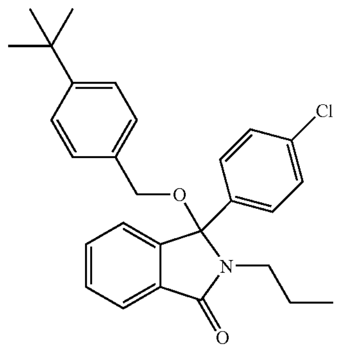 | 187 ± 38 |
| NU8222 | 3-(4-Chlorophenyl)-3-(3-hydroxypropoxy)-2-propyl-2,3-dihydroisoindolin-1-one<br>359.85<br>C$_{20}$H$_{22}$ClNO$_3$ | 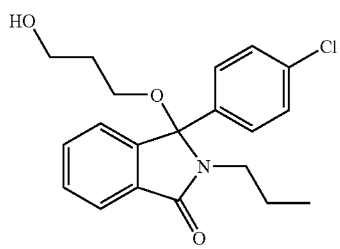 | 16.4 ± 1.6 |
| NU8223 | 3-(4-tert-Butylbenzyloxy)-3-phenyl-2-propyl-2,3-dihydroisoindolin-1-one<br>413.55<br>C$_{28}$H$_{31}$NO$_2$ | 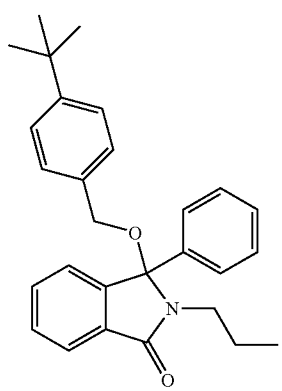 | >500 |
| NU8224 | 3-Phenyl-2-propyl-3-(2-pyridin-2-yl-ethoxy)-2,3-dihydroisoindolin-1-one<br>372.46<br>C$_{24}$H$_{24}$N$_2$O$_2$ | 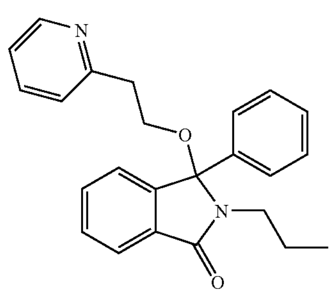 | 100 ± 14 |

-continued

| Number | Compound Descriptions | Structure | ELISA IC$_{50}$ ($\mu$M) |
|---|---|---|---|
| NU8225 | 3-(4-Hydroxy-3,5-dimethoxybenzyloxy)-3-phenyl-2-propyl-2,3-dihydroisoindolin-1-one<br>433.50<br>C$_{26}$H$_{27}$NO$_5$ | 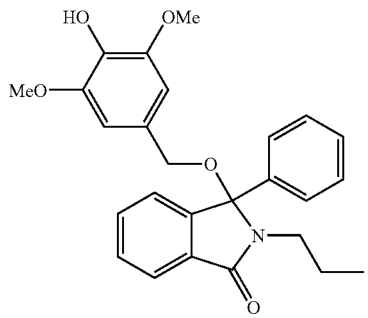 | 82 ± 8 |
| NU8226 | 2-Benzyl-3-(4-methoxybenzyloxy)-3-phenyl-2,3-dihydroisoindolin-1-one<br>435.51<br>C$_{29}$H$_{25}$NO$_3$ | 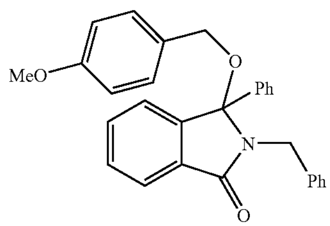 | 456 ± 44 |
| NU8227 | N-{2-[1-(4-Chlorophenyl)-1-(4-hydroxy-3,5-dimethoxybenzyloxy)-3-oxo-1,3-dihydro-isoindolin-2-yl]-ethyl}acetamide<br>510.97<br>C$_{27}$H$_{27}$ClN$_2$O$_6$ | 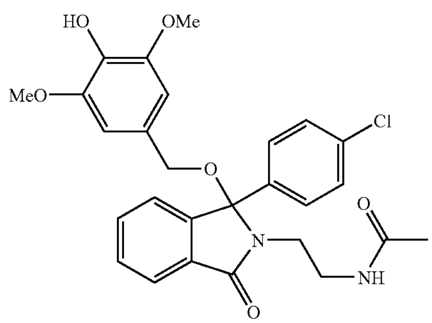 | 76 ± 4 |
| NU8228 | N-{2-[1-(4-tert-Butyl-benzyloxy)-1-(4-chlorophenyl)-3-oxo-1,3-dihydro-isoindolin-2-yl]-ethyl}-acetamide<br>491.02<br>C$_{23}$H$_{31}$ClN$_2$O$_3$ | 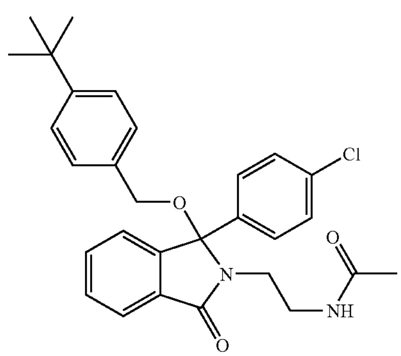 | 91.4 ± 0.4 |
| NU8229 | 3-(4-Chloro-phenyl)-2-propyl-3-(2-pyridin-2-yl-ethoxy)-2,3-dihydro-isoindolin-1-one<br>406.90<br>C$_{24}$H$_{23}$ClN$_2$O$_2$ | 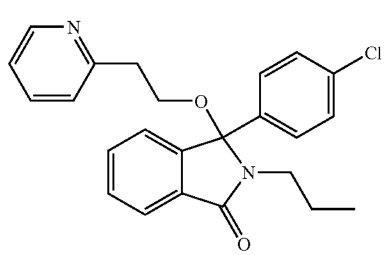 | 56.8 ± 5.5 |

-continued

| Number | Compound Descriptions | Structure | ELISA IC$_{50}$ ($\mu$M) |
|---|---|---|---|
| NU8230 | 2-Benzyl-3-(4-chloro-phenyl)-3-(4-hydroxy-3,5-dimethoxy-benzyloxy)-2,3-dihydro-isoindolin-1-one<br>515.98<br>C$_{30}$H$_{26}$ClNO$_5$ | 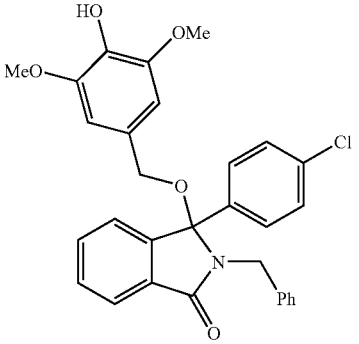 | 41.6 ± 7.8 |
| NU8232 | 3-(4-Allyloxy-3,5-dimethoxybenzyloxy)-3-(4-chlorophenyl)-2-propyl-2,3-dihydroisoindolin-1-one<br>508.00<br>C$_{29}$H$_{30}$ClNO$_5$ | 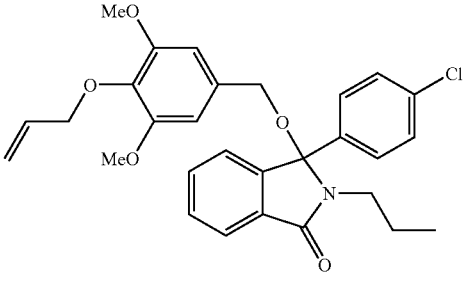 | 264 ± 38 |
| NU8233 | 3-(4-tert-Butylbenzyloxy)-2-propyl-3-[4-(2-trimethylsilanylethoxymethoxy)-phenyl]-2,3-dihydroisoindolin-1-one<br>559.81<br>C$_{34}$H$_{45}$NO$_4$Si | 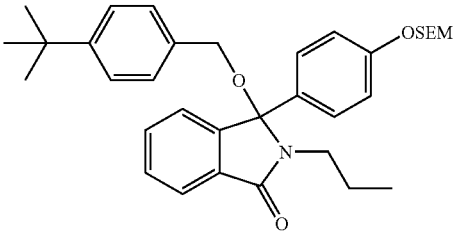 | 464 ± 31 |
| NU8234 | 3-(3-Hydroxy-propoxy)-2-propyl-3-[4-(2-trimethylsilanyl-ethoxymethoxy)-phenyl]-2,3-dihydro-isoindolin-1-one<br>471.66<br>C$_{26}$H$_{37}$NO$_5$Si | 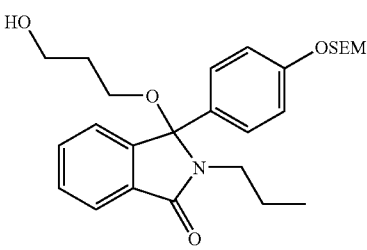 | 476 ± 24 |
| NU8235 | 2-Propyl-3-(2-pyridin-2-yl-ethoxy)-3-[4-(2-trimethylsilanyl-ethoxymethoxy)-phenyl]-2,3-dihydro-isoindolin-1-one<br>518.2<br>C$_{30}$H$_{38}$N$_2$O$_4$Si | 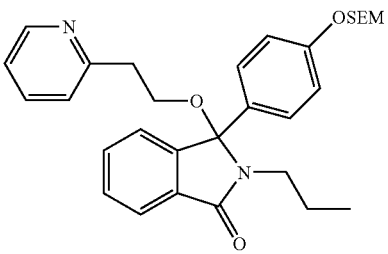 | 312 ± 22 |

-continued

| Number | Compound Descriptions | Structure | ELISA IC$_{50}$ ($\mu$M) |
|---|---|---|---|
| NU8236 | 3-(4-Hydroxy-3,5-dimethoxybenzyloxy)-2-propyl-3-[4-(2-trimethylsilanylethoxymethoxy)phenyl]-2,3-dihydroisoindolin-1-one<br>579.76<br>C$_{32}$H$_{31}$NO$_7$Si | 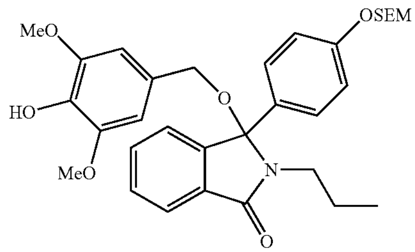 | 118 ± 24 |
| NU8237 | 3-Benzyloxy-3-(4-chlorophenyl)-2-propyl-2,3-dihydroisoindolin-1-one<br>391.89<br>C$_{24}$H$_{22}$ClNO$_2$ | 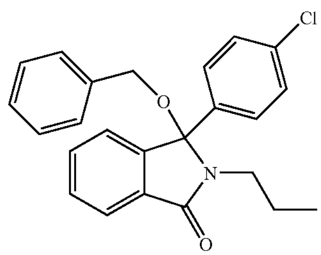 | 409 ± 43 |
| NU8238 | 2-Benzyl-3-(4-hydroxy-3,5-dimethoxybenzyloxy)-3-[4-(2-trimethylsilanylethoxymethoxy)phenyl]-2,3-dihydroisoindolin-1-one<br>627.80<br>C$_{36}$H$_{41}$NO$_7$Si | 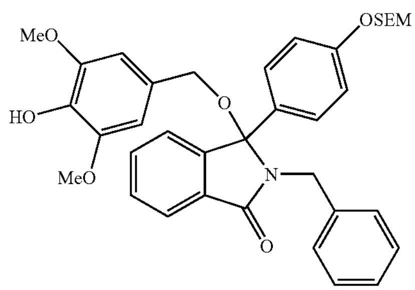 | 257 ± 34 |
| NU8239 | 2-Benzyl-3-hydroxy-3-[4-(2-trimethylsilanylethoxymethoxy)phenyl]-2,3-dihydroisoindolin-1-one<br>461.62<br>C$_{27}$H$_{31}$NO$_4$Si | 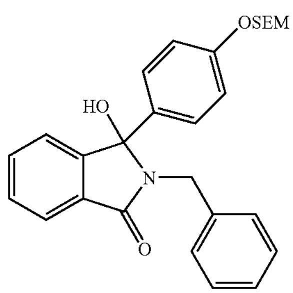 | 366 ± 61 |
| NU8240 | 3-(4-chlorophenyl)-3-(4-allyloxybenzyl)-2-propyl-dihydroisoindolin-1-one<br>447.95<br>C$_{27}$H$_{26}$ClNO$_3$ | 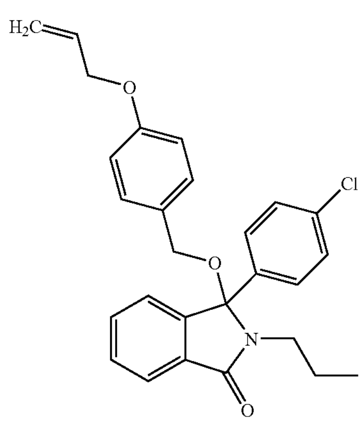 | 304 ± 42 |

| Number | Compound Descriptions | Structure | ELISA IC$_{50}$ ($\mu$M) |
|---|---|---|---|
| NU8241 | 3-(4-chlorophenyl)-3-(3-allyloxy-4-methoxy-benzyloxy)-2-propyl-2,3-dihydroisoindolin-1-one<br>477.97<br>C$_{28}$H$_{28}$ClNO$_4$ | 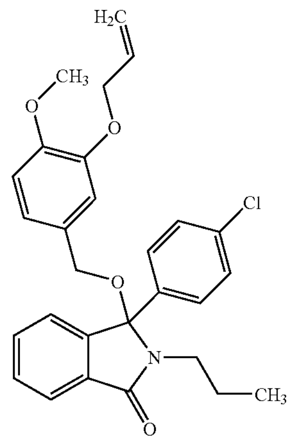 | 83 ± 5 |
| NU8242 | 3-(4-chlorophenyl)-3-(4-allyloxy-3-methoxy-benzyloxy)-2-propyl-2,3-dihydroisoindolin-1-one<br>477.97<br>C$_{28}$H$_{28}$ClNO$_4$ | 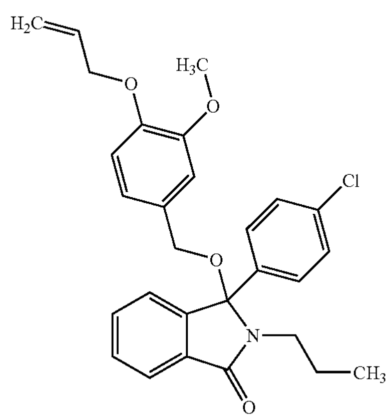 | 272 ± 5 |
| NU8245 | 3-(4-Chlorophenyl)-3-(4-hydroxy-3,5-dimethoxybenzyloxy)-2-prop-2-ynyl-2,3-dihydroisoindolin-1-one<br>463.9<br>C$_{26}$H$_{22}$ClNO$_5$ | 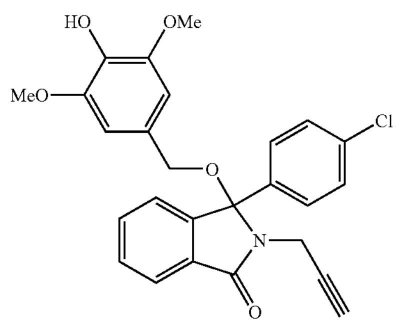 | 23 ± 4 |
| NU8265 | 3-(4-Chloro-phenyl)-2-cyclopropylmethyl-3-hydroxy-2,3-dihydro-isoindol-1-one<br>313.77<br>C$_{18}$H$_{16}$ClNO$_2$ | 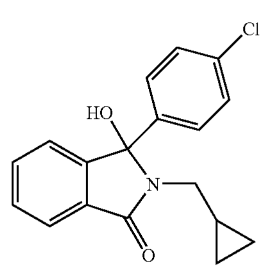 | >20 |

Particularly, preferred examples of compounds for use in carrying out the invention and which have been found to have particularly potent activity comprise the following:

| Number | Compound Descriptions | Structure | ELISA IC$_{50}$ ($\mu$M) |
|---|---|---|---|
| NU8165 | 2-benzyl-3-(4-chlorophenyl)-3-(3-hydroxy-propoxy)-2,3-dihydroisoindolin-1-one | 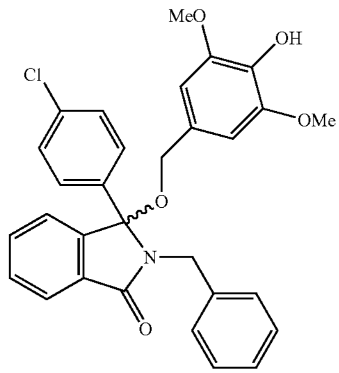 | 15.9 ± 0.8 |
| NU8231 | 3-(4-Chloro-phenyl)-3-(4-hydroxy-3,5-dimethoxy-benzyloxy)-2-propyl-2,3-dihydro-isoindolin-1-one 467.94 C$_{26}$H$_{26}$ClNO$_5$ | 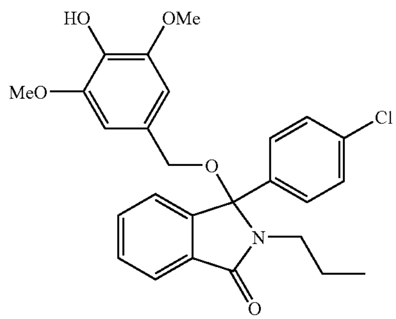 | 5.3 ± 0.9 |
| NU8243 | 3-(4-chlorophenyl)-3-(4-hydroxy-benzyl)-2-propyl-2,3-dihydroisoindolin-1-one 407.88 C$_{24}$H$_{22}$ClNO$_3$ | 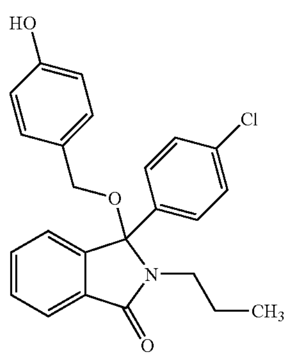 | 7.7 ± 0.3 |
| NU8244 | 3-(4-chlorophenyl)-3-(3-hydroxy-4-methoxy benzyloxy)-2-propyl-2,3-dihydroisoindolin-1-one 437.91 C$_{25}$H$_{24}$ClNO$_4$ | 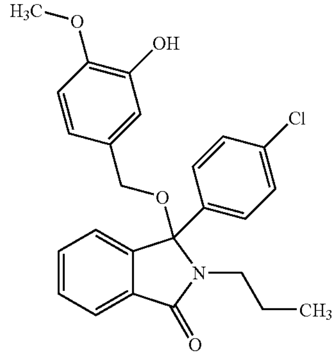 | 9.5 ± 1.9 |

| Number | Compound Descriptions | Structure | ELISA IC$_{50}$ ($\mu$M) |
|---|---|---|---|
| NU8249 | 2-Benzyl-3-(4-chlorophenyl)-3-(3-hydroxycyclopentyloxy)-2,3-dihydroisoindolin-1-one | 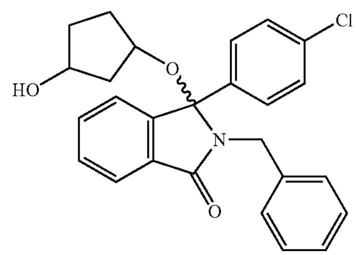 | 3 ± 1 |
| NU8253 | 3-(4-Chlorophenyl)-3-(3-hydroxy-cyclopentyloxy)-2-propyl-2,3-dihydro-isoindolin-1-one | 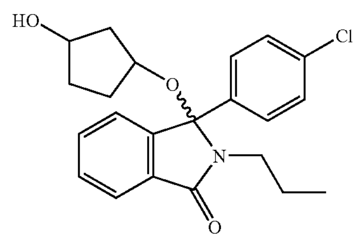 | 3.0 ± 0.7 |
| NU8257 | 3-(4-Chlorophenyl)-3-(3-hydroxy-cyclopentyloxy)-2-phenethyl-2,3-dihydroisoindolin-1-one 447.95 C$_{27}$H$_{26}$ClNO$_3$ | 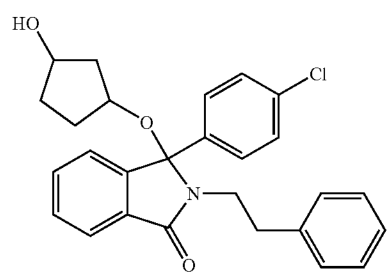 | 5.5 ± 1.7 |
| NU8260 | SK149 3-(4-Chloro-phenyl)-3-hydroxy-2-(4-nitro-benzyl)-2,3-dihydro-isoindol-1-one 394.8 C$_{21}$H$_{15}$ClN$_2$O$_4$ | 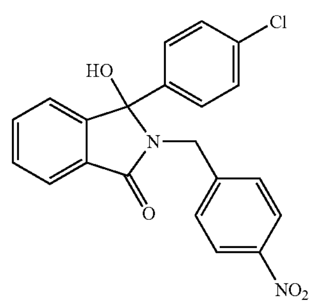 | 670 nM ± 150 |
| NU8261 | 3-(4-Chloro-phenyl)-3-(3-hydroxy-cyclopentyloxy)-2-(4-nitro-benzyl)-2,3-dihydro-isoindolin-1-one 478.9 C$_{26}$H$_{23}$ClN$_2$O$_5$ | 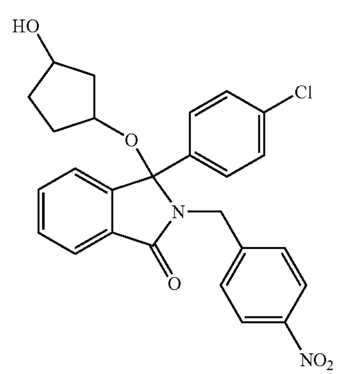 | 700 ± 160 nM |

-continued

| Number | Compound Descriptions | Structure | ELISA IC$_{50}$ ($\mu$M) |
|---|---|---|---|
| NU8274 | 2-(4-chlorobenzyl)-3-(4-chlorophenyl)-3-(3-hydroxycyclopentyloxy)-2,3-dihydroisoindolinin-1-one | 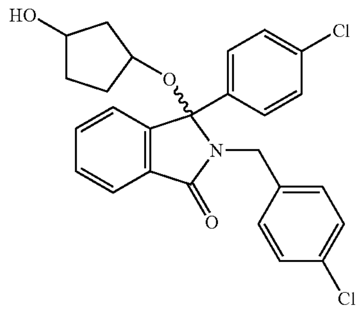 | 2.4 ± 0.7 |
| NU8279 | 3-(4-fluorophenyl)-3-(3-hydroxycyclopentyloxy)-2-propyl-2,3-dihydrisoindolinin-1-one | 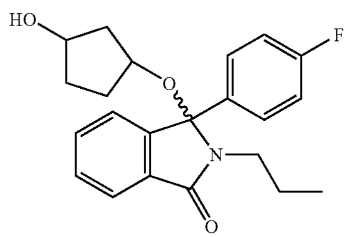 | >20 |
| NU8280 | 3-(4-chlorophenyl)-2-(cyclopropylmethyl)-3-(3-hydroxycyclopentyloxy)-2,3-dihydroisoindolinin-1-one | 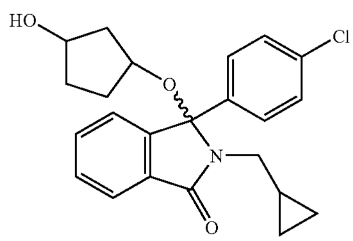 | 15.4 ± 2.3 |

Studies of the p53 binding pocket on the MDM2 protein guided the nature of the molecules synthesised. Thus the present invention provides small molecule inhibitors of MDM2-p53 interaction based on an isoindolinone scaffold. Preliminary screening studies, using an in vitro MDM2-p53 binding assay identified compounds NU8001, NU8006 and NU8009 as modest inhibitors of MDM2-p53 interaction having an IC$_{50}$ of around 200 μM (IC$_{50}$ is the concentration of a particular compound required to inhibit 50% of a specific measured activity, in this case inhibition of the MDM2-p53 interaction).

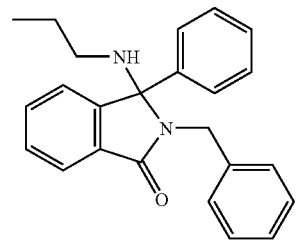

2-benzyl-3-phenyl-3-(propylamino)isoindolin-1-one (NU8006)

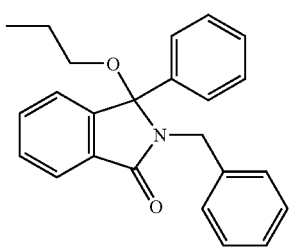

2-benzyl-3-phenyl-3-propoxy isoindolin-1-one (NU8001)

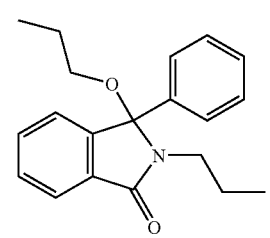

2-propyl-3-phenyl-3-propoxy isoindolinin-1-one (NU8009)

These compounds also displayed growth inhibitory activity in the NCI 60 cell line screen, and importantly were rated COMPARE negative with respect to any known classes of antitumour agents. The studies carried out fully support the theory that MDM2-p53 interaction inhibitory characteristics of compounds tested reflect an ability of these characteristics to act as effective antitumour drugs.

The inhibitory efficacies of the compounds of the present invention have been determined using the ELISA assay which for the avoidance of doubt is described below.

ELISA Assay

Streptavidin-coated 96-well plates are used to immobilise a biotin-tagged IP3 p53-derived peptide (MPRFMDY-WEGLN). This is a peptide analogue derived from the p53 binding site for MDM2 (QETFSDLWKLLP). IP3 has a higher affinity for MDM2 than the native peptide and has been used elsewhere to identify antagonists of the binding between MDM2 and p53 (Stoll et al 2001). Aliquots of MDM2 generated by in vitro translation are pre-incubated for 20 minutes at room temperature (i.e. 20-25° C.) with test compounds and controls, before transfer into the IP3-coated 96-well plates. Following a further incubation period of 90 minutes at 4° C., the plates are washed to remove unbound MDM2 and the residual bound MDM2 is detected using a primary monoclonal antibody (MDM2 Ab-1, clone IF2, Oncogene Research Products) and HRP-conjugated secondary antibody (Goat anti-mouse, Dako PO447). The HRP (horseradish peroxidase) is measured by a chemiluminescence reaction using standard reagents (Amersham Pharmacia™ RPN 2106) and an automatic injection 96-well plate illuminometer (EG & G Berthold Microplate LB 96V).

For validation and subsequently as positive controls, IP3 & AP peptides are used, together with the isoindolin-1-one lead compound that at the time shows the highest degree of antagonistic activity. Compound NU8231 is currently included as a standard "lead compound" positive control. AP is an octomer synthetic peptide that inhibits the p53-MDM2 interaction with high potency ($IC_{50}$=5.0 nM) and has been reported to stimulate p53 and downstream apoptotic pathways in intact tumour cell lines (Chene et al 2000). The AP peptide is included as a positive control for biological evaluation of the isoindolinones in the cell free binding assays.

All compounds are dissolved in DMSO and tested at three standard concentrations (initially 20 µM, 100 µM and 500 µM) in the presence of a fixed final concentration of 5% DMSO. The percentage inhibition of complex formation is expressed relative to a DMSO only control and an $IC_{50}$, defined as the concentration required for 50% inhibition of MDM2-p53 complex formation, determined by interpolation.

The ELISA assay shows a standard error for n=3 independent $IC_{50}$ determinations that is typically 10-15% of the mean value. Thus, the variation in the $IC_{50}$ determination for an individual compound is much smaller than the range of values for the compounds evaluated thus far is (26.7>500 µM).

Proposed Whole Cell

Compounds showing evidence of interference with p53-MDM2 binding in cell-free assays will be tested in intact cell systems for activation of p53 transcriptional function, growth inhibition and cytotoxicity. These tests will be carried out on cells of established p53 and MDM2 status. Cells will be challenged either with the compounds alone or in combination with a DNA damaging agent.

Functional endpoints for p53 activity will include a luciferase based reporter gene assay and transactivation of endogenous p53-regulated genes (WAF1 and MDM2) assayed by Western blotting and immunocytochemistry. Where appropriate, further characterisation of the cellular response to compounds of interest will include cell cycle checkpoint arrest measured by flow cytometry, and immunoprecipitation of p53-MDM2 complexes from intact cells.

Western Blot Method

Osteosarcoma cell line SJSA-1 was plated out in 55 mm dishes at a density of $2.5 \times 10^5$ cells in 3 mL of RPMI 1640 medium (Sigma) supplemented with 10% foetal bovine serum (FBS, Gibco), 1% (v/v) HEPES (Gibco), 1% (v/v) sodium pyruvate (Gibco) and 1.25 g/500 ml glucose (Sigma) for 48 hours in a 37° C. humidified incubator (Sanyo, MCO 20AIC) at a $CO_2$ concentration of 5%.

The dishes were treated with NU8231 at a final concentration of 5, 10, and 20 µM (at 1% DMSO) together with a 1% DMSO and an untreated control sample for 6 hours. The medium was then aspirated and the dishes were washed with 3 mL of cold PBS. The cells were then lysed in 40 µL of Sodium Dodecyl Sulphate (SDS, Sigma) lysis buffer, boiled at 100° C. for 10 minutes before sonication for 3×5 seconds at 20 microns (Soniprep 150, MSE).

The protein concentration for each of the samples was then determined using BCA Protein Assay Kit (Pierce), and 1:1 loading buffer consisting of β-mercaptoethanol (Sigma) and 0.5% bromophonol-blue (Sigma) were added to 40 µg of protein and made up to a final volume of 30 µL and boiled for 5 minutes at 100° C.

The samples were then loaded onto a precast 4-20% gradient polyacrylamide Tris-Glycine gels (15 wells, 1.5 mm thickness, Invitrogen Life Technologies), along with a pre-stained marker protein (SeeBlue, Invitrogen). The Gels were processed in Novex XCell (Invitrogen) at 180V and blotted onto a High Bond C membrane (Amersham Life Science) overnight at 30V.

The membrane was then blocked for one hour at room temperature in TBS-Tween containing 5% non-fat milk (TBST-M) followed by incubation with primary antibodies for MDM2 (MDM2-Ab1, 1:500, Oncogene), p53 (p53-D07, 1:1000, Novacastra), p21 (p21 Ab1, 1:100, Oncogene) and Actin (Actin AC40, 1:1000, Sigma) in PBST-M for 1 hour.

The membrane was then washed three times in TBST (15 minutes per wash) and then incubated for an additional 1 hour with a anti mouse or a rabbit horseradish peroxidase (HRP) secondary antibody (Dako, 1:1000) in PBST-M followed by a final wash consisting of six washes with TBST at 5 minutes per wash. Enhanced chemiluminescence (ECL, Amersham) detection reagents were then added onto the membrane which was exposed to a blue light sensitive X-ray film (Fuji Photo Film Co Ltd) and developed in an automated X-ray film processor, (Mediphot 937).

The present invention also relates to the therapeutic utility of isoindolin-1-one compounds described herein.

Thus, according to a further aspect of the present invention there is provided an isoindolin-1-one compound as hereinbefore defined for use in therapy. More specifically, the present invention also provides an isoindolin-1-one compound as hereinbefore defined for use as an active pharmaceutical substance for the treatment of cancer.

In a further aspect of the present invention there is provided the use of isoindolin-1-one compounds as hereinbefore defined in the manufacture of a medicament.

In a still further aspect of the present invention there is provided the use of isoindolinone compounds as hereinbefore defined in the manufacture of a medicament for the treatment of cancer.

As referred to herein "cancer" or "tumour" includes, but is not limited to, cancer of the lung, colon, pancreas, stomach, ovary, cervix, breast, prostate, bone, brain or skin. Compounds of the present invention have been shown to inhibit the interaction of p53 with MDM2. Such inhibition leads to cell arrest and apoptosis.

Accordingly, the compounds of the present invention are of particular interest for the treatment of a range of selected cancer tumours, and the invention further provides a method for the treatment of a patient suffering from cancer. Thus, a therapeutically effective non-toxic amount of a compound of formula I as hereinbefore defined, may be suitably administered orally, parenterally (including subcutaneously, intramuscularly, and intravenously or topically. The administration will generally be carried out repetitively at intervals, for example once or several times a day.

The amount of the compound of formula I, which is required in order to be effective as an antitumour agent for treating mammals will of course vary and is ultimately at the discretion of the medical or veterinary practitioner treating the mammal in each particular case. The factors to be considered by such a practitioner e.g. a physician, include the route of administration and pharmaceutical formulation; the mammal's body weight, surface area, age and general condition; and the chemical form of the compound to be administered. However, a suitable effective antitumour dose may be in the range of about 1.0 to about 75 mg/kg bodyweight, preferably in the range of about 5 to 40 mg/kg with most suitable doses being for example in the range of 10 to 30 mg.kg. In daily treatment for example, the total daily dose may be given as a single dose, multiple doses, e.g. two to six times per day, or by intravenous infusion for any selected duration. For example, in the case of a 75 kg mammal, the dose range could be about 75 to 500 mg per day and it is expected that a typical dose would commonly be about 100 mg per day. If discrete multiple doses are indicated, treatment might typically be 50 mg of the compound of formula given 4 times per day in the form of a tablet capsule, liquid (e.g. syrup) or injection.

While it may be possible for the compounds of formula I to be administered alone as the raw chemical, it is preferable to present the compound in a pharmaceutical composition. Thus, the invention also provides pharmaceutical compositions comprising an effective amount of an isoindolinone compound as hereinbefore defined which forms the active therapeutic ingredient. Such pharmaceutical compositions for medical use will be formulated in accordance with any of the methods well known in the art of pharmacy for administration in any convenient manner. The isoindolin-1-one compounds will usually be admixed with at least one other ingredient providing a compatible pharmaceutically acceptable additive carrier, diluent or excipient, and may be presented in unit dosage form.

The carrier(s) must be pharmaceutically acceptable in the sense of being compatible with the other ingredients of the formulation and not deleterious to the recipient thereof.

The possible formulations include those suitable for oral, rectal, topical and parenteral (including subcutaneous infra-muscular and intravenous) administration or for administration to the lung or other absorptive site such as the nasal passages.

All methods of formulation in making up such pharmaceutical compositions will generally include the step of bringing the compound of formula I into association with a carrier which constitutes one or more accessory ingredients. Usually, the formulations are prepared by uniformly and intimately bringing the compound of formula I into association with a liquid carrier or with a finely divided solid carrier or with both and then, if necessary, shaping the product into desired formulations. Formulations of the present invention suitable for oral administration may be presented as discrete units such as capsules, cachets, tables or lozenges, each containing a predetermined amount of the compound of formula I; as a powder or granules; or a suspension in an aqueous liquid or non-aqueous liquid such as a syrup, an elixir, an emulsion or a draught. The compound of formula I may also be presented as bolus, electuary or paste.

A tablet may be made by compression or moulding, optionally with one or more accessory ingredients. Compressed tables may be prepared by compressing, in a suitable machine, the compound of formula I in a free-flowing form such as a powder or granules, optionally mixed with a binder, lubricant, inert diluent, surface active or dispersing agent. Moulded tables may be may be moulding, in a suitable machine, a mixture of the powdered compound of formula I with any suitable carrier.

A syrup may be made by adding the compound of formula I to a concentrated, aqueous solution of a sugar, for example sucrose, to which may be added any desired accessory ingredients. Such accessory ingredient(s) may include flavourings, an agent to retard crystallisation of the sugar or an agent to increase the solubility of any other ingredient, such as a polyhydric alcohol, for example glycerol or sorbitol. Formulations for rectal administration may be presented as a suppository with a usual carrier such as cocoa butter.

Formulations suitable for parental administration convenient comprise a sterile aqueous preparation of the compound of formula I, which is preferably isotonic with the blood of the recipient.

In addition to the aforementioned ingredients, formulations of this invention, for example ointments, creams and such like, may include one or more accessory ingredients, for example a diluent, buffer, flavouring agent, binder, surface active agent, thickener, lubricant and/or a preservative (including an antioxidant) or other pharmaceutically inert excipient.

The compounds of the present invention may also be made up for administration in liposomal formulations, which can be prepared by methods well-known in the art. Therefore, the invention also includes the use of the isoindolinone compounds hereinbefore defined for the manufacture of medicaments or pharmaceutical compositions for treating cancer, wherein the isoindolinone itself provides an effective antitumour agent.

The isoindolinone compounds of the present invention may be administered alone or as a combination therapy along with conventional radiotherapy or chemotherapy treatments.

The present invention will now be described further by way of example only. The following examples and description of stages in synthetic routes of preparation of various compounds of interest serve further to illustrate the present invention.

General Methods for the Preparation of isoindolin-1-ones where x is O

Scheme 1

Method A

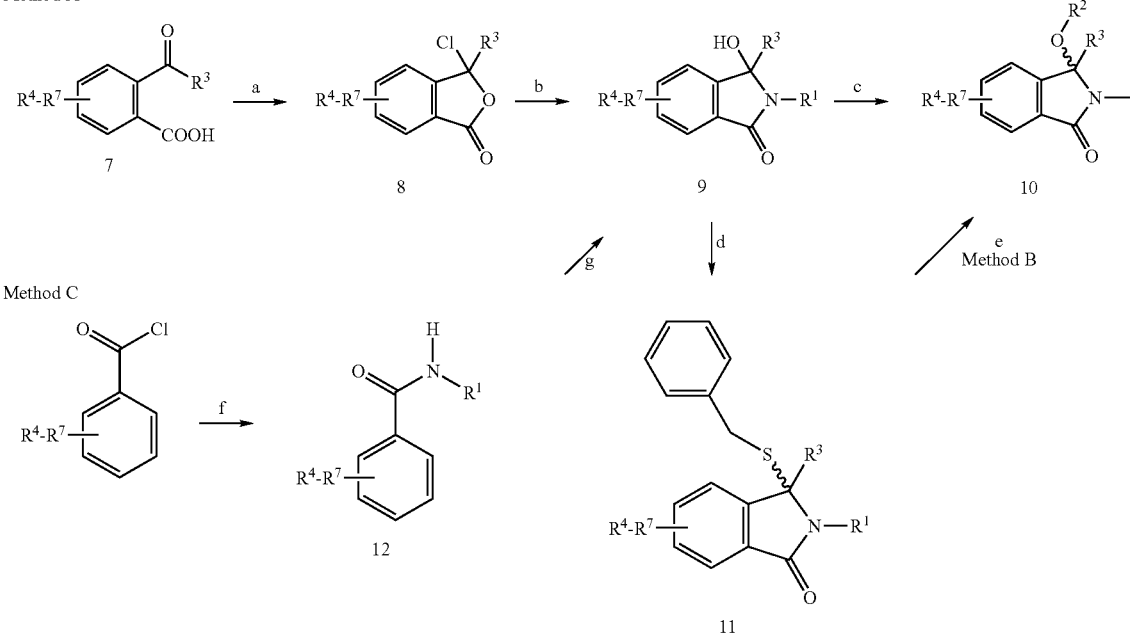

Method C

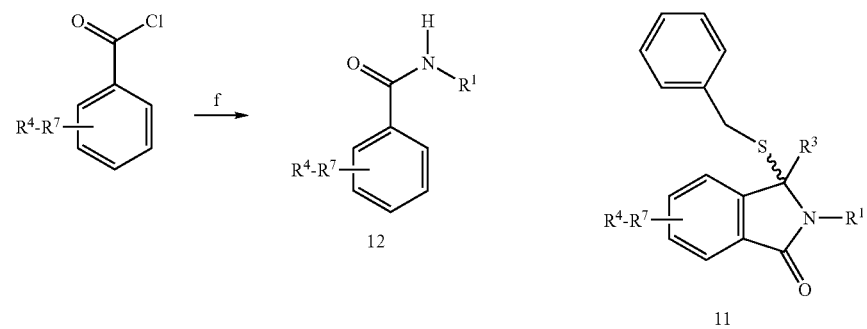

a) SOCl$_2$, DMF, THF; b) R$^1$NH$_2$, THF; c) SOCl$_2$, DMF, THF; ii) ROH, THF.; d) THF, mercaptam; e) NIS, CIS, R$^2$OH; f) R$^1$—NH$_2$; and g) s-BuLi, R$^3$COOEt, THF, e) I) SOCl$_2$, THF, ii) R$^2$OH, d) R$^2$COCl, THF, base.

The final compounds (10) were isolated as racemic mixtures.

The compounds of the present invention were synthesised using one of the general procedures below. The general procedures are described with respect to isoindolin-1-ones falling into the general classes specified.

General Procedure A:
3-Hydroxy-3-aryl-2,3-dihydroisoindolin-1-ones

Distilled THF (20 mL) was added to 3-chloro-3-aryl-3H-isobenzofuran-1-one (1 mol. equiv.) followed by an excess of the appropriate amine (unless otherwise stated) and an excess of triethylamine, resulting in the formation a creamy white/yellow precipitate. The system was stirred at room temperature under nitrogen for 4 h (unless otherwise stated) and monitored by TLC. On completion the solvent was removed under vacuum, the residue was taken up in ethyl acetate (30 mL), washed with water (3×20 mL), brine (10 mL) and dried with MgSO$_4$. The solvent was removed under vacuum and the resulting creamy white/yellow solid (unless otherwise stated) was recrystallised in the minimum amount of boiling ethyl acetate (unless otherwise stated).

General Procedure B:
3-Chloro-3-aryl-2,3-dihydroisoindolin-1-ones

Distilled THF (10 mL) was added to the appropriate 3-hydroxy-3-aryl-2,3-dihydroisoindolin-1-one (1 mol. equiv.) followed by thionyl chloride (2 mol equiv.) (unless otherwise stated) and a catalytic amount of DMF (3 drops). The system was stirred at room temperature under nitrogen for 4 h (unless otherwise stated) and monitored by TLC. Removal of the solvent under vacuum gave the 3-chloro-3-phenyl-2,3-dihydroisoindolin-1-one as a yellow/colourless oil that was used immediately without further purification.

General Procedure C:
3-Alkoxy-3-aryl-2,3-dihydroisoindolin-1-ones

Distilled THF (10 mL) was added to the appropriate 3-chloro-3-aryl-2,3-dihydroisoindolin-1-one (1 mol. equiv.) followed by an excess of the appropriate alcohol (unless otherwise stated) and an excess of the appropriate base (unless otherwise stated). The system was stirred at room temperature under nitrogen for 4 h (unless otherwise stated) and monitored by TLC. On completion the solvent was removed under vacuum, the residue was taken up in ethyl acetate (30 mL), washed with water (3×20 mL), brine (10 mL) and dried with MgSO$_4$. The solvent was removed to give the crude 3-alkoxy-3-phenyl-2,3-dihydroisoindolin-1-one.

General Procedure D: Synthesis of 3-hydroxyisoindolin-1-ones (10)

To a solution of the appropriate 2-benzoylbenzoic acid (1.0 equiv.) in THF was added thionyl chloride (2.2 equiv.) and DMF (3 drops). The mixture was stirred at room temperature 16 h, then concentrated in vacuo to give a clear oil. The residues were dissolved in THF (10 mL), the appropriate primary amine (1.0 equiv.), and triethylamine (2.2 equiv.) were added, and the mixture stirred at rt for 16 h. The mixture was either filtered and submitted to extraction with EtOAc (15 mL), sodium bicarbonate (20 mL) and water (15 mL) or treated immediately with EtOAc (15 mL), saturated sodium bicarbonate (15 mL) and water (15 mL). The organic layers were combined, dried (Na$_2$SO$_4$) and concentrated in vacuo. Chromatography (EtOAc, petrol 1:4) or by crystallisation with a minimum of EtOAc and an excess of petrol gave the desired product.

General Procedure E: 3-Chloro-3-(4-chlorophenyl)-2,3-dihydroisoindolin-1-ones

Distilled THF (10 mL) was added to the appropriate 3-(4-chlorophenyl)-3-hydroxy-2,3-dihydroisoindolin-1-one (1 mol. equiv.) followed by thionyl chloride (2 mol equiv.) (unless otherwise stated) and a catalytic amount of DMF (3 drops). The system was stirred at room temperature under nitrogen for 4 h (unless otherwise stated) and monitored by TLC. Removal of the solvent under vacuum gave the 3-chloro-3-(4-chlorophenyl)-2,3-dihydroisoindolin-1-one as a yellow/colourless oil that was used immediately without further purification.

General Procedure F: 3-Alkoxy-3-(4-chlorophenyl)-2,3-dihydroisoindolin-1-ones

Distilled THF (10 mL) was added to the appropriate 3-chloro-3-(4-chlorophenyl)-2,3-dihydroisoindolin-1-one (1 mol. equiv.) followed by an excess of the appropriate alcohol (unless otherwise stated) and an excess of the appropriate base (unless otherwise stated). The system was stirred at room temperature under nitrogen for 4 h (unless otherwise stated) and monitored by TLC. On completion the solvent was removed under vacuum, the residue was taken up in ethyl acetate (30 mL), washed with water (3×20 mL), brine (10 mL) and dried with MgSO$_4$. The solvent was removed to give the crude 3-alkoxy-3-(4-chlorophenyl)-2,3-dihydroisoindolin-1-one.

General Procedure G: 3-Chloro-3-[4-(2-trimethylsilanylethoxy-methoxy)-phenyl]-2,3-dihydroisoindolin-1-one Distilled THF (10 mL) was added to the appropriate 3-hydroxy-3-[4-(2-trimethylsilanylethoxymethoxy)phenyl]-2,3-dihydroisoindolin-1-one (1 mol. equiv.) followed by thionyl chloride (1.4 mol equiv.) (unless otherwise stated) and a catalytic amount of DMF (3 drops). The system was stirred at room temperature under nitrogen for 2 h (unless otherwise stated) and monitored by TLC. Removal of the solvent under vacuum gave the 3-chloro-3-[4-(2-trimethylsilanylethoxymethoxy)-phenyl]-2,3-dihydroisoindolin-1-one as a yellow/colourless oil that was used immediately without further purification.

General Procedure H: 3-Alkoxy-2,3-dihydroisoindolin-1-ones

To a solution of 11a (0.51 g, 1.50 mmol) in THF (7 mL), was added the appropriate alcohol (3.0 or 4.0 mol. eq.). The reactions were stirred at room temperature for 72 h, unless stated otherwise, then concentrated in vacuo. The residue was dissolved in EtOAc (20 mL) and washed with water (3×10 mL). The organic layer was dried (MgSO$_4$) and concentrated in vacuo to give the crude 3-alkoxy-2,3-dihydroisoindolin-1-one.

General Procedure I: Synthesis of isoindolinin-1-ones Derivatives with R$^4$ Alkoxy Substitution A solution of the appropriate 3-hydroxyisoindolininone 10 (1.0 equivalent) in THF (10 mL) was treated with a solution of thionyl chloride (2.2 equivalents), and a catalytic amount of DMF. After 16 h, the mixture was concentrated in vacuo. The residues were dissolved in either DMF (5-10 ml) or THF (5-10 mL) as appropriate and treated with the appropriate primary alcohol (1.1 equivalent or 2.2 equivalents) with or without triethylamine (2.2 equivalents). The reaction mixture was stirred at rt 20 h reaction. The mixture was stirred at room temperature under a nitrogen atmosphere, (EtOAc/petrol:3:2). After 20 h, the solvent was removed in vacuo. The crude product was extracted with EtOAc (15 mL) and water (20 mL). The organic layers were combined and dried (Na$_2$SO$_4$), and concentrated in vacuo. Purification by flash chromatography (EtOAc, petrol; 1:4) and by recrystallisation from suitable solvents.

General Procedure J: 3-Alkoxy-2,3-dihydro-isoindolin-1-ones

The appropriate 3-aryl-2-benzyl-3-benzylsulphanyl-2,3-dihydro-isoindolin-1-one (1 mol. equiv.) in THF (4 mL) was added to a solution of NIS (1.1 mol. equiv.), CSA (0.1 mol. equiv.) and the appropriate alcohol (2.2 mol. equiv.) in THF (3 mL). The reaction was stirred in the dark at room temperature for 4 h before removal of the solvent under vacuum. The brown residue was taken up into ethyl acetate (30 mL) and washed with aqueous sodium thiosulphate (2×30 mL). The organic layer was collected and dried (Na$_2$SO$_4$) and the solvent removed under vacuum to give the 3-alkoxy-2,3-dihydro-isoindolin-1-one.

N-Cyclohexylmethylbenzamide

Cyclohexylmethylamine (4.37 mL, 33.6 mmol) was added to a solution of benzoyl chloride (2.47 mL, 21 mmol) in THF (20 mL) at 0° C., and stirring continued 16 h. The mixture was filtered, diluted with water (10 mL) and extracted with EtOAc (3×10 mL). The combined organic layers were washed with brine (10 mL), dried (Na$_2$SO$_4$), and concentrated in vacuo. The product crystallised (2.1 g, 45%) $^1$H-NMR (300 MHz, CDCl$_3$) $\delta_H$ 7.76 (1H, m, Ar); 7.29 (8H, m, Ar); 1.04 (2H, m, CH$_2$); 1.14 (2H, m, CH$_2$); 1.61 (7H, m, 3×CH$_2$); 3.23 (2H, t, J=6.78 Hz, N—CH$_2$); 6.15 (1H, s, NH); 7.37 (3H, m, ArH); 7.70 (2H, m, ArH); LCMS (ESI+) 218 [M+H]$^+$.

General Procedure K

To a solution of n-cyclohexylmethylbenzamide (250 mg, 1.14 mmol) in THF (5 mL) was added dropwise sec-butyl lithium (1.4 M in hexanes; 1.79 mL, 2.51 mmol) at −78° C. and stirring continued 30 min. A solution of the appropriate benzonitrile (0.17 g, 1.3 mmol) in THF (1 mL) was added dropwise and stirring continued for a further 30 min at −78° C. The reaction was quenched (sat NH$_4$Cl) and extracted with DCM (4×50 mL). The combined organic extracts were washed with brine (50 mL), dried (MgSO$_4$), and concentrated in vacuo to give the product as a fine white solid.

General Procedure L

To the appropriate 3-aminoisoindolinone (200 mg, 0.57 mmol) and triethylamine (0.24 mL, 1.71 mmol) in DCM (2 mL) was added benzoyl chloride (0.13 mL, 1.14 mmol). The solution was stirred 20 h, then concentrated in vacuo. Chromatography gave the product.

The following specific examples as hereinbefore described were prepared using the general procedures described above. The preparation of some precursor compounds is also described:

2-Benzyl-3-chloro-3-phenyl-2,3-dihydroisoindolin-1-one (11a)

A solution of 2-benzyl-3-hydroxy-3-phenyl-2,3-dihydroisoindolin-1-one 10a (0.25 g, 0.79 mmol) in THF (20 mL) was reacted with thionyl chloride (0.07 mL, 0.87 mmol) and DMF (3 drops), the mixture was stirred for 16 h, and concentrated in vacuo giving 11a as an orange solid (0.27 g, 0.79 mmol) which was used without further purification.

2-Methylacrylic acid 2-(1-hydroxy-3-oxo-1-phenyl-1,3-dihydroisoindolin-2-yl)ethyl ester (10d)

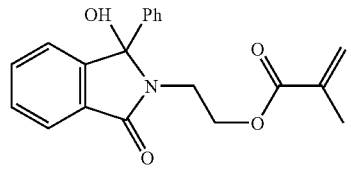

General procedure D: 2-benzoyl benzoic acid (0.75 g, 3.3 mmol), 2-aminoethyl methacrylate hydrochloride (0.60 g, 3.65 mmol), and triethylamine (1.01 mL, 7.26 mmol) in THF (10 mL. Chromatography (silica; EtOAc, petrol; 3:7) gave 10d as a clear oil (1.04 g, 3.08 mmol) FTIR ν (cm$^{-1}$): 3326 (OH), 2930 (CH—Ar), 1679 (very strong C=O absorption). 1H NMR (300 MHz, CDCl$_3$) δ$_H$ (ppm) 1.90 (3H, s, CH$_3$), 3.13 (1H, m, CH$_2$), 4.12 (2H, m, OCH$_2$), 4.67 (1H, m, NCH$_2$), 5.58 (1H, s, CH), 6.09 (1H, s, CH), 7.28-7.80 (13H, m, Ar—H), 7.81 (1H, m, Ar—H$_4$). 13C NMR (75 MHz, CDCl$_3$) δC (ppm) 14.6 (CH$_3$), 18.7 (CH$_2$), 38.9 (CH$_2$), 63.5 (CH$_2$), 91.8 (O—C—N), 123-149.5 (C—Ar), 168.3 (C=O), 168.5 (C=O). LCMS (ESI+) m/z=360, [M+Na]$^+$.

3-Hydroxy-2-[2-(3H-imidazol-4-yl)ethyl]-3-phenyl-2,3-dihydroisoindolin-1-one (10e)

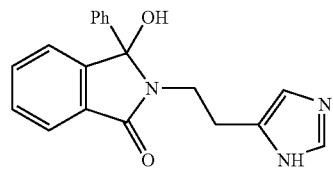

General procedure D: 2-benzoylbenzoic acid (0.75 g, 3.3 mmol), histamine dihydrochloride (0.67 g, 3.63 mmol), and triethylamine (1.51 mL, 10.9 mmol). Chromatography (silica; MeOH, DCM; 5:95) gave 10e as a white powder (0.34 g, 1.07 mmol, 33%) mp 190° C. FTIR ν (cm$^{-1}$): 1782 (NC=C), 1693 (C=O). $^1$H NMR (300 MHz, CDCl$_3$) δ$_H$ (ppm): 2.87 (1H, m, CH$_2$), 3.11 (2H, m, CH$_2$), 4.03 (1H, m, CH$_2$), 6.67 (1H, s, CH), 7.28 (1H, s, CH), 7.40 (8H, m, Ar—H), 7.93 (1H, m, H$_7$). $^{13}$C NMR (75 MHz, CDCl$_3$) δ$_C$ (ppm): 26 (CH$_2$), 39.1 (CH$_2$), 53.8 (C=CH), 92.6 (N—C—O), 115.4-139.7 (C—Ar), 150.7 (C=C—N), 169 (C=O). LCMS (ESI+): m/z=320 [M+H]$^+$. Anal. Calc for C$_{19}$H$_{17}$N$_3$O$_2$: C, 71.46; H, 5.37; N, 13.16%; Found C, 70.99; 5H, 4.27; N, 7.54%.

2-[2-(tert-Butyldiphenylsilanyloxy)ethyl]-3-hydroxy-3-phenyl-2,3-dihydroisoindolin-1-one (10q)

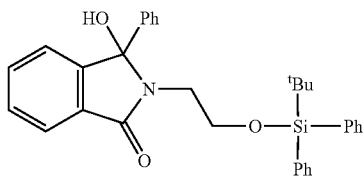

General procedure D: 2-benzoylbenzoic acid (460 mg, 2 mmol), thionyl chloride (483 mg, 4.0 mmol), 2-(tert-butyldiphenylsilanyloxy)ethylamine[34] (720 mg, 2.4 mmol), triethylamine (600 mg, 6.0 mmol). Chromatography (silica; 20% EtOAc, petroleum ether) gave 10q as a white solid (860 mg, 83%) IR ν (cm$^{-1}$): 2936, 2859, 1683, 1470, 1421, 1398, 1312, 1195, 1170, 1107, 1051, 935, 822. $^1$H-NMR (300 MHz, CDCl$_3$) δ$_H$ 7.74 (1H, m, Ar), 7.46 (4H, m, Ar); 7.28 (14H, m, Ar). 5.65 (1H, s, OH); 3.90 (2H, m, OCH$_2$); 3.58 (1H, dt, J=3.09 & 6.34 Hz, NCH$_2$); 2.89 (1H, dt, J=3.42 & 4.79 Hz, —NCH$_2$); 0.98 (9H, s, $^t$Bu). $^{13}$C-NMR (75 MHz, CDCl$_3$) δ$_C$ 19.46, 27.21, 42.14, 64.08, 90.98, 123.08, 123.77, 126.76, 128.27, 128.31, 128.80, 129.13, 129.50, 130.21, 130.45, 130.48, 132.26, 132.53, 133.13, 135.92, 140.11, 149.60, 168.56.

2-[4-(tert-Butyldiphenylsilanyloxy)propyl]-3-hydroxy-3-phenyl-2,3-dihydroisoindolin-1-one (10s)

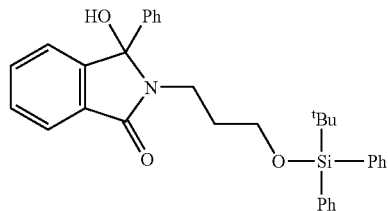

General procedure D: 2-benzoylbenzoic acid (230 mg, 1.0 mmol), thionyl chloride (240 mg, 2.0 mmol), 2-(tert-butyldiphenylsilanyloxy)propylamine (383 mg, 1.2 mmol) triethylamine (310 mg, 3.0 mmol). Chromatography (silica; 40% EtOAc, petroleum ether) gave 10s as a white solid (375 mg, 71%). $^1$H-NMR (300 MHz, CDCl$_3$) δ$_H$ 7.99 (1H, d, J=7.53 Hz, Ar); 7.50 (8H, m, Ar); 7.24 (10H, m, Ar); 3.63 (3H, m, OCH$_2$ and NCH$_2$); 2.79 (1H, q, J=7.01 Hz, NCH$_2$); 1.87 (1H, m, CH$_2$); 1.58 (1H, m, CH$_2$); 0.81 (9H, s, $^t$Bu). $^{13}$C-NMR (75 MHz, CDCl$_3$) δ$_C$ 19.37, 27.05, 30.98, 37.83, 63.22, 92.08, 123.04, 123.65, 126.55, 128.10, 128.81, 128.99, 129.70, 129.90, 130.13, 120.85, 131.19, 132.96, 133.38, 133.55, 135.88, 135.97, 137.45, 139.40, 142.87, 149.64, 168.70, 170.00. LCMS (ESI+) 522 [M+H]$^+$.

2-Furan-2-ylmethyl-3-hydroxy-3-phenyl-2,3-dihydroisoindolin-1-one (10t). 2-benzoylbenzoic acid (460 mg, 2 mmol), thionyl chloride (482 mg, 4.0 mmol), furfurylamine (236 mg, 2.4 mmol) triethylamine (610 mg, 6.0 mmol).

Chromatography (silica; 40% EtOAc, petroleum ether) gave 10t as a white solid (360 mg, 58%). $^1$H-NMR (300 MHz, CDCl$_3$) δ$_H$ 7.62 (1H, m, Ar); 7.35 (2H, m, Ar); 7.19 (6H, m, Ar); 7.06 (1H, s, OH); 6.01 (1H, m, CH$_2$); 5.84 (1H, m, Ar); 4.43 (1H, d, J=15.76 Hz, CH); 4.03 (2H, t, J=15.75 Hz, NCH$_2$). $^{13}$C-NMR (125 MHz, CDCl$_3$) δ$_C$ 35.57, 91.57, 108.63, 110.70, 123.25, 123.80, 126.44, 128.66, 128.74, 129.81, 130.23, 133.29, 138.56, 141.97, 149.49, 150.86, 168.16. LCMS (ESI+) 306 [M+H]$^+$.

3-Chloro-3-phenyl-3H-isobenzofuran-1-one

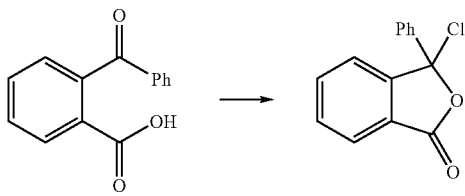

Dry THF (20 mL) was added to 2-benzoylbenzoic acid (0.51 g, 2.25 mmol) followed by thionyl chloride (0.18 mL, 2.48 mmol) and DMF (3 drops). The reaction mixture was stirred at room temperature overnight and monitored by TLC. Removal of the solvent in vacuo yielded a clear oil (0.55 g, 2.26 mmol, 100%); R$_f$ 0.68 (40:60 ethyl acetate:petrol).

3-Hydroxy-3-phenyl-2-propyl-2,3-dihydro-isoindolin-1-one

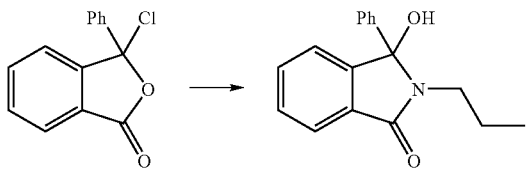

3-Chloro-3-phenyl-3H-isobenzofuran-1-one (0.56 g, 2.21 mmol) was reacted with redistilled propylamine (0.40 mL, 2.43 mmol) as for General Procedure A giving 3-hydroxy-3-phenyl-2-propyl-2,3-dihydro-isoindolin-1-one as an off-white solid. This was dissolved in the minimum of boiling ethyl acetate and recrystallised by dropwise addition of petrol to give a white solid (0.51 g, 1.92 mmol, 87%); R$_f$ 0.48 (40:60 ethyl acetate:petrol); mp 179-183° C. Lit. 184-185° C.[229]

Anal. Calcd for C$_{17}$H$_{17}$NO$_2$: C, 76.40; H, 6.41; N, 5.24%. Found: C, 76.00; H, 6.11; N, 5.06%. IR (KBr) υ$_{max}$ (cm$^{-1}$): 3180 (OH), 1678 (CO), 1059, 771, 702. $^1$H NMR (200 MHz, d$_6$-DMSO) δ 0.83-0.90 (3H, t, J=7.5 Hz, —NCH$_2$CH$_2$CH$_3$), 1.74-1.61 (2H, m, —NCH$_2$CH$_2$CH$_3$), 2.90-3.05 (2H, m, —NCH$_2$CH$_2$CH$_3$), 7.19 (1H, s, —OH, exchangeable with D$_2$O), 7.34-7.51 (6H, m, aromatic-H), 7.58-7.69 (2H, m, isoindolinone-H), 7.80-7.84 (1H, m, isoindolinone-H). $^{13}$C NMR (50 MHz, d$_6$-DMSO) δ 11.92 (—CH$_3$), 22.01 (—CH$_2$CH$_3$), 41.07 (—NCH$_2$—), 90.87 (C-3), 122.70, 123.05, 126.16, 128.37, 128.78, 129.46, 130.97, 132.70 (C8), 140.64 (C9), 149.97, 166.96 (C-1). MS (EI) m/z 267 [M+].

2-Benzyl-3-hydroxy-3-phenyl-2,3-dihydro-isoindolin-1-one

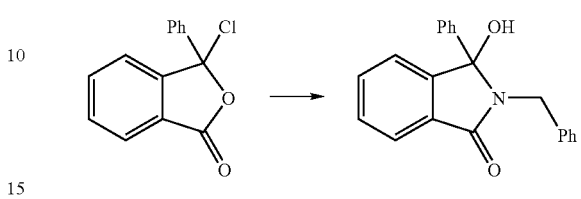

3-Chloro-3-phenyl-3H-isobenzofuran-1-one (0.55 g, 2.23 mmol) was reacted with redistilled benzylamine (0.53 mL, 2.45 mmol) as for General Procedure A giving 2-benzyl-3-hydroxy-3-phenyl-2,3-dihydro-isoindolin-1-one as an oily white solid. This was dissolved in the minimum of boiling ethyl acetate and recrystallised by dropwise addition of petrol to give a white crystalline solid (0.58 g, 1.84 mmol, 83%); R$_f$ 0.53 (40:60 ethyl acetate:petrol); mp 151-155° C. Lit 151-152° C.[232]

Anal. Calcd for C$_{21}$H$_{17}$NO$_2$: C, 80.00; H, 5.43; N, 4.44%. Found: C, 79.65; H, 5.33; N, 4.54%. IR (KBr) υ$_{max}$ (cm$^{-1}$): 3287 (OH), 1678 (CO), 1061, 768, 706. $^1$H NMR (200 MHz, d$_6$-DMSO) δ 4.23-4.31 (1H, d, J=15.5 Hz, —NCH$_2$C$_6$H$_5$), 4.55-4.63 (1H, d, J=15.5 Hz, —NCH$_2$C$_6$H$_5$), 7.26-7.29 (5H, m, —NCH$_2$C$_6$H$_5$), 7.31 (1H, s, —OH, exchangeable with D$_2$O), 7.36-7.58 (6H, m, aromatic-H), 7.61-7.70 (2H, m, aromatic-H), 7.82-7.86 (1H, m, isoindolinone-H). $^{13}$C NMR (50 MHz, d$_6$-DMSO) δ 42.91 (NCH$_2$C$_6$H$_5$), 91.05 (C-3), 122.85, 123.25, 126.32, 126.78, 128.09, 128.16, 128.30, 128.66, 129.57, 130.78, 132.92 (C8), 138.47, 140.27 (C-9), 149.93, 167.22 (C-1). MS (EI) m/z 315 [M+].

2-Benzyl-3-(3-Hydroxy-propoxy)-3-phenyl-2,3-dihydro-1H-isoindolin-1-one (NU8034)

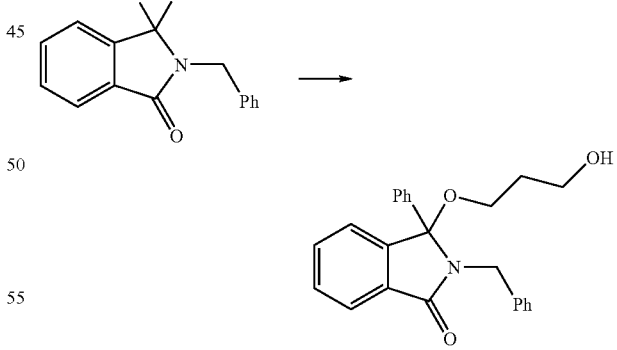

2-Benzyl-3-chloro-3-phenyl-2,3-dihydro-isoindolin-1-one (0.53 g, 1.60 mmol) in THF (5 mL) was added dropwise to 1,3-propanediol (10 mL) and stirred at room temperature for 20 h. The solvent was removed under vacuum and the crude reaction mixture was taken up into DCM (2×20 mL) and washed with water (2×20 mL). The organic layer was collected and dried (Na$_2$SO$_4$). Removal of the solvent in vacuo yielded 2-benzyl-3-(3-hydroxy-propoxy)-3-phenyl-2,3-dihydro-1H-isoindolin-1-one as a yellow oil. This was dissolved in the minimum amount of diethyl ether and recrystallised by dropwise addition of petrol to give a white solid (0.21 g, 0.56 mmol, 35%); $R_f$ 0.23 (40:60 ethyl acetate:petrol); mp 89-92° C.

Anal. Calcd♦ for $C_{24}H_{23}NO_3$: C, 77.19; H, 6.21; N, 3.75%. Found: C, 76.76; H, 6.01; N, 3.62%. IR (KBr) $\upsilon_{max}$ (cm$^{-1}$): 3428 (OH), 1690 (CO). $^1$H NMR (200 MHz, d$_6$-DMSO) δ 1.20-1.53 (2H, m, —OCH$_2$CH$_2$CH$_2$OH), 2.77-2.94 (2H, m, —OCH$_2$CH$_2$CH$_2$OH), 3.29-3.44 (2H, m, —OCH$_2$CH$_2$CH$_2$OH), 4.04-4.11 (1H, d, J=15.0 Hz, —NCH$_2$C$_6$H$_5$), 4.39-4.44 (1H, t, —OCH$_2$CH$_2$CH$_2$OH, exchangeable with D$_2$O), 4.71-4.79 (1H, d, J=15.0 Hz, —NCH$_2$C$_6$H$_5$), 7.29-7.41 (11H, m, aromatic-H), 7.65-7.75 (2H, m, aromatic-H), 7.93-7.97 (1H, m, isoindolinone-H). $^{13}$C NMR (50 MHz, d$_6$-DMSO) δ 32.20 (—OCH$_2$CH$_2$CH$_2$OH), 42.82 (—NCH$_2$C$_6$H$_5$), 57.87 and 57.99 (—OCH$_2$CH$_2$CH$_2$OH), 60.05 (—OCH$_2$CH$_2$CH$_2$OH), 95.12 (C-3), 123.38, 123.49, 126.39, 127.28, 128.34, 128.70, 128.85, 130.22, 131.37, 133.26, 137.89, 139.05, 145.73, 167.68 (C-1). MS (EI) m/z 373 [M+].

Figures given are not within 0.4% of theoretical values

2-Benzyl-3-(4-tert-butyl-benzyloxy)-3-phenyl-2,3-dihydro-isoindolin-1-one (NU8113)

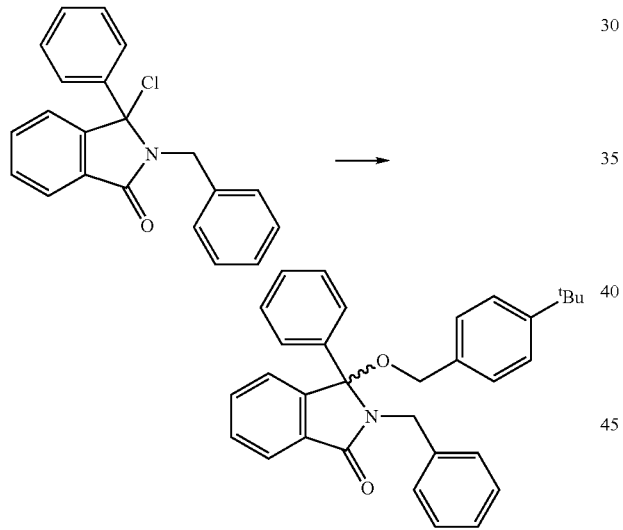

2-Benzyl-3-chloro-3-phenyl-2,3-dihydro-isoindolin-1-one (0.51 g, 1.50 mmol) was reacted with 4-tert-butyl-benzyl alcohol (1.06 mL, 5.99 mmol) as for General Procedure G yielding 2-benzyl-3-(4-tert-butyl-benzyloxy)-3-phenyl-2,3-dihydro-isoindolin-1-one as a clear oil. The crude product was purified by flash column chromatography (silica gel, 10:90 ethyl acetate:petrol) to give a cloudy white oil. Trituration in petrol yielded a white powder (0.30 g, 0.64 mmol, 43%); $R_f$ 0.25 (10:90 ethyl acetate:petrol); mp 107-108° C.

Anal. Calcd for $C_{32}H_{31}NO_2$: C, 83.27; H, 6.77; N, 3.03%. Found: C, 83.29; H, 6.63; N, 2.83%. IR (Diamond ATR) $\upsilon_{max}$ (cm$^{-1}$): 1698 (CO), 1383, 1356, 1050, 760, 699. $^1$H NMR (200 MHz, CDCl$_3$) δ 1.23 (9H, s, —OCH$_2$C$_6$H$_4$C(CH$_3$)$_3$), 3.59-3.72 (2H, tented dd, —OCH$_2$C$_6$H$_4$C(CH$_3$)$_3$), 3.97-4.04 (1H, d, J=14.5 Hz, —NCH$_2$C$_6$H$_5$), 4.68-4.75 (1H, d, J=14.5 Hz, —NCH$_2$C$_6$H$_5$), 6.81-6.85 (2H, d, J=8.0 Hz, —OCH$_2$C$_6$H$_4$C(CH$_3$)$_3$), 7.08-7.29 (13H, m, aromatic-H), 7.39-7.43 (2H, m, aromatic-H), 7.86 (1H, m, isoindolinone-H). $^{13}$C NMR (50 MHz, CDCl$_3$) δ 31.57 (—OCH$_2$C$_6$H$_4$C(CH$_3$)$_3$), 43.63 (—NCH$_2$C$_6$H$_5$), 64.88 (—OCH$_2$C$_6$H$_4$C(CH$_3$)$_3$), 95.89 (C-3), 123.35, 123.75, 125.23, 126.80, 127.35, 127.55, 128.38, 128.60, 129.67, 129.85, 132.02, 132.82, 134.59, 137.75, 138.82, 146.06, 150.65, 168.82 (C-1). MS (LC) m/z 147, 209, 298, 462 [MH$^+$], 484 [MNa$^+$].

2-Benzyl-3-phenyl-3-(2-pyridin-2-yl-ethoxy)-2,3-dihydro-isoindolin-1-one (NU8133)

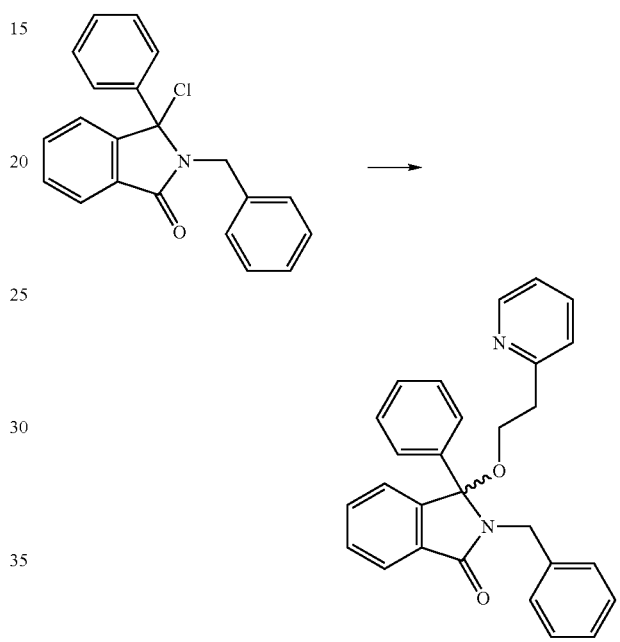

2-Benzyl-3-chloro-3-phenyl-2,3-dihydro-isoindolin-1-one (0.51 g, 1.50 mmol) was reacted with 2-(2-hydroxyethyl)pyridine (0.67 mL, 5.97 mmol) as for General Procedure G yielding 2-benzyl-3-phenyl-3-(2-pyridin-2-yl-ethoxy)-2,3-dihydro-isoindolin-1-one as a pink-orange oil. The crude product was purified by flash column chromatography (silica gel, 40:60 ethyl acetate:petrol) yielding 2-benzyl-3-phenyl-3-(2-pyridin-2-yl-ethoxy)-2,3-dihydro-isoindolin-1-one as a cloudy oil. This was dissolved in the minimum amount of boiling ethyl acetate and recrystallised by dropwise addition of petrol to give large white crystals (0.11 g, 0.26 mmol, 18%); $R_f$ 0.19 (40:60 ethyl acetate:petrol); mp 115-118° C.

Anal. Calcd for $C_{28}H_{24}N_2O_2$: C, 79.98; H, 5.75; N, 6.66%. Found: C, 79.66; H, 5.74; N, 6.71%. IR (Diamond ATR) $\upsilon_{max}$ (cm$^{-1}$): 1697 (CO), 1385, 1059, 758, 696. $^1$H NMR (200 MHz, CDCl$_3$) δ 1.98-2.65 (2H, m, —OCH$_2$CH$_2$—), 2.86-3.10 (2H, m, —OCH$_2$CH$_2$—), 3.84-3.91 (1H, d, J=14.5 Hz, —NCH$_2$C$_6$H$_5$), 4.61-4.68 (1H, d, J=14.5 Hz, —NCH$_2$C$_6$H$_5$), 6.85-6.90 (2H, m, pyridine-H$_5$+H$_3$), 6.99-7.24 (11H, m, aromatic-H), 7.28-7.42 (2H, m, aromatic-H), 7.45-7.54 (1H, m, pyridine-H$_4$), 7.79-7.83 (1H, m, isoindolinone-H), 8.37-8.39 (1H, m, pyridine-H$_6$). $^{13}$C NMR (50 MHz, CDCl$_3$) δ 37.87 (—OCH$_2$CH$_2$—), 43.11 (—NCH$_2$C$_6$H$_5$), 62.37 (—OCH$_2$CH$_2$—), 95.45 (C-3), 121.36, 123.12, 123.57, 126.44, 127.17, 128.20, 128.35, 128.42, 129.37, 129.56, 131.59, 132.57, 136.10, 137.94, 138.75, 145.58, 149.26, 158.92, 168.35 (C-1). MS (LC) m/z 298, 421 [MH⁺].

3-(3-Hydroxy-propoxy)-3-phenyl-2-propyl-2,3-dihydro-1H-isoindolin-1-one (NU8033)

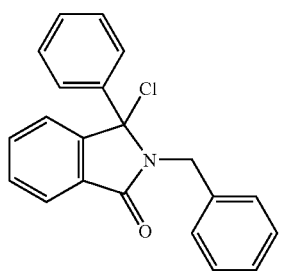

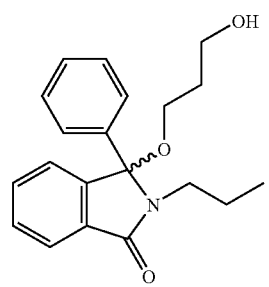

3-Chloro-3-phenyl-2-propyl-2,3-dihydro-isoindolin-1-one (0.53 g, 1.87 mmol) in THF (5 mL) was added dropwise to 1,3-propanediol (10 mL) and stirred at room temperature for 20 h. The solvent was removed under vacuum and the crude reaction mixture was taken up into ethyl acetate (2×20 mL) and washed with water (2×20 mL). The organic layer was collected and dried (Na$_2$SO$_4$). Removal of the solvent in vacuo yielded 3-(3-hydroxy-propoxy)-3-phenyl-2-propyl-2,3-dihydro-1H-isoindolin-1-one as a yellow oil. This was dissolved in the minimum amount of THF and recrystallised by dropwise addition of water to give a white solid (0.12 g, 0.37 mmol, 20%); R$_f$ 0.24 (40:60 ethyl acetate:petrol); mp 114-117° C.

Anal. Calcd for C$_{20}$H$_{23}$NO$_3$: C, 73.82; H, 7.12; N, 4.30%. Found: C, 73.60; H, 6.91; N, 4.08%. IR (KBr) $\upsilon_{max}$ (cm$^{-1}$): 3482 (OH), 1695 (CO). $^1$H NMR (200 MHz, d$_6$-DMSO) δ 0.78-0.93 (3H, t, J=7.5 Hz, —NCH$_2$CH$_2$CH$_3$), 1.28-1.60 (2H, m, —NCH$_2$CH$_2$CH$_3$), 1.71-1.91 (2H, m, —OCH$_2$CH$_2$CH$_2$OH), 2.91-3.14 (2H, m, —NCH$_2$CH$_2$CH$_3$), 3.17-3.37 (2H, m, —OCH$_2$CH$_2$CH$_2$OH), 3.53-3.70 (2H, m, —OCH$_2$CH$_2$CH$_2$OH), 4.55 (1H, s, —OCH$_2$CH$_2$CH$_2$OH, exchangeable with D$_2$O), 7.25-7.59 (6H, m, aromatic-H), 7.62-7.79 (2H, m, aromatic-H), 7.84-7.96 (1H, m, isoindolinone-H). $^{13}$C NMR (50 MHz, d$_6$-DMSO) δ 11.94 (—NCH$_2$CH$_2$CH$_3$), 21.42 (—NCH$_2$CH$_2$CH$_3$), 32.72 (—OCH$_2$CH$_2$CH$_2$OH), 38.61 (—NCH$_2$CH$_2$CH$_3$), 57.99 (—OCH$_2$CH$_2$CH$_2$OH), 59.81 (—OCH$_2$CH$_2$CH$_2$OH), 93.68 (C-3), 123.09, 123.41, 126.23, 128.74, 128.85, 130.15, 131.70, 133.03, 139.50, 145.67, 167.55 (C-1). MS (EI) m/z 325 [M⁺].

2-(2-Amino-ethyl)-3-hydroxy-3-phenyl-2,3-dihydro-isoindolin-1-one

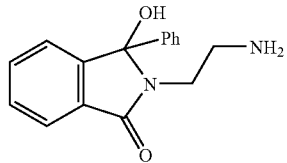

The title compound was prepared from 2-benzoyl benzoic acid 8 (0.75 g, 3.3 mmol), and redistilled ethylenediamine (2.21 mL, 33 mmol), according to general procedure A. The crude compound was crystallised from petrol to afford a white powder (0.71 g, 2.64 mmol) in 80% yield. Mp: 145-147° C.

Anal. Calc for C$_{16}$H$_{16}$N$_2$O$_2$: C, 71.62; H, 6.01; N, 10.44%; Found C, 71.06; H, 5.70; N, 9.56%. FT-IR ν (cm$^{-1}$): 3321 (NH$_2$), 1684 (C═O). $^1$H NMR (300 MHz, CDCl$_3$) δ$_H$ (ppm): 2.58 (1H, td, J$_{H-H}$=12.23 and 11.89 Hz, CH$_2$), 2.79 (1H, td, J$_{H-H}$=13.05 and 11.62 Hz, CH$_2$), 2.95 (1H, dd, J$_{H-H}$=12.91 and 10.17 Hz, CH$_2$), 4.10 (1H, dd, J$_{H-H}$=14.67 and 7.14 Hz, CH$_2$), 6.95 (1H, bs, NH$_2$), 7.17-7.47 (8H, m, Ar—H), 7.76 (1H, dd, J$_{H-H}$=6.6 Hz, H$_4$). $^{13}$C NMR (75 MHz, CDCl$_3$) δ$_C$ (ppm): 40.7 (CH$_2$), 42 (CH$_2$), 90.3 (N—C—O), 122.9-150.3 (C—Ar), 168.7 (C═O). LC-MS (ES⁺, MeOH): m/e=269 (MH⁺), 251, 208, Rt=3.0 min.

N-[2-(1-Hydroxy-3-oxo-1-phenyl-1,3-dihydro-isoindolin-2-yl)-ethyl]-acetamide

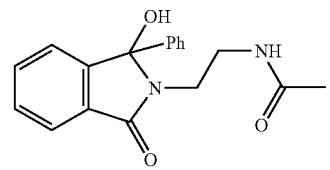

2-(2-Amino-ethyl)-3-hydroxy-3-phenyl-2,3-dihydro-isoindolin-1-one (0.20 g, 0.75 mmol) was suspended in acetic anhydride (1.2 mL), the mixture was heated at reflux for 15 min. When the reaction was complete by TLC (MeOH/DCM 1:9), the mixture was cooled to room temperature, where water was added (12 mL). The white suspension was re-heated at reflux. After 15 more minutes, the suspension was filtered. Then extracted with DCM (3×10 mL) and water (10 mL). The organic layers were combined, dried over sodium sulphate, filtered and solvent removed in vacuo. The crude product was purified by crystallisation from petrol and DCM, affording quantitatively the desired product (0.24 g, 0.77 mmol) as a white solid. Rf: 0.38 (MeOH/DCM 1:9). Mp: 165° C.

Anal. Calc for C$_{18}$H$_{18}$N$_2$O$_3$: C, 70.35; H, 6.21; N, 8.64%; Found C, 67.01; H, 5.60; N, 8.46%. FT-IR ν (cm$^{-1}$): 3379 (NH), 1697 (C═O). $^1$H NMR (300 MHz, CDCl$_3$) δ$_H$ (Ppm): 1.87 (3H, s, CH$_3$), 2.97 (2H, m, CH$_2$), 3.98 (1H, m, CH$_2$), 4.22 (1H, m, CH$_2$), 6.34 (1H, bs, NH), 7.28-7.50 (8H, m, Ar—H), 7.74 (1H, dd, J$_{H-H}$=0.91 Hz, H$_4$). $^{13}$C NMR (75 MHz, CDCl$_3$) δ$_C$ (ppm): 23 (CH$_3$), 39.2 (CH$_2$), 40.8 (CH$_2$), 92.3 (OCN), 123.3-150.3 (C—Ar), 169.2 (C═O), 173.2 (C═O). LC-MS (ES+, MeOH): m/e=333 (MH+23), 293, 208, Rt=5.67 min

N-{2-[1-(4-t-Butyl-benzyloxy)-3-oxo-1-phenyl-1,3-dihydro-isoindolin-2-yl]-ethyl}-acetamide (NU8213)

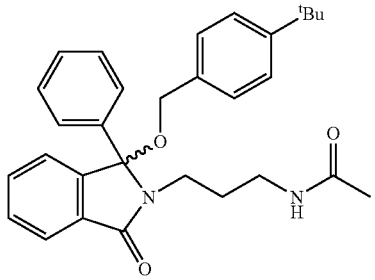

A solution of N-[2-(1-Hydroxy-3-oxo-1-phenyl-1,3-dihydro-isoindolin-2-yl)-ethyl]-acetamide (0.13 g, 0.42 mmol) in THF (10 mL) was treated with thionyl chloride (2.2 equivalent), and a catalytic amount of DMF. After 16 h, the reaction mixture was evaporated in vacuo. The crude chloro product was dissolved in THF (8 mL), then were successively added 4-t-butylbenzyl alcohol (0.08 mL, 0.46 mmol), and triethylamine (0.13 mL, 0.92 mmol) in THF (6 mL). The mixture was stirred under a nitrogen atmosphere, and monitored by TLC (MeOH/DCM 1:9). After completion, the solvent was removed in vacuo. The crude product was extracted with ethyl acetate and water. The combined organic layer was washed with saturated aqueous sodium bicarbonate. The organic layer was dried over sodium sulphate, filtered, and the solvent removed. The crude product (0.02 g, 0.04 mmol) was purified by column chromatography (DCM 100%) affording NU8213 as a green oil in 8%. Rf: 0.45 (MeOH/DCM 1:9). UV $\lambda_{max}$=231 nm. Mp: 187-188° C.

Anal. Calc. for $C_{30}H_{31}N_2O_3$: C, 76.29; H, 7.06; N, 6.14%. Found C, 71.41; H, 6.49; N, 5.17%. FT-IR ν (cm−1): 3309 (NH), 1685 (C═O amide). $^1$H NMR (300 MHz, CDCl$_3$) δH (ppm): 1.25 (9H, s, t-Bu), 1.8 (3H, s, CH$_3$), 3 (1H, m, CH$_{2\,dia}$), 3.3 (2H, m, NCH$_{2\,dia}$), 3.45 (1H, m, NCH$_{2dia}$), 3.9 (1H, d, $J_{H-H}$=10.72 Hz, OCH$_{2dia}$), 4 (1H, d, $J_{H-H}$=11.13 Hz, OCH$_{2dia}$),), 6.7 (1H, bs, NH), 7.12-7.48 (12H, m, Ar—H), 7.87 (1H, m, Ar—H$_4$). $^{13}$C NMR (125 MHz, CDCl3) δC (ppm): 22.6 (CH$_3$), 31.31 (3×CH$_3$), 38.78 (CH$_2$), 39.2 (CH$_2$), 64.9 (CH$_2$), 95.4 (NCO), 122.8-151 (CH—Ar), 170 (C═O), 170.2 (C═O). LC-MS (ES+, MeOH): m/e=479, (MH+23), 294, 209, 149, 91 Rt=7.50 min.

3-Chloro-3-(4-chlorophenyl)-3H-isobenzofuran-1-one

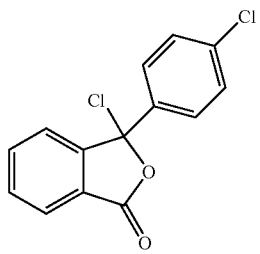

Distilled THF (25 mL) was added to 2-(4-chlorobenzoyl) benzoic acid (1 g, 3.8 mmol) followed by thionyl chloride (0.55 mL, 7.6 mmol) and a catalytic amount of DMF (3 drops). The system was stirred under nitrogen for 4 h at room temperature and monitored by TLC. Removal of the solvent gave 3-chloro-3-(4-chlorophenyl)-3H-isobenzofuran-1-one as a colourless oil (1.06 g, 3.8 mmol, 100%).

2-Benzyl-3-(4-chlorophenyl)-3-hydroxy-2,3-dihydroisoindolin-1-one

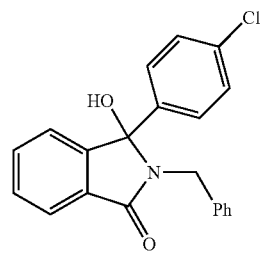

Distilled THF (25 mL) was added to 3-chloro-3-(4-chlorophenyl)-3H-isobenzofuran-1-one (1.06 g, 3.8 mmol) followed by benzylamine (0.62 mL, 5.7 mmol) and triethylamine (1.06 mL, 7.6 mmol) as for general procedure D. The crude product was recrystallised in the minimum amount of boiling ethyl acetate to give 2-benzyl-3-(4-chlorophenyl)-3-hydroxy-2,3-dihydroisoindolin-1-one$^2$ as a white solid (965 mg, 2.76 mmol, 72%); R$_f$ 0.62 (40:60 EtOAc:petrol). mp 187.9-189.7° C. $^1$H NMR: (300 MHz, CDCl$_3$) δ 3.65 (s, 1H, OH), 4.03 (d, 1H, J=14.9 Hz, N—CH$_2$), 4.44 (d, 1H, J=14.9 Hz, N—CH$_2$), 7.01-7.18 (m, NU8224, Ar—H), 7.31 (m, 2H, Ar—H), 7.66 (m, 1H, Ar—H). $^{13}$C NMR: (75 MHz, CDCl$_3$) δ 43.2, 91.5, 123, 123.9, 127.4, 128.2, 128.5, 128.8, 129, 130.1, 130.4, 133.3, 134.7, 137.1, 138.1, 149, 168.2. LC/MS-ES+ m/z 332, 350.1 [MH+], 372.1 [MNa+].

2-Benzyl-3-chloro-3-(4-chlorophenyl)-2,3-dihydroisoindolin-1-one

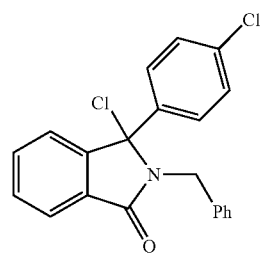

2-Benzyl-3-(4-chlorophenyl)-3-hydroxy-2,3-dihydroisoindolin-1-one (200 mg, 0.57 mmol) was reacted with thionyl chloride (0.13 mL, 1.14 mmol) and a catalytic amount of DMF (3 drops) as for general procedure B. Removal of the solvent gave 2-benzyl-3-chloro-3-(4-chlorophenyl)-2,3-dihydroisoindolin-1-one as a colourless oil (209 mg, 0.57 mmol, 100%).

2-Benzyl-3-(4-tert-butylbenzyloxy)-3-(4-chlorophenyl)-2,3-dihydroisoindolin-1-one (NU8220)

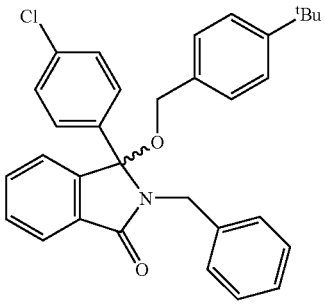

2-Benzyl-3-chloro-3-(4-chlorophenyl)-2,3-dihydroisoindolin-1-one (209 mg, 0.57 mmol) was reacted with 4-tert-butylbenzyl alcohol (0.1 mL, 0.57 mmol) and potassium carbonate (86 mg, 0.63 mmol) as for general procedure F. The crude product was purified by flash column chromatography (10:90 EtOAc:petrol) to give 2-benzyl-3-(4-tert-butylbenzyloxy)-3-(4-chlorophenyl)-2,3-dihydroisoindolin-1-one as a colourless oil (201 mg, 0.4 mmol, 71%); $R_f$ 0.4 (15:85 EtOAc:petrol). $\lambda_{max}$ (CH$_3$OH)/nm 213.5, Abs 0.914. IR: 2947, 1692, 1465, 1357 cm$^{-1}$. $^1$H NMR: (300 MHz, CDCl$_3$) δ 1.22 (s, 9H, t-Bu), 3.63 (d, 1H, J=10.8 Hz, O—CH$_2$), 3.68 (d, 1H, J=10.9 Hz, O—CH$_2$), 4.08 (d, 1H, J=14.6 Hz, N—CH$_2$), 4.62 (d, 1H, J=14.6 Hz, N—CH$_2$), 6.83 (d, 2H, J=8.3 Hz, Ar—H), 7.07 (m, 6H, Ar—H), 7.20 (m, 6H, Ar—H), 7.42 (m, 2H, Ar—H), 7.88 (m, 1H, Ar—H). $^{13}$C NMR: (75 MHz, CDCl$_3$) δ31.7, 34.9, 43.6, 65.1, 95.5, 123.4, 124.1, 125.4, 127.6, 127.7, 128.5, 128.6, 128.8, 129.7, 130.2, 132.1, 133.1, 134.4, 134.7, 137.6, 137.7, 145.7, 151.0, 168.6. LC/MS-ES$^+$ m/z 332, 334, 496.2, 498.2. Anal. Calcd. for C$_{32}$H$_{30}$ClNO$_2$: C, 77.48; H, 6.10; N, 2.82%. Found C, 77.29; H, 6.07; N, 2.36%.

2-Benzyl-3-(4-chlorophenyl)-3-(4-hydroxy-3,5-dimethoxybenzyloxy)-2,3-dihydroisoindolin-1-one (NU8230)

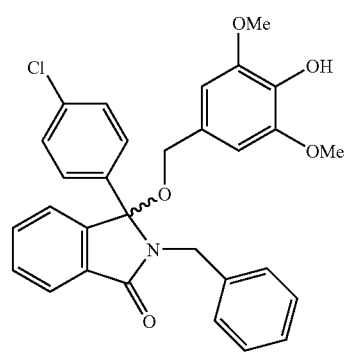

2-Benzyl-3-(4-chlorophenyl)-3-hydroxy-2,3-dihydroisoindolin-1-one (250 mg, 0.72 mmol) was reacted with thionyl chloride (0.0625 mL, 0.85 mmol) and a catalytic amount of DMF (3 drops) as for general procedure B. Removal of the solvent gave 2-benzyl-3-chloro-3-(4-chlorophenyl)-2,3-dihydroisoindolin-1-one as a colourless oil (262 mg, 0.72 mmol, 100%).

2-Benzyl-3-chloro-3-(4-chlorophenyl)-2,3-dihydroisoindolin-1-one (262 mg, 0.72 mmol) was reacted with syringic alcohol (289 mg, 1.57 mmol) as for general procedure F. The crude product was purified by flash column chromatography (45:55 EtOAc:petrol) to give 2-benzyl-3-(4-chlorophenyl)-3-(4-hydroxy-3,5-dimethoxybenzyloxy)-2,3-dihydroisoindolin-1-one as a light pink oil (277 mg, 0.53 mmol, 75%); $R_f$ 0.54 (45:55 EtOAc:petrol). $\lambda_{max}$ (CH$_3$OH)/nm 210.5, Abs 0.652. IR: 3391, 2936, 1689, 1610, 1354 cm$^{-1}$. $^1$H NMR: (300 MHz, CDCl$_3$) δ 3.57 (d, 1H, J=10.7 Hz, O—CH$_2$), 3.62 (d, 1H, J=10.7 Hz, O—CH$_2$), 3.74 (s, 6H, OMe), 4.07 (d, 1H, J=14.7 Hz, N—CH$_2$), 4.68 (d, 1H, J=14.7 Hz, N—CH$_2$), 5.50 (s, 1H, OH), 6.05 (s, 2H, Ar—H), 7.00-7.24 (m, NU8224, Ar—H), 7.43 (m, 2H, Ar—H), 7.88 (m, 1H, Ar—H). $^{13}$C NMR: (75 MHz, CDCl$_3$) δ 43.6, 56.8, 65.8, 95.6, 105.2, 123.4, 124.1, 127.5, 128.2, 128.4, 128.5, 128.7, 129, 129.7, 130.2, 132, 133.1, 134.7, 134.8, 137.5, 145.7, 147.1, 168.6. LC/MS-ES$^+$ m/z 350, 371.9, 515.9 [M$^+$], 517.9, 538 [MNa$^+$], 539.9. Anal. Calcd. for C$_{30}$H$_{26}$ClNO$_5$: C, 69.83; H, 5.08; N, 2.71%. Found C, 69.43; H, 5.12; N, 2.25%.

2-Benzyl-3-benzylsulphanyl-3-(4-chlorophenyl)-2,3-dihydro-isoindolin-1-one (NU8160)

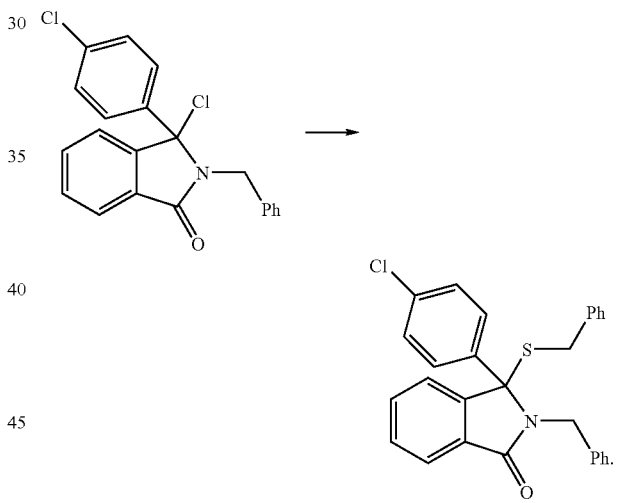

Dry THF (20 mL) was added to 2-benzyl-3-chloro-3-(4-chlorophenyl)-2,3-dihydro-isoindolin-1-one (3.22 g, 9.10 mmol) followed by benzyl mercaptan (2.36 mL, 20.02 mmol). The reaction mixture was stirred at room temperature for 48 h. Removal of the solvent under vacuum yielded a white oil. This was taken up into ethyl acetate (50 mL) and washed with water (2×30 mL). The organic layer was collected and dried (Na$_2$SO$_4$). Removal of the solvent in vacuo yielded 2-benzyl-3-benzylsulphanyl-3-(4-chlorophenyl)-2,3-dihydro-isoindolin-1-one as a white oil. The crude product was purified by flash column chromatography (silica gel, 10:90 ethyl acetate:petrol) to give a cream solid. This was dissolved in the minimum amount of boiling ethyl acetate and recrystallised by dropwise addition of petrol to yield a white crystalline solid (2.42 g, 5.30 mmol, 58%); $R_f$ 0.21 (10:90 ethyl acetate:petrol); mp 132-135° C. Anal. Calcd for C$_{28}$H$_{22}$ClNOS: C, 73.75; H, 4.86; N, 3.07%. Found: C, 73.91; H, 4.89; N, 2.73%. $^1$H NMR (300 MHz, CDCl$_3$) δ

2.61-2.65 (1H, d, J=11.5 Hz, —SCH$_2$C$_6$H$_5$), 2.76-2.80 (1H, d, J=11.5 Hz, —SCH$_2$C$_6$H$_5$), 4.33-4.38 (1H, d, J=15.0 Hz, —NCH$_2$C$_6$H$_5$), 4.69-4.74 (1H, d, J=15.0 Hz, —NCH$_2$C$_6$H$_5$), 6.66-6.69 (2H, m, —C$_6$H$_4$Cl), 7.04-7.38 (13H, m, aromatic-H), 7.40-7.48 (2H, m, aromatic-H), 7.84-7.87 (1H, m, isoindolinone-H). $^{13}$C NMR (300 MHz, CDCl$_3$) δ 33.33 (—SCH$_2$C$_6$H$_5$), 43.99 (—NCH$_2$C$_6$H$_5$), 78.47 (C-3), 123.24, 123.53, 127.24, 128.04, 128.16, 128.42, 128.75, 129.03, 129.52, 130.58, 133.08, 134.73, 135.45, 136.58, 137.61, 148.69, 168.49 (C-1). MS (LC) m/z 456 [M$^+$].

2-Benzyl-3-(4-chlorophenyl)-3-(3-hydroxy-propoxy)-2,3-dihydro-isoindolin-1-one (NU8165)

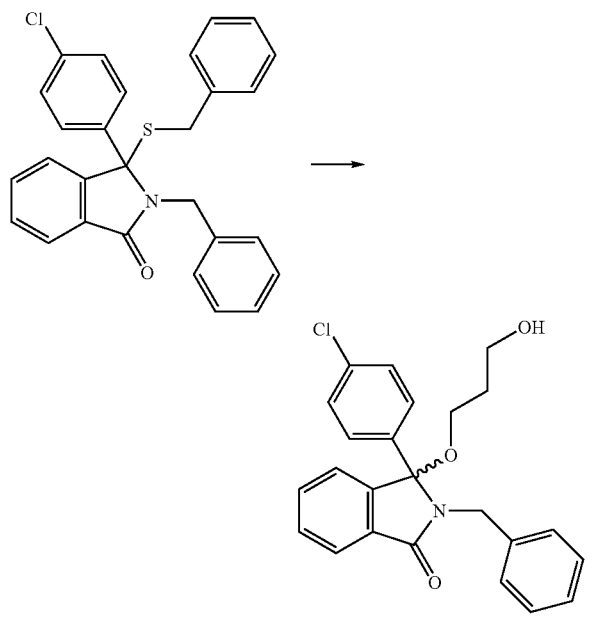

2-Benzyl-3-benzylsulphanyl-3-(4-chlorophenyl)-2,3-dihydro-isoindolin-1-one (0.50 g, 1.10 mmol) in THF (4 mL) was added to a solution of NIS (0.27 g, 1.21 mmol), CSA (0.03 g) and propane-1,3-diol (0.17 mL, 2.35 mmol) in THF (3 mL) as for General Procedure J yielding 2-benzyl-3-(4-chloro-phenyl)-3-(3-hydroxy-propoxy)-2,3-dihydro-isoindolin-1-one as an orange oil. The crude product was purified by flash column chromatography (silica gel, 40:60 ethyl acetate:petrol) to give a yellow oil. This was dissolved in the minimum amount of boiling ethyl acetate and recrystallised by dropwise addition of petrol giving a fluffy white solid (0.17 g, 0.42 mmol, 39%); R$_f$ 0.32 (40:60 ethyl acetate: petrol); mp 149-151° C.

Anal. Calcd for C$_{24}$H$_{22}$ClNO$_3$: C, 70.67; H, 5.44; N, 3.43%. Found: C, 70.34; H, 5.33; N, 3.45%. IR (Diamond ATR) υ$_{max}$ (cm$^{-1}$): 3431 (OH), 1669 (CO), 1426, 1399, 1359, 1066, 1012, 818, 766, 700. $^1$H NMR (300 MHz, CDCl$_3$) δ 1.21-1.43 (2H, m, —OCH$_2$CH$_2$CH$_2$OH), 1.53 (broad s, —OCH$_2$CH$_2$CH$_2$OH, exchangeable with D$_2$O), 2.69-2.74 (2H, m, —OCH$_2$CH$_2$CH$_2$OH), 3.40-3.44 (2H, m, —OCH$_2$CH$_2$CH$_2$OH), 3.89-3.94 (1H, d, J=14.5 Hz, —NCH$_2$C$_6$H$_5$), 4.69-4.74 (1H, d, J=14.5 Hz, —NCH$_2$C$_6$H$_5$), 7.01-7.10 (1H, m, aromatic-H), 7.12-7.23 (9H, m, aromatic-h), 7.40-7.46 (2H, m, aromatic-H), 7.82-7.88 (1H, m, isoindolinone-H). $^{13}$C NMR (300 MHz, CDCl$_3$) δ 32.02 (—OCH$_2$CH$_2$CH$_2$OH), 43.35 (—NCH$_2$C$_6$H$_5$), 60.70 and 60.83 (—OCH$_2$CH$_2$CH$_2$OH), 95.38 (C-3), 123.11, 124.04, 127.58, 128.16, 128.53, 128.96, 129.55, 130.15, 131.81, 133.08, 134.73, 137.50, 137.89, 145.51, 165.76 (C-1). MS (LC) m/z 332, 334, 408 [M$^+$].

2-Benzyl-3-(4-chlorophenyl)-3-(2-pyridin-2-yl-ethoxy)-2,3-dihydro-1H-isoindolin-1-one (NU8170)

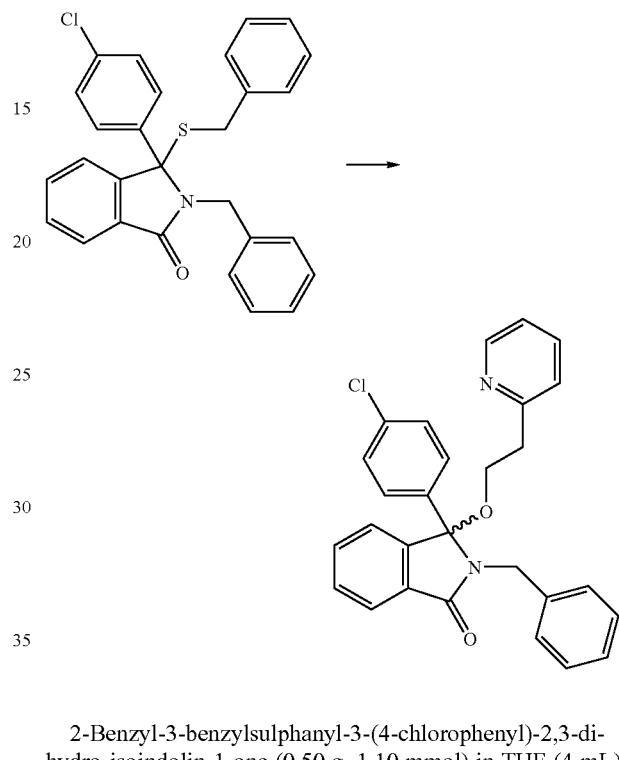

2-Benzyl-3-benzylsulphanyl-3-(4-chlorophenyl)-2,3-dihydro-isoindolin-1-one (0.50 g, 1.10 mmol) in THF (4 mL) was added to a solution of NIS (0.27 g, 1.21 mmol), CSA (0.03 g) and 2-(2-hydroxy-ethyl)-pyridine (0.27 mL, 2.41 mmol) in THF (3 mL) as for General Procedure J yielding 2-benzyl-3-(4-chlorophenyl)-3-(2-pyridin-2-yl-ethoxy)-2,3-dihydro-1H-isoindolin-1-one as an orange oil. The crude product was purified by flash column chromatography (silica gel, 45:55 ethyl acetate:petrol) to give a yellow oil. This was dissolved in the minimum amount of boiling ethyl acetate and recrystallised by dropwise addition of petrol yielding an off-white solid (0.16 g, 0.36 mmol, 32%); R$_f$ 0.27 (45:55 ethyl acetate:petrol); mp 130-132° C.

Anal. Calcd for C$_{28}$H$_{23}$ClN$_2$O$_2$: C, 73.92; H, 5.10; N, 6.16%. Found: C, 73.78; H, 5.10; N, 5.97%. IR (Diamond ATR) υ$_{max}$ (cm$^{-1}$): 1694 (CO), 1591, 1468, 1380, 1353, 1263, 1068, 1012, 823, 761, 701. $^1$H NMR (300 MHz, CDCl$_3$) δ 2.40-2.49 (1H, m, —OCH$_2$CH$_2$-pyr), 2.56-2.65 (1H, m, —OCH$_2$CH$_2$-pyr), 2.92-3.08 (2H, m, —OCH$_2$CH$_2$-pyr), 3.91-3.98 (1H, d, J=14.5 Hz, —CH$_2$C$_6$H$_5$), 4.49-4.54 (1H, d, J=14.5 Hz, —CH$_2$C$_6$H$_5$), 6.82-6.90 (2H, m, aromatic-H), 7.01-7.19 (NU8224, m, aromatic-H), 7.32-7.42 (2H, m, aromatic-H), 7.47-7.53 (1H, m, aromatic-H), 7.79-7.83 (1H, m, isoindolinone-H), 8.38-8.40 (1H, m, pyridine-H$_6$). $^{13}$C NMR (300 MHz, CDCl$_3$) δ 38.17 (—OCH$_2$CH$_2$-pyr), 43.31 (—NCH$_2$C$_6$H$_5$), 62.77 (—OCH$_2$CH$_2$-pyr), 95.24 (C-3), 121.79, 123.34, 123.92, 124.03, 127.59, 128.30, 128.58, 128.87, 129.65, 130.15, 131.84, 133.05, 134.62, 136.51, 137.71, 138.08, 145.48, 149.63, 159.12 (pyridine-C$_2$), 168.53 (C-1). MS (LC) m/z 332, 333, 334.

3-(4-Chlorophenyl)-3-hydroxy-2-propyl-2,3-dihydroisoindolin-1-one

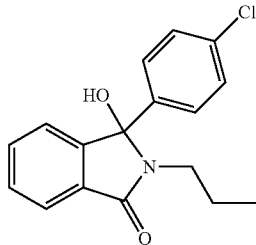

Distilled THF (25 mL) was added to 3-chloro-3-(4-chlorophenyl)-3H-isobenzofuran-1-one (1.6 g, 5.75 mmol) followed by n-propylamine (0.52 mL, 6.33 mmol) and triethylamine (0.96 mL, 6.9 mmol) as for general procedure A. The crude product was recrystallised in the minimum amount of boiling ethyl acetate to give 3-(4-Chlorophenyl)-3-hydroxy-2-propyl-2,3-dihydroisoindolin-1-one as a white solid[2] (1.32 g, 4.37 mmol, 76%); R$_f$ 0.72 (70:30 EtOAc:petrol). mp 201.6-202.8° C. $^1$H NMR: (300 MHz, CDCl$_3$) δ 0.72 (t, 3H, J=7.3 Hz, CH$_2$—CH$_2$—CH$_3$), 1.28 (m, 1H, N—CH$_2$—CH$_2$), 1.39 (m, 1H, N—CH$_2$—CH$_2$), 2.79 (m, 1H, N—CH$_2$), 3.25 (m, 1H, N—CH$_2$), 3.61 (s, 1H, OH), 7.17 (m, 1H, Ar—H), 7.24 (m, 4H, Ar—H), 7.37 (m, 2H, Ar—H), 7.58 (m, 1H, Ar—H). $^{13}$C NMR: (75 MHz, CDCl$_3$) δ 12, 22.4, 41.6, 91.3, 22.9, 123.7, 128.1, 129, 130, 130.8, 133, 134.8, 137.7, 148.9, 168. LC/MS-ES$^+$ m/z 242.9, 302.1 [MH$^+$].

3-Chloro-3-(4-chlorophenyl)-2-propyl-2,3-dihydroisoindolin-1-one

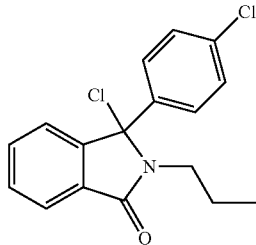

3-(4-Chlorophenyl)-3-hydroxy-2-propyl-2,3-dihydroisoindolin-1-one (250 mg, 0.82 mmol) was reacted with thionyl chloride (0.12 mL, 1.65 mmol) and a catalytic amount of DMF (3 drops) as for general procedure B. Removal of the solvent gave 3-chloro-3-(4-chlorophenyl)-2-propyl-2,3-dihydroisoindolin-1-one as a colourless oil (262 mg, 0.82 mmol, 100%).

3-(4-tert-Butyl-benzyloxy)-3-(4-chlorophenyl)-2-propyl-2,3-dihydroisoindolin-1-one (NU8221)

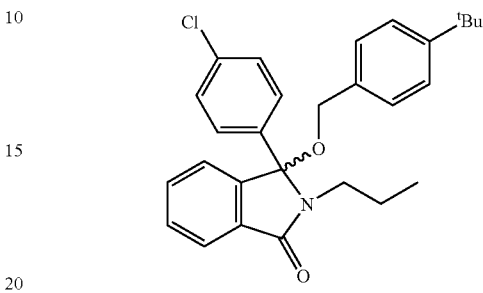

3-Chloro-3-(4-chlorophenyl)-2-propyl-2,3-dihydroisoindolin-1-one (262 mg, 0.82 mmol) was reacted with 4-tert-butylbenzyl alcohol (0.15 mL, 0.82 mmol) and potassium carbonate (124 mg, 0.9 mmol) as for general procedure F. The crude product was purified by flash column chromatography (20:80 EtOAc:petrol) to give 3-(4-tert-butyl-benzyloxy)-3-(4-chlorophenyl)-2-propyl-2,3-dihydroisoindolin-1-one as a white solid (325 mg, 0.72 mmol, 88%); R$_f$ 0.48 (20:80 EtOAc:petrol). mp 116.5-117.6° C. λ$_{max}$ (CH$_3$OH)/nm 219.5, Abs 0.804. IR: 2947, 1689, 1467, 1372 cm$^{-1}$. $^1$H NMR: (300 MHz, CDCl$_3$) δ 0.73 (t, 3H, J=7.4 Hz, CH$_2$—CH$_2$—CH$_3$), 1.25 (s, 9H, t-Bu), 1.30 (m, 1H, N—CH$_2$—CH$_2$), 1.45 (m, 1H, N—CH$_2$—CH$_2$), 3.03 (m, 1H, N—CH$_2$), 3.22 (m, 1H, N—CH$_2$), 3.87 (d, 1H, J=11.1 Hz, O—CH$_2$), 4.13 (d, 1H, J=11.1 Hz, O—CH$_2$), 7.06 (m, 1H, Ar—H), 7.19 (m, 4H, Ar—H), 7.29 (m, 4H, Ar—H), 7.42 (m, 2H, Ar—H), 7.83 (m, 1H, Ar—H). $^{13}$C NMR: (75 MHz, CDCl$_3$) δ 12.2, 21.9, 31.7, 34.9, 41.8, 64.9, 95.1, 123.4, 123.8, 125.7, 127.5, 128.3, 128.9, 130.2, 132.3, 132.9, 134.6, 134.7, 138.145.6, 151.1, 168.6. LC/MS-ES$^+$ m/z 284, 448.1, 470.2, 507.2. Anal. Calcd. for C$_{28}$H$_{30}$ClNO$_2$: C, 75.07; H, 6.75; N, 3.13%. Found C, 75.29; H, 6.97; N, 2.89%.

3-(4-Chlorophenyl)-3-(3-hydroxypropoxy)-2-propyl-2,3-dihydroisoindolin-1-one (NU8222)

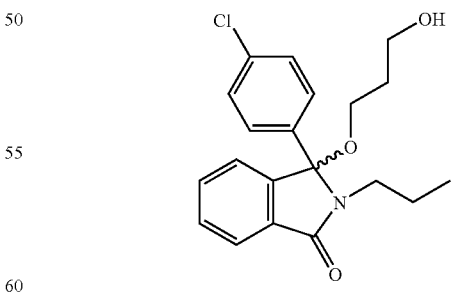

3-Chloro-3-(4-chlorophenyl)-2-propyl-2,3-dihydroisoindolin-1-one (262 mg, 0.82 mmol) was reacted with 1,3-propanediol (0.41 mL, 5.74 mmol) as for general procedure F. The crude product was purified by flash column chromatography (40:60 EtOAc:petrol) to give 3-(4-chlorophenyl)-3-(3-hydroxypropoxy)-2-propyl-2,3-dihydroisoindolin-1-one as a colourless oil (241 mg, 0.66 mmol, 81%); $R_f$ 0.3 (40:60 EtOAc:petrol). $\lambda_{max}$ (CH$_3$OH)/nm 223, Abs 0.818. IR: 3403, 2933, 1684, 1458 cm$^{-1}$. $^1$H NMR: (300 MHz, CDCl$_3$) δ 0.77 (t, 3H, J=7.4 Hz, CH$_2$—CH$_2$—CH$_3$), 1.27 (m, 1H, N—CH$_2$—CH$_2$), 1.42 (m, 1H, N—CH$_2$—CH$_2$), 1.78 (m, 2H, O—CH$_2$—CH$_2$—CH$_2$—OH), 2.95 (m, 1H, O—CH$_2$), 3.01 (m, 1H, N—CH$_2$), 3.16 (m, 1H, N—CH$_2$), 3.23 (m, 1H, O—CH$_2$), 3.72 (t, 2H, J=6.1 Hz, O—CH$_2$—CH$_2$—CH$_2$—OH), 7.05 (m, 1H, Ar—H), 7.21 (m, 4H, Ar—H), 7.43 (m, 2H, Ar—H), 7.79 (m, 1H, Ar—H). $^{13}$C NMR: (75 MHz, CDCl$_3$) δ 12.1, 21.9, 32.5, 41.7, 53.8, 60.8, 61, 95, 123.2, 123.8, 128.1, 129.1, 130.2, 132.3, 132.9, 134.8, 138.1, 145.5, 168.6. LC/MS-ES$^+$ m/z 284.1, 316.1, 360.1 [MH$^+$], 382.1 [MNa$^+$]. Anal. Calcd. for C$_{20}$H$_{22}$ClNO$_3$: C, 66.75; H, 6.16; N, 3.89%. Found C, 66.45; H, 6.43; N, 3.75%.

3-(4-Chlorophenyl)-2-propyl-3-(2-pyridin-2-yl-ethoxy)-2,3-dihydroisoindolin-1-one (NU8229)

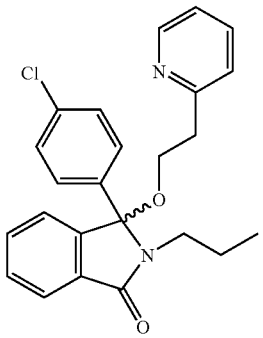

3-Chloro-3-(4-chlorophenyl)-2-propyl-2,3-dihydroisoindolin-1-one (262 mg, 0.82 mmol) was reacted with 2-(2-hydroxyethyl)pyridine (0.09 mL, 0.82 mmol) and potassium carbonate (124 mg, 0.9 mmol) as for general procedure F. The crude product was purified by flash column chromatography (40:60 EtOAc:petrol) to give 3-(4-chlorophenyl)-2-propyl-3-(2-pyridin-2-yl-ethoxy)-2,3-dihydroisoindolin-1-one as a clear yellow oil (187 mg, 0.45 mmol, 56%); $R_f$ 0.35 (40:60 EtOAc:petrol). $\lambda_{max}$ (CH$_3$OH)/nm 228, Abs 0.455. IR: 2931, 1689, 1591, 1458 cm$^{-1}$. $^1$H NMR: (300 MHz, CDCl$_3$) δ 0.65 (t, 3H, J=7.4 Hz, CH$_2$—CH$_2$—CH$_3$), 1.16 (m, 1H, N—CH$_2$—CH$_2$), 1.32 (m, 1H, N—CH$_2$—CH$_2$), 2.87 (m, 1H, N—CH$_2$), 2.92-3.03 (m, 2H, Pyr-CH$_2$, and m, 1H, N—CH$_2$), 3.20 (m, 1H, O—CH$_2$), 3.44 (m, 1H, O—CH$_2$), 6.84 (m, 1H, Ar—H), 7.05 (m, 1H, Ar—H), 7.11-7.20 (m, 5H, Ar—H), 7.35 (m, 2H, Ar—H), 7.53 (td, 1H, J=7.7, 1.8 Hz, Ar—H), 7.75 (m, 1H, Ar—H), 8.42 (m, 1H, Ar—H). $^{13}$C NMR: (75 MHz, CDCl$_3$) δ 12.1, 21.8, 38.7, 41.6, 62.7, 94.8, 121.8, 123.2, 123.7, 124, 128.1, 128.8, 130.1, 132.2, 132.7, 134.6, 136.5, 138.2, 145.4, 149.7, 159.1, 168.5. LC/MS-ES$^+$ m/z 284.1, 286, 407 [MH$^+$]. Anal. Calcd. for C$_{24}$H$_{23}$ClN$_2$O$_2$.0.25EtOAc: C, 70.00; H, 5.87; N, 6.88%. Found C, 69.48; H, 5.66; N, 6.86%.

3-(4-Chlorophenyl)-3-(4-hydroxy-3,5-dimethoxybenzyloxy)-2-propyl-2,3-dihydroisoindolin-1-one (NU8231)

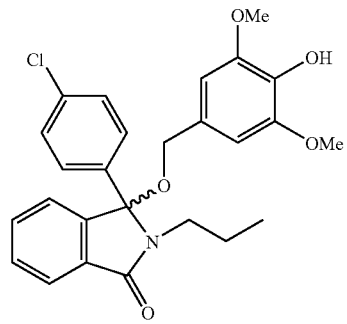

3-(4-Chlorophenyl)-3-hydroxy-2-propyl-2,3-dihydroisoindolin-1-one (250 mg, 0.82 mmol) was reacted with thionyl chloride (0.072 mL, 0.06 mmol) and a catalytic amount of DMF (3 drops) as for general procedure B. Removal of the solvent gave 3-chloro-3-(4-chlorophenyl)-2-propyl-2,3-dihydroisoindolin-1-one as a colourless oil (262 mg, 0.82 mmol, 100%).

3-Chloro-3-(4-chlorophenyl)-2-propyl-2,3-dihydroisoindolin-1-one (262 mg, 0.82 mmol) was reacted with syringic alcohol (331 mg, 1.80 mmol) as for general procedure F1. The crude product was purified by flash column chromatography (45:55 EtOAc:petrol) and HPLC(H$_2$O:CH$_3$CN, 270 nm) to give 3-(4-chlorophenyl)-3-(4-hydroxy-3,5-dimethoxybenzyloxy)-2-propyl-2,3-dihydroisoindolin-1-one as an opaque light red oil (180 mg, 0.38 mmol, 46%); $R_f$ 0.36 (45:55 EtOAc:petrol). $\lambda_{max}$ (CH$_3$OH)/nm 209, Abs 0.550. IR: 3360, 2933, 1692, 1604, 1504, 1450 cm$^{-1}$. $^1$H NMR: (300 MHz, CDCl$_3$) δ 0.74 (t, 3H, J=7.4 Hz, CH$_2$—CH$_2$—CH$_3$), 1.31 (m, 1H, N—CH$_2$—CH$_2$), 1.44 (m, 1H, N—CH$_2$—CH$_2$), 3.03 (m, 1H, N—CH$_2$), 3.23, (m, 1H, N—CH$_2$), 3.79 (s, 6H, OMe), 3.84 (d, 1H, J=11.1 Hz, O—CH$_2$), 4.08 (d, 1H, J=11.2 Hz, O—CH$_2$), 5.45 (s, 1H, OH), 6.38 (s, 2H, Ar—H), 7.05 (m, 1H, Ar—H), 7.22 (d, 2H, J=8.9 Hz, Ar—H), 7.28 (d, 2H, J=8.7 Hz, Ar—H), 7.42 (m, 2H, Ar—H), 7.83 (m, 1H, Ar—H). $^{13}$C NMR: (75 MHz, CDCl$_3$) δ 12.1, 22.1, 41.9, 56.7, 65.6, 95.1, 104.8, 123.5, 123.8, 128.2, 128.7, 129.1, 130.2, 132.3, 132.8, 134.7, 134.8, 138, 145.5, 147.3, 168.6. LC/MS-ES$^+$ m/z 302.1, 489.9, 500. Anal. Calcd. for C$_{26}$H$_{26}$ClNO$_5$.0.1EtOAc: C, 66.45; H, 5.68; N, 2.92%. Found C, 66.58; H, 5.38; N, 2.42.

3-Hydroxy-3-phenyl-2-propyl-2,3-dihydroisoindolin-1-one

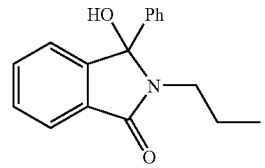

Distilled THF (25 mL) was added to 3-chloro-3-phenyl-isobenzofuranone (1.6 g, 6.62 mmol) followed by n-propylamine (0.59 mL, 7.28 mmol) and triethylamine (1.1 mL, 7.94 mmol) as for general procedure A. The crude product was recrystallised in the minimum amount of boiling ethyl acetate to give 3-hydroxy-3-phenyl-2-propyl-2,3-dihydroisoindolin-1-one as a white solid (1.25 g, 4.67 mmol, 71%); $R_f$ 0.69 (70:30 EtOAc:petrol). mp 181.9-183.1° C. Lit. 184-185° C.[3] $^1$H NMR: (300 MHz, CDCl$_3$) δ 0.72 (t, 3H, J=7.3 Hz, CH$_2$—CH$_2$—CH$_3$), 1.34 (m, 1H, N—CH$_2$—CH$_2$), 1.42 (m, 1H, N—CH$_2$—CH$_2$), 2.84 (m, 1H, N—CH$_2$), 3.21 (s, 1H, OH), 3.34 (m, 1H, N—CH$_2$), 7.19 (m, 2H, Ar—H), 7.26 (m, 2H, Ar—H), 7.31 (m, 2H, Ar—H), 7.38 (m, 2H, Ar—H), 7.66 (m, 1H, Ar—H). $^{13}$C NMR: (75 MHz, CDCl$_3$) δ 12, 22.5, 41.7, 91.8, 122.9, 123.6, 126.5, 128.8, 128.88, 129.9, 130.9, 132.9, 138.9, 149.2, 168.1. LC/MS-ES$^+$ m/z 250, 268 [MH$^+$].

3-Chloro-3-phenyl-2-propyl-2,3-dihydroisoindolin-1-one

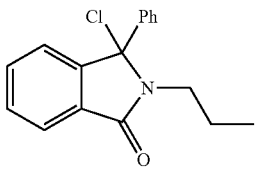

3-Hydroxy-3-phenyl-2-propyl-2,3-dihydroisoindolin-1-one (200 mg, 0.74 mmol) was reacted with thionyl chloride (0.11 mL, 1.49 mmol) and a catalytic amount of DMF (3 drops) as for general procedure B. Removal of the solvent gave 3-chloro-3-phenyl-2-propyl-2,3-dihydroisoindolin-1-one as a colourless oil (211 mg, 0.74 mmol, 100%).

3-(4-tert-Butylbenzyloxy)-3-phenyl-2-propyl-2,3-dihydroisoindolin-1-one (NU8223)

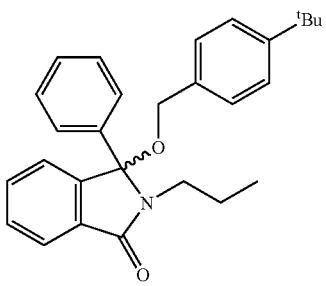

3-Chloro-3-phenyl-2-propyl-2,3-dihydroisoindolin-1-one (211 mg, 0.74 mmol) was reacted with 4-tert-butylbenzyl alcohol (0.13 mL, 0.74 mmol) and potassium carbonate (112 mg, 0.81 mmol) as for general procedure C. The crude product was purified by flash column chromatography (15:85 EtOAc:petrol) to give 3-(4-tert-Butylbenzyloxy)-3-phenyl-2-propyl-2,3-dihydroisoindolin-1-one as a white solid (153 mg, 0.36 mmol, 50%); $R_f$ 0.3 (15:85 EtOAc:petrol). mp 118.7-119.9° C. $\lambda_{max}$ (CH$_3$OH)/nm 217, Abs 0.834. IR: 2927, 1681, 1442, 1357 cm$^{-1}$. $^1$H NMR: (300 MHz, CDCl$_3$) δ 0.70 (t, 3H, J=7.3 Hz, CH$_2$—CH$_2$—CH$_3$), 1.23 (s, 9H, t-Bu), 1.30 (m, 1H, N—CH$_2$), 1.42 (m, 1H, N—CH$_2$—CH$_2$), 3.03 (m, 1H, N—CH$_2$), 3.24 (m, 1H, N—CH$_2$), 3.88 (d, 1H, J=11.3 Hz, O—CH$_2$), 4.15 (d, 1H, J=11.3 Hz, O—CH$_2$), 7.07 (m, 1H, Ar—H), 7.15-7.31 (m, 9H, Ar—H), 7.37 (m, 2H, Ar—H), 7.81 (m, 1H, Ar—H). $^{13}$C NMR: (75 MHz, CDCl$_3$) δ 12.2, 21.9, 31.7, 34.9, 41.9, 64.8, 95.6, 123.5, 123.7, 125.3, 126.4, 127.4, 128.7, 128.8, 130.1, 132.5, 135.0, 139.4, 146.0, 151.0, 168.8. LC/MS-ES$^+$ m/z 368.1, 414.1 [MH$^+$], 436.1 [MNa$^+$]. Anal. Calcd. for C$_{28}$H$_{31}$NO$_2$.0.1EtOAc: C, 80.76; H, 7.59; N, 3.32%. Found C, 80.75; H, 7.30; N, 3.02%.

3-Phenyl-2-propyl-3-(2-pyridin-2-yl-ethoxy)-2,3-dihydroisoindolin-1-one (NU8224)

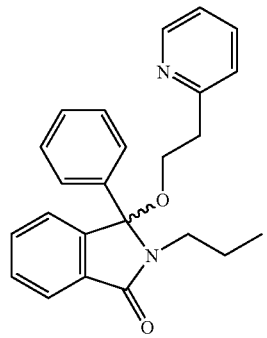

3-Chloro-3-phenyl-2-propyl-2,3-dihydroisoindolin-1-one (211 mg, 0.74 mmol) was reacted with 2-(2-hydroxyethyl)pyridine (0.08 mL, 0.74 mmol) and potassium carbonate (112 mg, 0.81 mmol) as for general procedure C. The crude product was purified by flash column chromatography (40:60 EtOAc:petrol) and recrystallised in the minimum amount of boiling ethyl acetate to give 3-phenyl-2-propyl-3-(2-pyridin-2-yl-ethoxy)-2,3-dihydroisoindolin-1-one as a white solid (105 mg, 0.28 mmol, 38%); $R_f$ 0.29 (40:60 EtOAc:petrol). mp 122.3-124.1° C. $\lambda_{max}$ (CH$_3$OH)/nm 208, Abs 0.335. IR: 2926, 1674, 1440, 1374 cm$^{-1}$. $^1$H NMR: (300 MHz, CDCl$_3$) δ 0.66 (t, 3H, J=7.3 Hz, CH$_2$—CH$_2$—CH$_3$), 1.18 (m, 1H, N—CH$_2$—CH$_2$), 1.34 (m, 1H, N—CH$_2$—CH$_2$), 2.88 (m, 1H, N—CH$_2$), 3.00 (m, 2H, Pyr-CH$_2$), 3.04 (m, 1H, N—CH$_2$), 3.22 (m, 1H, O—CH$_2$), 3.47 (m, 1H, O—CH$_2$), 6.89 (m, 1H, Ar—H), 7.06 (m, 1H, Ar—H), 7.19 (m, 6H, Ar—H), 7.36 (m, 2H, Ar—H), 7.55 (td, 1H, J=7.6, 1.8 Hz, Ar—H), 7.77 (m, 1H, Ar—H), 8.43 (m, 1H, Ar—H). $^{13}$C NMR: (75 MHz, CDCl$_3$) δ 12.1, 21.7, 38.8, 41.7, 62.6, 95.3, 121.8, 123.3, 123.6, 124.1, 128.6, 129.8, 132.4, 132.6, 136.5, 139.5, 145.8, 149.7, 159.3, 168.6. LC/MS-ES$^+$ m/z 251.1, 373.1 [MH$^+$]. Anal. Calcd. for C$_{24}$H$_{24}$N$_2$O$_2$: C, 77.39; H, 6.49; N, 7.52%. Found C, 77.55; H, 6.68; N, 7.53%.

3-(4-Hydroxy-3,5-dimethoxybenzyloxy)-3-phenyl-2-propyl-2,3-dihydroisoindolin-1-one (NU8225)

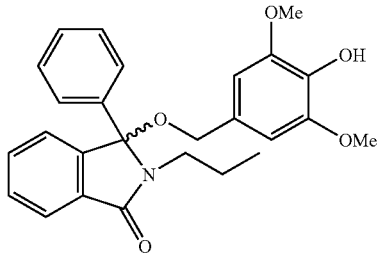

3-Hydroxy-3-phenyl-2-propyl-2,3-dihydroisoindolin-1-one (120 mg, 0.44 mmol) was reacted with thionyl chloride (0.039 mL, 0.53 mmol) and a catalytic amount of DMF (3 drops) as for general procedure B1. Removal of the solvent gave 3-chloro-3-phenyl-2-propyl-2,3-dihydroisoindolin-1-one as a colourless oil (128 mg, 0.44 mmol, 100%).

3-Chloro-3-phenyl-2-propyl-2,3-dihydroisoindolin-1-one (128 mg, 0.44 mmol) was reacted with syringic alcohol (120 mg, 0.65 mmol) as for general procedure C1. The crude product was purified by flash column chromatography (40:60 EtOAc:petrol) to give 3-(4-hydroxy-3,5-dimethoxybenzyloxy)-3-phenyl-2-propyl-2,3-dihydroisoindolin-1-one as a light orange oil (90 mg, 0.20 mmol, 46%); $R_f$ 0.18 (40:60 EtOAc:petrol). $\lambda$ max (CH$_3$OH)/nm 211, Abs 0.975. IR: 3360, 2935, 1681, 1609, 1325 cm$^{-1}$. $^1$H NMR: (300 MHz, CDCl$_3$) $\delta$ 0.72 (t, 3H, J=7.3 Hz, CH$_2$—CH$_2$—CH$_3$), 1.32 (m, 1H, N—CH$_2$—CH$_2$), 1.44 (m, 1H, N—CH$_2$—CH$_2$), 3.03 (m, 1H, N—CH$_2$), 3.26 (m, 1H, N—CH$_2$), 3.79 (s, 6H, OMe), 3.88 (d, 1H, J=11.2 Hz, O—CH$_2$), 4.10 (d, 1H, J=11.2, O—CH$_2$), 6.41 (s, 2H, Ar—H), 7.07 (m, 1H, Ar—H), 7.06 (m, 1H, Ar—H), 7.24 (m, 3H, Ar—H), 7.38 (m, 4H, Ar—H), 7.82 (m, 1H, Ar—H). $^{13}$C NMR: (75 MHz, CDCl$_3$) $\delta$ 12.1, 21.9, 41.9, 56.6, 65.5, 95.6, 104.7, 123.6, 123.7, 126.7, 128.8, 128.9, 129, 130, 132.4, 132.7, 134.6, 139.3, 145.9, 147.3, 168.8. LC/MS-ES$^+$ m/z 250.1, 287.1, 434.1 [MH$^+$], 456.1 [MNa$^+$]. Anal. Calcd. for C$_{26}$H$_{27}$NO$_5$.0.3EtOAc: C, 70.93; H, 6.46; N, 3.03%. Found C, 70.48; H, 6.46; N, 2.83%.

2-(2-Aminoethyl)-3-hydroxy-3-phenyl-2,3-dihydroisoindolin-1-one

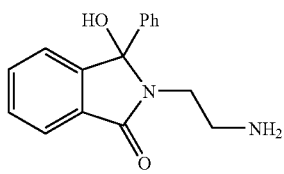

Distilled THF (20 mL) was added to ethylenediamine (2.93 mL, 44 mmol) followed by the inverse addition of 3-chloro-3-phenyl-3H-isobenzofuran-1-one (1.07 g, 4.4 mmol) as for general procedure A. The crude product was purified by flash column chromatography (5:95 MeOH:DCM) to give a yellow oily solid, this was triturated in petrol to produce 2-(2-aminoethyl)-3-hydroxy-3-phenyl-2,3-dihydroisoindolin-1-one as a light yellow solid (766 mg, 2.85 mmol, 65%); $R_f$ 0.2 (5:95 MeOH:DCM). mp 175.5-177° C. Lit. 175-176° C.[6] $^1$H NMR: (300 MHz, CDCl$_3$) $\delta$ 2.57 (m, 1H, N—CH$_2$—CH$_2$—NH$_2$), 2.77 (m, 1H, N—CH$_2$—CH$_2$—NH$_2$), 2.93 (m, 1H, N—CH$_2$—CH$_2$—NH$_2$), 3.94 (bs, 2H, NH$_2$), 4.10 (m, 1H, N—CH$_2$—CH$_2$—NH$_2$), 7.16-7.47 (m, 8H, Ar—H), 7.74 (m, 1H, Ar—H). $^{13}$C NMR: (75 MHz, CDCl$_3$) $\delta$ 40.7, 41.9, 90.3, 122.9, 123.6, 126.8, 128.5, 129, 129.1, 130.1, 133, 141, 150.3, 168.7. LC/MS-ES$^+$ 251, 269 [MH$^+$], 270.1.

N-[2-(1-Hydroxy-3-oxo-1-phenyl-1,3-dihydroisoindolin-2-yl)ethyl]acetamide

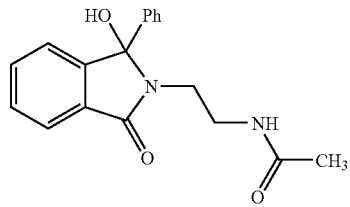

Pyridine (10 mL) was added to 2-(2-aminoethyl)-3-hydroxy-3-phenyl-2,3-dihydroisoindolin-1-one (500 mg, 1.86 mmol), followed by the dropwise addition of acetic anhydride (0.87 mL, 9.3 mmol), over a 5 min period. The system was stirred at room temperature under nitrogen for 16 h and monitored by TLC. Removal of the solvent gave a clear oil that was taken up into ethyl acetate (20 mL), washed with water (3×15 mL), saturated NaHCO$_3$ solution (15 mL), brine (10 mL) and dried with MgSO$_4$. The solvent was removed and the crude product was purified by flash column chromatography (10:90 MeOH:DCM) and recrystallised in the minimum amount of boiling ethyl acetate to give N-[2-(1-hydroxy-3-oxo-1-phenyl-1,3-dihydroisoindolin-2-yl)ethyl]acetamide as a white solid (434 mg, 1.39 mmol, 75%); $R_f$ 0.35 (10:90 MeOH:DCM). mp 181.2-183° C. Lit. 184-188° C.[6] $^1$H NMR: (300 MHz, CDCl$_3$) $\delta$ 1.77 (s, 3H, NHCOCH$_3$), 2.82-2.94 (m, 2H, N—CH$_2$—CH$_2$—NHCOCH$_3$), 3.87 (m, 1H, N—CH$_2$—CH$_2$—NHCOCH$_3$), 4.11 (m, 1H, N—CH$_2$—CH$_2$—NHCOCH$_3$), 6.33 (m, 1H, NH), 6.41 (s, 1H, OH), 7.22-7.41 (m, 8H, Ar—H), 7.65 (m, 1H, Ar—H). $^{13}$C NMR: (75 MHz, CDCl$_3$) $\delta$ 23.5, 39.1, 40.7, 92.2, 122.2, 123.2, 126.3, 128.7, 128.9, 129.4, 129.9, 133.3, 139.4, 150.2, 169.1, 173.1. LC/MS-ES$^+$ m/z 293.1, 311.1 [MH$^+$].

n-Propylbenzamide

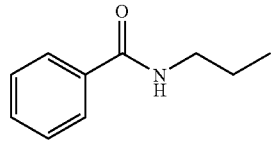

Dry DCM (30 mL) was added to benzoyl chloride (2.06 mL, 17.7 mmol) followed by the dropwise addition of propylamine (3.19 mL, 38.9 mmol) over 5 min at 0° C. The system was stirred at 0° C. under nitrogen for 1 h and monitored by TLC. After 1 h the system was washed with 1M HCl (20 mL), brine (10 mL) and dried with MgSO$_4$. The solvent was removed to give N-Propylbenzamide as a white solid (2.6 g, 15.9 mmol, 90%); $R_f$ 0.38 (40:60 EtOAc:petrol). mp 87.6-88.9° C. Lit. 83-84° C.[7] $^1$H NMR: (300 MHz, CDCl$_3$) $\delta$ 0.90 (t, 3H, J=7.4 Hz, CH$_2$—CH$_2$—CH$_3$), 1.56 (sex, 2H, J=7.2 Hz, N—CH$_2$—CH$_2$), 3.33 (m, 2H, N—CH$_2$), 6.21 (bs, 1H, NH), 7.31-7.43 (m, 3H, Ar—H), 7.69 (m, 2H, Ar—H). $^{13}$C NMR:

(75 MHz, CDCl$_3$) δ 11.8, 23.3, 42.1, 127.2, 128.8, 131.6, 135.2, 167.9. LC/MS-ES$^+$ m/z 164.2 [MH$^+$], 327.1, 328.1.

4-(2-Trimethylsilanylethoxymethoxy)benzoic acid ethyl ester

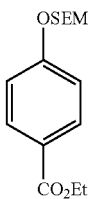

Dry CH$_3$CN (35 mL) was added to 4-Hydroxybenzoic acid ethyl ester (2.5 g, 15 mmol) followed by the addition of cesium carbonate (5.37 g, 16.5 mmol) trimethylsilylethoxymethylchloride (2.92 mL, 16.5 mmol). The system was stirred at room temperature under nitrogen for 24 h and monitored by TLC. Removal of the solvent gave a clear oil that was taken up into ethyl acetate (50 mL), washed with water (3×25 mL), brine (20 mL) and dried with MgSO$_4$. The solvent was removed and the crude product was purified by flash column chromatography (5:95 EtOAc:petrol) to give 4-(2-trimethylsilanylethoxymethoxy)benzoic acid ethyl ester as a clear oil (3.87 g, 13 mmol, 87%); R$_f$ 0.54 (10:90 EtOAc: petrol). $^1$H NMR: (300 MHz, CDCl$_3$) δ 0.00 (s, 9H, Si—(CH$_3$)$_3$), 0.95 (m, 2H, R—O—CH$_2$—CH$_2$—Si), 1.26 (t, 3H, J=7.1 Hz, O—CH$_2$—CH$_3$), 3.75 (m, 2H, O—CH$_2$—CH$_2$—Si), 4.35 (q, 2H, J=7.14 Hz, O—CH$_2$—CH$_3$) 5.27 (s, 2H, O—CH$_2$—O), 7.05 (m, 2H, Ar—H), 7.99 (m, 2H, Ar—H). $^{13}$C NMR: (75 MHz, CDCl$_3$) δ −1.2, 14.7, 18.4, 61, 66.9, 92.9, 115.9, 124.1, 131.8, 161.4, 166.7. LC/MS-ES$^+$ m/z 118.9, 268, 297.1 [MH$^+$], 298.1.

3-Hydroxy-2-propyl-3-[4-(2-trimethylsilanylethoxymethoxy)phenyl]-2,3-dihydro-isoindolin-1-one

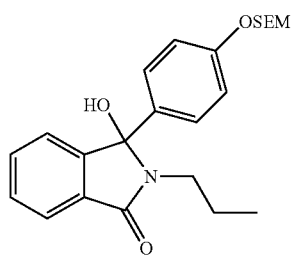

To a solution of distilled THF (15 mL) and n-propylbenzamide (650 mg, 3.98 mmol) cooled to −78° C. under nitrogen, a 1.4 M solution of sec-butyl lithium (6.25 mL, 8.76 mmol) was added dropwise over a 10 min period. On completion of addition the deep yellow solution was stirred at −78° C. for a further 30 min. 4-(2-trimethylsilanylethoxymethoxy) benzoic acid ethyl ester (1.41 g, 4.77 mmol) was dissolved up in THF (7 mL) and added dropwise to the system over a 5 min period, the resulting green solution was stirred for a further 30 min at −78° C. On completion the reaction was quenched with a saturated ammonium chloride solution, extracted with DCM (4×50 mL). The organic extracts were then combined, washed with brine (50 mL) dried with MgSO$_4$, the solvent was removed to give a yellow solid that was washed with excess petrol to give 3-hydroxy-2-propyl-3-[4-(2-trimethylsilanylethoxymethoxy)phenyl]-2,3-dihydro-isoindolin-1-one as a fine white solid (1.24 g, 2.99 mmol, 75%); R$_f$ 0.58 (40:60 EtOAc:petrol).). mp 112.9-114.1° C. λ$_{max}$ (CH$_3$OH)/nm 227.5, Abs 0.970. IR: 3286, 2962, 1683, 1606, 1469, 1508 cm$^{-1}$. $^1$H NMR $^1$H NMR: (300 MHz, CDCl$_3$) δ 0.00 (s, 9H, Si—(CH$_3$)$_3$), 0.79 (t, 3H, J=7.4 Hz, CH$_2$—CH$_2$—CH$_3$), 0.95 (m, 2H, O—CH$_2$—CH$_2$—Si), 1.38 (m, 1H, N—CH$_2$—CH$_2$), 1.51 (m, 1H, N—CH$_2$—CH$_2$), 2.91 (m, 1H, N—CH$_2$), 3.36, (m, 1H, N—CH$_2$), 3.75 (m, 2H, O—CH$_2$—CH$_2$—Si), 4.82 (bs, 1H, OH), 5.21 (s, 2H, O—CH$_2$—O), 6.98 (d, 2H, J=8.9 Hz, Ar—H), 7.26 (m, 1H, Ar—H), 7.30 (d, 2H, J=8.8 Hz, Ar—H), 7.38-7.50 (dtd, 2H, J=20.2, 7.3, 1.1 Hz, Ar—H), 7.66 (m, 1H, Ar—H). $^{13}$C NMR: (75 MHz, CDCl$_3$) δ −3.6, 9.6, 15.9, 20.1, 39.2, 64.2, 89.2, 90.7, 114, 120.5, 121.1, 125.4, 127.3, 128.5, 129.5, 130.4, 146.9, 155.4, 165.6. LC/MS-ES$^+$ m/z 297.1, 355, 396.1, 397.1, 414.1 [MH$^+$].

3-(4-tert-Butylbenzyloxy)-2-propyl-3-[4-(2-trimethylsilanylethoxymethoxy)-phenyl]-2,3-dihydroisoindolin-1-one (NU8233)

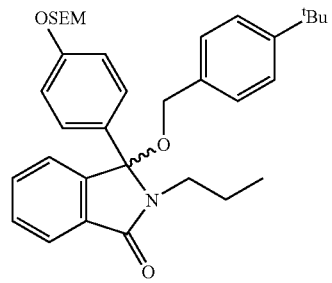

3-Chloro-2-propyl-3-[4-(2-trimethylsilanylethoxymethoxy)phenyl]-2,3-dihydroiso-indol-1-one (155 mg, 0.36 mmol) was reacted with 4-tert-butylbenzyl alcohol (0.07 mL, 0.39 mmol) and triethylamine (0.11 mL, 0.79 mmol) as for general procedure H. The crude product was purified by flash column chromatography (30:70 EtOAc: petrol) and C18 reverse phase column chromatography (graduated 20:80 H$_2$O:MeOH, 100 MeOH) to give to give 3-(4-tert-butylbenzyloxy)-2-propyl-3-[4-(2-trimethylsilanylethoxymethoxy)-phenyl]-2,3-dihydroisoindolin-1-one as a colourless oil (60 mg, 0.11 mmol, 30%); R$_f$ 0.67 (30:70 EtOAc:petrol). λ$_{max}$ (CH$_3$OH)/nm 222, Abs 0.632. IR: 2957, 1703, 1604, 1465, 1370 cm$^{-1}$. $^1$H NMR: (300 MHz, CDCl$_3$) δ 0.00 (s, 9H, Si—(CH$_3$)$_3$), 0.82 (t, 3H, J=7.4 Hz, CH$_2$—CH$_2$—CH$_3$), 0.95 (m, 2H, O—CH$_2$—CH$_2$—Si), 1.34 (s, 9H, t-Bu), 1.41 (m, 1H, N—CH$_2$—CH$_2$), 1.55 (m, 1H, N—CH$_2$—CH$_2$), 3.13 (m, 1H, N—CH$_2$), 3.33, (m, 1H, N—CH$_2$), 3.75 (m, 2H, O—CH$_2$—CH$_2$—Si), 3.96 (d, 1H, J=11.2 Hz, O—CH$_2$), 4.23 (d, 1H, J=11.3 Hz, O—CH$_2$), 5.22 (s, 2H, O—CH$_2$—O), 6.98 (d, 2H, J=8.9 Hz, Ar—H), 7.18 (m, 1H, Ar—H), 7.25 (d, 2H, J=8.2 Hz, Ar—H), 7.37 (m, 4H, Ar—H), 7.49 (m, 2H, Ar—H), 7.91 (m, 1H, Ar—H). $^{13}$C NMR: (75 MHz, CDCl$_3$) δ −1.4, 11.8, 17.9, 21.5, 31.3, 34.5, 41.4, 64.3, 66.2, 92.7, 95.1, 115.9, 123.1, 123.2, 125.2, 126.9, 127.6, 129.5, 131.9, 132, 132.3, 134.6, 145.7, 150.5, 157.4, 168.2. LC/MS-ES⁺ m/z 396.1, 397.1. Anal. Calcd. for $C_{34}H_{45}NO_4Si$: C, 72.95; H, 8.10; N, 2.50%. Found C, 73.61; H, 8.23; N, 2.43%.

3-(3-Hydroxypropoxy)-2-propyl-3-[4-(2-trimethylsilanylethoxymethoxy)-phenyl]-2,3-dihydroisoindolin-1-one (NU8234)

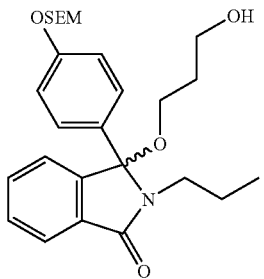

3-Chloro-2-propyl-3-[4-(2-trimethylsilanylethoxymethoxy)phenyl]-2,3-dihydroiso-indol-1-one (189 mg, 0.44 mmol) was reacted with 1,3-propanediol (0.22 mL, 3.1 mmol) and triethylamine (0.14 mL, 0.96 mmol) as for general procedure H. The crude product was purified by flash column chromatography (50:50 EtOAc:petrol) and C18 reverse phase column chromatography (graduated 20:80 H₂O:MeOH, 100 MeOH) to give 3-(3-hydroxypropoxy)-2-propyl-3-[4-(2-trimethylsilanylethoxymethoxy)phenyl]-2,3-dihydroisoindolin-1-one as a colourless oil (108 mg, 0.22 mmol, 52%); $R_f$ 0.3 (50:50 EtOAc:petrol). $\lambda_{max}$ (CH₃OH)/nm 229, Abs 0.455. IR: 3429, 2952, 2877, 1684, 1608, 1508, 1467 cm⁻¹. ¹H NMR: (300 MHz, CDCl₃) δ –0.03 (s, 9H, Si(CH₃)₃), 0.82 (t, 3H, J=7.4 Hz, CH₂—CH₂—CH₃), 0.95 (m, 2H, R—O—CH₂—CH₂—Si), 1.38 (m, 1H, N—CH₂—CH₂), 1.54 (m, 1H, N—CH₂—CH₂), 1.85 (m, 2H, O—CH₂—CH₂—CH₂—OH), 2.32 (bs, 1H, OH), 3.06 (m, 2H, N—CH₂, O—CH₂), 3.28, (m, 2H, N—CH₂, O—CH₂), 3.78 (m, 4H, O—CH₂—CH₂—Si, R—O—CH₂—CH₂—CH₂—OH), 5.21 (s, 2H, O—CH₂—O), 6.98 (d, 2H, J=9 Hz, Ar—H), 7.17 (m, 1H, Ar—H), 7.27 (d, 2H, J=8.8 Hz, Ar—H), 7.47 (m, 2H, Ar—H), 7.85 (m, 1H, Ar—H). ¹³C NMR: (75 MHz, CDCl₃) δ –0.3, 0, 0.3, 13.2, 19.4, 22.9, 33.6, 42.7, 61.8, 62, 67.7, 94.1, 96.4, 117.4, 124.3, 124.6, 128.8, 130.9, 133.2, 133.3, 133.8, 147.1, 158.9, 169.7. LC/MS-ES⁺ m/z 338.1, 366.1, 396.1, 397.2. Anal. Calcd. for $C_{26}H_{37}NO_5Si$: C, 66.21; H, 7.91; N, 2.97%. Found C, 66.05; H, 8.06; N, 2.84%.

2-Propyl-3-(2-pyridin-2-yl-ethoxy)-3-[4-(2-trimethylsilanylethoxymethoxy)-phenyl]-2,3-dihydroisoindolin-1-one (NU8235)

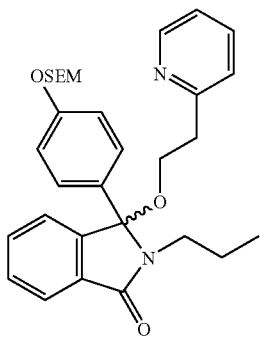

3-Chloro-2-propyl-3-[4-(2-trimethylsilanylethoxymethoxy)phenyl]-2,3-dihydroiso-indol-1-one (189 mg, 0.44 mmol) was reacted with 2-(2-hydroxyethyl)pyridine (0.05 mL, 0.48 mmol) and triethylamine (0.14 mL, 0.96 mmol) as for general procedure H. The crude product was purified by flash column chromatography (45:55 EtOAc:petrol) and C18 reverse phase column chromatography (graduated 20:80 H₂O:MeOH, 100 MeOH) to give 2-propyl-3-(2-pyridin-2-yl-ethoxy)-3-[4-(2-trimethylsilanylethoxymethoxy)-phenyl]-2,3-dihydroisoindolin-1-one as a colourless oil (109 mg, 0.21 mmol, 47%); $R_f$ 0.37 (50:50 EtOAc:petrol). $\lambda_{max}$ (CH₃OH)/nm 230, Abs 0.925. IR: 2947, 1700, 1594, 1468, 1435, 1373 cm⁻¹. ¹H NMR: (300 MHz, CDCl₃) δ 0.00 (s, 9H, Si(CH₃)₃), 0.76 (t, 3H, J=7.3 Hz, CH₂—CH₂—CH₃), 0.95 (m, 2H, R—O—CH₂—CH₂—Si), 1.30 (m, 1H, N—CH₂—CH₂), 1.44 (m, 1H, N—CH₂—CH₂), 2.97-3.17 (m, 4H, N—CH₂, O—CH₂—CH₂-pyr), 3.29 (m, 1H, O—CH₂), 3.53 (m, 1H, O—CH₂), 3.74 (m, 2H, O—CH₂—CH₂—Si), 5.20 (s, 2H, O—CH₂—O), 6.97 (m, 3H, Ar—H), 7.13-7.25 (m, 4H, Ar—H), 7.45 (m, 2H, Ar—H), 7.64 (dt, 1H, J=7.6, 1.7 Hz, Ar—H), 7.84 (m, 1H, Ar—H), 8.53 (m, 1H, Ar—H). ¹³C NMR: (75 MHz, CDCl₃) δ 0.00, 13.2, 19.4, 22.8, 39.9, 42.6, 63.6, 67.7, 94.2, 96.2, 117.3, 122.8, 124.3, 124.6, 125.1, 128.9, 130.8, 133.4, 133.5, 133.6, 137.6, 147.1, 150.7, 158.8, 160.3, 169.6. LC/MS-ES⁺ m/z 266, 338.1, 339, 366, 396.1, 397.2, 428.1. Anal. Calcd. for $C_{30}H_{38}N_2O_4Si$: C, 69.46; H, 7.38; N, 5.40%. Found C, 69.02; H, 8.09; N, 5.57%.

3-(4-Hydroxy-3,5-dimethoxybenzyloxy)-2-propyl-3-[4-(2-trimethylsilanylethoxy-methoxy)-phenyl]-2,3-dihydroisoindolin-1-one (NU8236)

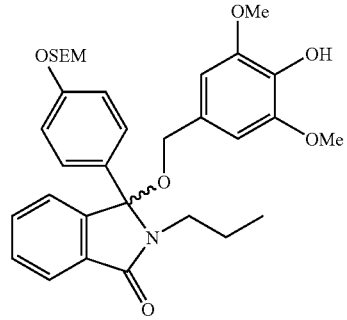

3-Chloro-2-propyl-3-[4-(2-trimethylsilanylethoxymethoxy)phenyl]-2,3-dihydroiso-indol-1-one (135 mg, 0.31 mmol) was reacted with syringic alcohol (127 mg, 0.69 mmol) as for general procedure H. The crude product was purified by flash column chromatography (35:65 EtOAc:petrol), C18 reverse phase column chromatography (graduated 20:80 H₂O:MeOH, 100 MeOH) and HPLC (H₂O:CH₃CN, 270 nm) to give 3-(4-hydroxy-3,5-dimethoxybenzyloxy)-2-propyl-3-[4-(2-trimethylsilanylethoxy-methoxy)-phenyl]-2,3-dihydroisoindolin-1-one as a colourless oil (38 mg, 0.065 mmol, 2%); $R_f$ 0.35 (40:60 EtOAc:petrol). $\lambda_{max}$ (CH₃OH)/nm 210, Abs 0.336. IR: 3371, 2947, 1689, 1604, 1460, 1427, 1372 cm⁻¹. ¹H NMR: (300 MHz, CDCl₃) δ –0.02 (s, 9H, Si—(CH₃)₃), 0.83 (t, 3H, J=7.4 Hz, CH₂—CH₂—CH₃), 0.95 (m, 2H, R—O—CH₂—CH₂—Si), 1.43 (m, 1H, N—CH₂—CH₂), 1.55 (m, 1H, N—CH₂—CH₂), 3.12 (m, 1H, N—CH₂), 3.34 (m, 1H, N—CH₂), 3.75 (m, 2H, O—CH₂—CH₂—Si), 3.89 (s, 6H, OMe), 3.94 (d, 1H, J=11.2 Hz, O—CH$_2$), 4.17 (d, 1H, J=11.3 Hz, O—CH$_2$), 5.22 (s, 2H, O—CH$_2$—O), 5.55 (s, 1H, OH), 6.49 (s, 2H, Ar—H), 7.00 (d, 2H, J=9.1 Hz, Ar—H), 7.17 (m, 1H, Ar—H), 7.34 (d, 2H, J=8.8 Hz, Ar—H), 7.49 (m, 2H, Ar—H), 7.90 (m, 1H, Ar—H). $^{13}$C NMR: (75 MHz, CDCl$_3$) δ −3.3, 9.8, 16, 19.6, 39.5, 54.3, 63.1, 64.3, 90.8, 93.1, 102.2, 114, 121.2, 121.3, 125.6, 126.7, 127.6, 129.8, 130, 130.3, 132.2, 143.7, 144.9, 155.5, 160.3, 166.3. LC/MS-ES$^+$ m/z 355, 396.1, 397.1, 414.1, 602 [MNa$^+$]. Anal. Calcd. for C$_{32}$H$_{41}$NO$_7$Si: C, 66.29; H, 7.13; N, 2.42%. Found C, 67.26; H, 7.22; N, 1.65%; HRMS (EI) m/z Calcd. for C$_{32}$H$_{41}$NO$_7$Si: 579.2652. Found 579.2673.

2-(4-Hydroxy)benzoylbenzoic acid

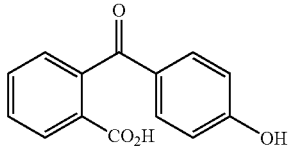

Phenolphthalein (7 g, 22 mmol) was dissolved in aqueous potassium hydroxide solution (7 g in 70 mL) giving a vivid purple solution. Hydroxylamine hydrochloride (1.71 g, 24 mmol) was added and the solution heated to 80° C. The reaction was monitored by acidifying a sample of the mixture with acetic acid, filtering off the precipitate and adding potassium hydroxide. When no pink colour was observed on the addition of potassium hydroxide the reaction was left stirring for another 5 min. Ethanol (14 mL) was added, and acetic acid was added dropwise until the solution was slightly acidic. A sulphur yellow precipitate formed and was washed with water and dissolved in hot sulphuric acid (10%, 140 mL) giving a bright yellow solution that was refluxed for 2 h. On cooling a deep yellow solid was obtained filtered and washed with ice cold water yielding 2-(4-Hydroxy)benzoylbenzoic acid as a light yellow solid (4.04 g, 16.6 mmol, 76%); R$_f$ 0.06 (40:60 EtOAc:petrol). mp 228.4-230.6° C. Lit. 231° C.[8] IR: 3232, 3163, 1688, 1644, 1577, 1381 cm$^{-1}$. $^1$H NMR: (300 MHz, d$_6$-DMSO) δ 6.83 (m, 2H, Ar—H), 7.34 (dd, 1H, J=7.4, 1.3 Hz, Ar—H), 7.50 (m, 2H, Ar—H), 7.58-7.71 (dtd, 2H, J=22.4, 7.4, 1.3 Hz, Ar—H), 7.95 (dd, 1H, J=7.6, 1.3 Hz, Ar—H), 10.30 (bs, 1H, COOH). $^{13}$C NMR: (75 MHz, d$_6$-DMSO) δ 115.5, 127.7, 128.6, 129.6, 130, 130.1, 131.9, 132.4, 142.2, 162.4, 167.3, 195.1. LC/MS-ES$^+$ m/z 129.3, 225.1, 264.9, 506.8.

2-(4-Hydroxybenzoyl)benzoic acid methyl ester

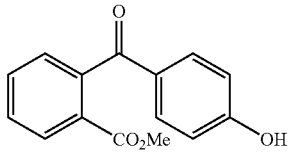

Acetyl chloride (2.67 mL, 37.5 mmol), was added dropwise to ice cold methanol (40 mL) whilst stirring. 2-(4-Hydroxy)benzoylbenzoic acid (3.9 g, 16.1 mmol) was added and the mixture was allowed to warm to room temperature. After 16 h the solvent was removed leaving a light green oil which was triturated with water, washed with ice cold petrol and dried in vacuo giving 2-(4-hydroxybenzoyl)benzoic acid methyl ester as a light green solid (3.8 g, 14.8 mmol, 92%); R$_f$ 0.43 (40:60 EtOAc:petrol). mp 147.1-149.3° C. Lit. 149-150° C.[9] IR: 3338, 1719, 1644, 1569, 1511, 1432 cm$^{-1}$. $^1$H NMR: (300 MHz, d$_6$-DMSO) δ 3.58 (s, 3H, COOCH$_3$), 6.84 (d, 2H, J=8.6 Hz, Ar—H), 7.41 (d, 1H, J=7.3 Hz, Ar—H), 7.51 (d, 2H, J=8.6, Ar—H), 7.61-7.74 (dt, 2H, J=24.2, 6.5 Hz, Ar—H), 7.95 (d, 1H, J=7.4 Hz, Ar—H), 10.47 (bs, 1H, COOH). $^{13}$C NMR: (75 MHz, d$_6$-DMSO) δ 52.4, 115.7, 127.7, 128.5, 129.6, 129.9, 130.1, 131.9, 132.4, 141.9, 162.5, 166.3, 194.7. LC/MS-ES$^+$ m/z 225, 256.9 [M$^+$], 278.9.

2-[4-(2-Trimethylsilanylethoxymethoxy)benzoyl]benzoic acid methyl ester

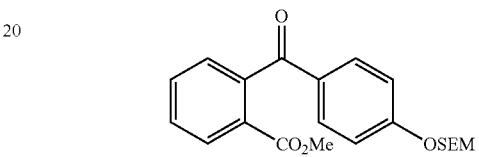

Dry CH$_3$CN (50 mL) was added to 2-(4-hydroxybenzoyl)benzoic acid methyl ester (3.65 g, 15 mmol) followed by cesium carbonate (5.4 g, 16.5 mmol) and trimethylsilylethoxymethylchloride (2.9 mL, 16.5 mmol). The system was stirred at room temperature under nitrogen for 24 h and monitored by TLC. Removal of the solvent gave a light yellow oil that was taken up into ethyl acetate (100 mL), washed with water (3×50 mL), brine (40 mL) and dried with MgSO$_4$. The solvent was removed and the crude product was purified by flash column chromatography (5:95 EtOAc:petrol) to give 2-[4-(2-trimethylsilanylethoxymethoxy)benzoyl]benzoic acid methyl ester as a yellow oil (3.94 g, 10.2 mmol, 67%); R$_f$ 0.79 (40:60 EtOAc:petrol). λ$_{max}$ (CH$_3$OH)/nm 282, Abs 1.072. IR: 2939, 1720, 1666, 1589, 1489 cm$^{-1}$. $^1$H NMR: (300 MHz, CDCl$_3$) δ 0.00 (s, 9H, Si—(CH$_3$)$_3$), 0.94 (m, 2H, R—O—CH$_2$—CH$_2$—Si), 3.66 (s, 3H, COOCH$_3$), 3.75 (m, 2H, O—CH$_2$—CH$_2$—Si), 5.27 (s, 2H, O—CH$_2$—O), 7.05 (m, 2H, Ar—H), 7.37 (m, 1H, Ar—H), 7.53-7.66 (dtd, 2H, J=22.6, 7.4, 1.4 Hz, Ar—H), 7.72 (m, 2H, Ar—H), 8.05 (m, 1H, Ar—H). $^{13}$C NMR: (75 MHz, d$_6$-DMSO) δ −2, 16.8, 51.5, 65.3, 91.5, 115.1, 127, 128, 129, 129.2, 129.6, 130.4, 132, 140.7, 160.2, 165.2, 194. LC/MS-ES$^+$ m/z 163.2, 297.1, 387.1 [MH$^+$], 409 [MNa$^+$]. HRMS (EI) m/z Calcd. for C$_{21}$H$_{26}$O$_5$Si: 386.1549. Found 386.1562.

2-[4-(2-Trimethylsilanylethoxymethoxy)benzoyl]benzoic acid

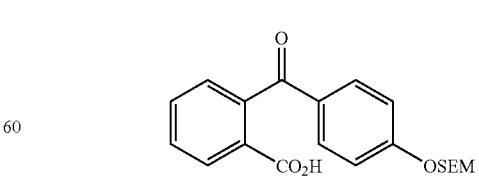

Dry DCM (25 mL) was added to 2-[4-(2-trimethylsilanylethoxymethoxy)benzoyl]-benzoic acid methyl ester (3.8 g, 9.8 mmol) followed by potassium trimethylsilanolate (1.53 g, 10.8 mmol). The system was stirred at room temperature under nitrogen for 16 h and monitored by TLC. Removal of the solvent gave a light yellow oil that was taken up into ethyl acetate (100 mL), washed with 5% HCl solution (3×30 mL), brine (30 mL) and dried with MgSO$_4$. The solvent was removed to give 2-[4-(2-trimethylsilanylethoxymethoxy) benzoyl]benzoic acid as a yellow oil (3.66 g, 9.8 mmol, 99%); $R_f$ 0.1 (40:60 EtOAc:petrol). $\lambda_{max}$ (CH$_3$OH)/nm 276, 217, Abs 1.799, 2.108 respectively. IR: 3215, 3177, 1666, 1593 cm$^{-1}$. $^1$H NMR: (300 MHz, CDCl$_3$) δ 0.00 (s, 9H, Si—(CH$_3$)$_3$), 0.96 (m, 2H, R—O—CH$_2$—CH$_2$—Si), 3.76 (m, 2H, O—CH$_2$—CH$_2$—Si), 5.27 (s, 2H, O—CH$_2$—O), 7.04 (m, 2H, Ar—H), 7.34 (m, 1H, Ar—H), 7.52-7.68 (dtd, 2H, J=30.2, 7.6, 1.3 Hz, Ar—H), 7.69 (m, 2H, Ar—H), 8.07 (m, 1H, Ar—H), 10.31 (bs, 1H, COOH). $^{13}$C NMR: (75 MHz, CDCl$_3$) δ −3.2, 16.1, 64.8, 90.7, 113.8, 125.7, 126, 127.4, 128.8, 129.1, 129.9, 131.2, 140.9, 159.6, 168.8, 194. LC/MS-ES$^+$ m/z 297.1, 373.1 [MH$^+$]. HRMS (EI) m/z Calcd. for C$_{20}$H$_{24}$O$_5$Si: 372.1393. Found 372.1387

3-Chloro-3-[4-(2-trimethylsilanylethoxymethoxy) phenyl]-3H-isobenzofuran-1-one

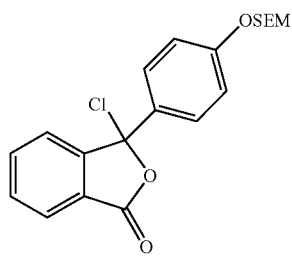

Distilled THF (10 mL) was added to 2-[4-(2-trimethylsilanylethoxymethoxy)-benzoyl]benzoic acid (1.86 g, 5 mmol) followed by thionyl chloride (0.43 mL, 6 mmol) and 3 drops of DMF. The system was stirred at room temperature under nitrogen for 2 h and monitored by TLC. The solvent was removed to give 3-chloro-3-[4-(2-trimethylsilanylethoxymethoxy)phenyl]-3H-isobenzofuran-1-one as a clear oil.

2-Benzyl-3-hydroxy-3-[4-(2-trimethylsilanylethoxymethoxy)phenyl]-2,3-dihydro-isoindolin-1-one

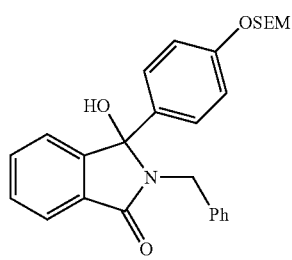

Distilled THF (10 mL) was added to 3-chloro-3-[4-(2-trimethylsilanylethoxymethoxy)phenyl]-3H-isobenzofuran-1-one (2.39 g, 5 mmol). followed by benzylamine (1.1 mL, 10 mmol), and triethylamine (1.39 mL, 10 mmol) resulting in the formation a creamy white/yellow precipitate. The reaction system was stirred at room temperature under nitrogen for 2 h and monitored by TLC. On completion the solvent was removed under vacuum and the residue was taken up into ethyl acetate (30 mL), washed with water (3×25 mL), brine (20 mL) and dried with MgSO$_4$, the solvent was removed under vacuum. The crude product was purified by flash column chromatography (20:80 EtOAc:petrol) and C18 reverse phase column chromatography (graduated 20:80 H$_2$O: MeOH, 100 MeOH) to give 2-benzyl-3-hydroxy-3-[4-(2-trimethylsilanylethoxymethoxy)phenyl]-2,3-dihydroisoindolin-1-one as a clear yellow oil (140 mg, 0.3 mmol, 0.6%); $R_f$ 0.51 (40:60 EtOAc:petrol). $\lambda_{max}$ (CH$_3$OH)/nm 213, Abs 1.161. IR: 3306, 2953, 1677, 1609, 1508, 1469 cm$^{-1}$. $^1$H NMR: (300 MHz, CDCl$_3$) δ 0.00 (s, 9H, Si—(CH$_3$)$_3$), 0.95 (m, 2H, R—O—CH$_2$—CH$_2$—Si), 2.90 (bs, 1H, OH), 3.74 (m, 2H, O—CH$_2$—CH$_2$—Si), 4.06 (d, 1H, J=14.9 Hz, N—CH$_2$), 4.77 (d, 1H, J=14.9 Hz, N—CH$_2$), 5.19 (s, 2H, O—CH$_2$—O), 6.92 (m, 2H, Ar—H), 7.12-7.29 (m, 8H, Ar—H), 7.45 (m, 2H, Ar—H), 7.80 (m, 1H, Ar—H). $^{13}$C NMR: (75 MHz, CDCl$_3$) δ −1.9, 17.4, 42.3, 65.7, 91, 92.2, 115.5, 122, 122.8, 126.4, 127, 127.6, 128.1, 128.9, 129.6, 130.5, 132.1, 137.6, 148.4, 156.9, 167. LC/MS-ES$^+$ m/z 297.1, 386.1, 444.1, 445.1, 484 [MNa$^+$]. HRMS (EI) m/z Calcd. for C$_{27}$H$_{31}$NO$_4$Si: 461.2022. Found 461.2017.

2-Benzyl-3-chloro-3-[4-(2-trimethylsilanylethoxymethoxy)phenyl]-2,3-dihydroiso-indol-1-one

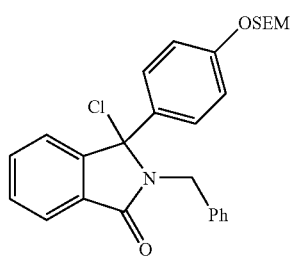

2-Benzyl-3-hydroxy-3-[4-(2-trimethylsilanylethoxymethoxy)phenyl]-2,3-dihydroiso-indol-1-one (125 mg, 0.27 mmol) was reacted with thionyl chloride (0.019 mL, 0.27 mmol) and a catalytic amount of DMF (3 drops) as for general procedure G. Removal of the solvent gave 2-benzyl-3-chloro-3-[4-(2 trimethylsilanylethoxymethoxy)phenyl]-2,3-dihydroiso-indol-1-one as a colourless oil (129 mg, 0.27 mmol, 100%).

2-Benzyl-3-(4-hydroxy-3,5-dimethoxybenzyloxy)-3-[4-(2-trimethylsilanylethoxy-methoxy)phenyl]-2,3-dihydroisoindolin-1-one (NU8238)

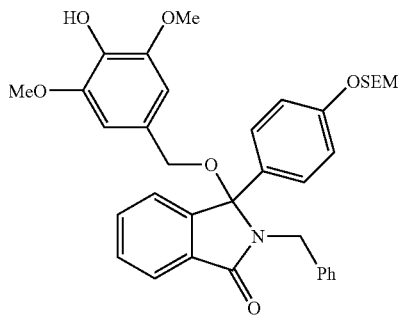

2-Benzyl-3-chloro-3-[4-(2-trimethylsilanylethoxymethoxy)phenyl]-2,3-dihydroiso-indol-1-one (129 mg, 0.27 mmol) was reacted with syringic alcohol (109 mg, 0.59 mmol) as for general procedure H1. The crude product was purified by flash column chromatography (40:60

EtOAc:petrol) and HPLC (H$_2$O:MeOH, 270 nm) to give 2-benzyl-3-(4-hydroxy-3,5-dimethoxybenzyloxy)-3-[4-(2-trimethylsilanylethoxy-methoxy)phenyl]-2,3-dihydroisoindolin-1-one as a colourless oil (19 mg, 0.03 mmol, 11%); R$_f$ 0.23 (40:60 EtOAc:petrol). $^1$H NMR: (300 MHz, CDCl$_3$) δ $^1$H NMR: (300 MHz, CDCl$_3$) δ 0.00 (s, 9H, Si—(CH$_3$)$_3$), 0.96 (m, 2H, R—O—CH$_2$—CH$_2$—Si), 3.60 (d, 1H, J=10.8 Hz, O—CH$_2$), 3.67 (d, 1H, J=10.8 Hz, O—CH$_2$), 3.75 (m, 2H, O—CH$_2$—CH$_2$—Si), 3.82 (s, 6H, OMe), 4.03 (d, 1H, J=14.7 Hz, N—CH$_2$), 4.83 (d, 1H, J=14.7 Hz, N—CH$_2$), 5.20 (s, 2H, O—CH$_2$—O), 5.46 (s, 1H, OH), 6.13 (s, 2H, Ar—H), 6.95 (d, 2H, J=9 Hz, Ar—H), 7.13-7.22 (m, 4H, Ar—H), 7.28 (d, 2H, J=8.9 Hz, Ar—H), 7.34 (m, 2H, Ar—H), 7.49 (m, 2H, Ar—H), 7.94 (m, 1H, Ar—H). $^{13}$C NMR: (75 MHz, CDCl$_3$) δ −1, 18.4, 43.6, 56.6, 65.6, 66.7, 93.2, 96, 104.9, 116.4, 123.5, 123.9, 127.4, 128.1, 128.5, 128.9, 129.8, 129.9, 131.8, 132, 132.9, 134.4, 138.1, 146.3, 147, 157.9, 168.6. LC/MS-ES$^+$ m/z 354.9, 443.9, 461.9, 627.9 [M$^+$]. HRMS (EI) m/z Calcd. for C$_{36}$H$_{41}$NO$_7$Si: 627.2652. Found 627.2622.

N-{2-[1-(4-Chlorophenyl)-1-hydroxy-3-oxo-1,3-dihydroisoindolin-2-yl]-ethyl}acetamide

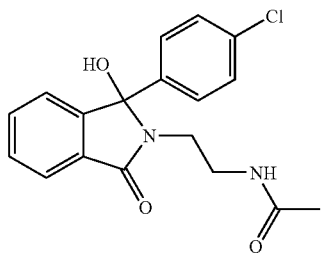

To a stirred solution of 4-chloro-2-benzoyl benzoic acid (400 mg, 1.53 mmol) in dry THF (10 Ml), thionyl chloride (0.22 ml, 3.06 mmol) was added followed by three drops of dry DMF at room temperature under nitrogen atmosphere. After stirring for overnight, the solvent was evaporated to dryness under reduced pressure. The residue was dissolved in THF (10 Ml) and N-acetyl ethylenediamine (0.17 ml, 1.84 mmol) was added followed by triethylamine (0.25 ml, 1.84 mmol) at room temperature. The progress of the reaction was monitored by TLC. After 30 min. the TLC confirmed the completion of the reaction. The solvent was evaporated and the residue was dissolved in ethylacetate (100 ml). The organic layer was washed with water (2×100 ml), brine (1×100 ml), dried (Na$_2$SO$_4$) and concentrated. The crude product was triturated with petrol ether to give the product as white solid.

Yield: 500 mg (94%). Rf: 0.25 (70% ethylacetate in petrol). M.pt. 180° C. IR ν (cm$^{-1}$): 3294, 3235, 2927, 1697, 1615, 1570, 1373, 1358, 1274, 1188, 1041, 935, 816, 756. $^1$H-NMR Spectrum: δ$_H$ (300 MHz, CDCl$_3$) 7.60 (1H, d, J=6.7 Hz, Ar), 7.37 (2H, m, Ar), 7.23 (5H, m, Ar), 6.63 (1H, br, —OH), 6.74 (1H, br, —NH), 3.99 (1H, m, —N—CH$_2$), 3.82 (1H, dt, J=3.3 & 11.3 Hz, —N—CH$_2$), 2.93 (1H, m, —N—CH$_2$), 2.80 (1H, dt, J=2.8 & 14.0 Hz, —N—CH$_2$), 1.73 (3H, s, —CH$_3$). $^{13}$C-NMR Spectrum: δ$_C$ (75 MHz, CDCl$_3$) 23.37, 39.21, 40.72, 91.91, 123.18, 123.29, 123.54, 127.94, 129.18, 129.69, 129.87, 133.47, 134.77, 138.13, 149.87, 169.14, 173.08. LC-MS (in MeOH): 6.32 min. M$^+$ Na: 367.05. M$^+$ —OH 327.02.

N-{2-[1-(4-tert-Butylbenzyloxy)-1-(4-chlorophenyl)-3-oxo-1,3-dihydroisoindolin-2-yl]-ethyl}-acetamide (dNU8228)

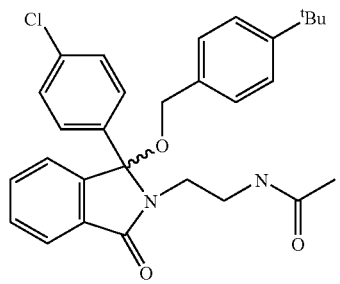

To a stirred solution of N-{2-[1-(4-chlorophenyl)-1-hydroxy-3-oxo-1,3-dihydroisoindolin-2-yl]-ethyl}acetamide (150 mg, 0.435 mmol) in 10 Ml of dry THF, thionyl chloride (77 mg, 0.652 mmol) was added followed by three drops of dry DMF at room temperature under nitrogen atmosphere. The progress of the reaction was monitored by TLC. After 30 min. the TLC showed the completion of the reaction. The solvent was evaporated to dryness under reduced pressure and the residue was dissolved in THF (10 Ml). 4-tert-butyl alcohol (85 mg, 0.522 mmol) was added at room temperature followed by triethylamine (88 mg, 0.87 mmol). After 30 min. the solvent was evaporated and the residue was dissolved in ethylacetate (100 ml). The organic layer was washed with water (2×100 ml), brine (1×100 ml), dried (Na$_2$SO$_4$) and concentrated. The crude product was purified by column chromatography using 50-100% ethylacetate in petrol.

White solid. M. Pt: 72° C. R$_f$: 0.25 (80% ethylacetate/petrol). IR: ν (cm$^{-1}$): 3294(b), 2954(m), 2871(m), 1697(s), 1657(s), 1543(s), 1466(m), 1368(s), 1276(m), 1048(m), 1011 (m), 817(s), 763(s). $^1$H-NMR Spectrum: δ$_H$ (300 MHz, CDCl$_3$) 7.87-7.82 (1H, m, Ar), 7.51-7.42 (2H, m, Ar), 7.31-7.18 (6H, m, Ar), 7.15-7.07 (3H, m, Ar), 6.74 (1H, br, —NH), 4.06 (1H, d, J=9.0 Hz, —OCH$_2$—), 3.90 (1H, d, J=9.0 Hz, —OCH$_2$—), 3.46 (1H, m, —N—CH$_2$—), 3.28 (2H, m, —N—CH$_2$—), 3.05 (1H, m, —N—CH$_2$—), 1.82 (3H, s, —CH$_3$), 1.23 (9H, s, tBu). $^{13}$C-NMR Spectrum: δ$_C$ (75 MHz, CDCl$_3$): 23.58, 31.71, 34.97, 39.53, 40.53, 65.45, 95.37, 123.73, 124.09, 125.88, 127.75, 128.16, 129.10, 129.33, 130.58, 131.52, 133.45, 133.57, 134.04, 135.29, 137.23, 145.59, 151.48, 170.30, 170.69. LC/MS (in MeOH): Tr=7.82 min, M+Na=513.19, 515.19.

Analysis calculated for C, 70.94; H, 6.36; N, 5.71; Found: C, 69.48; H, 6.23; N, 5.55.

N-{2-[1-(4-Chlorophenyl)-1-(4-hydroxy-3,5-dimethoxybenzyloxy)-3-oxo-1,3-dihydroisoindolin-2-yl]-ethyl}acetamide (NU8227)

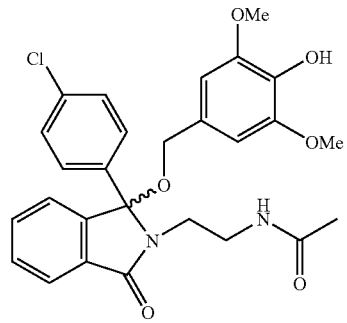

To a stirred solution of SA149 (150 mg, 0.435 mmol) in 10 Ml of dry THF, thionyl chloride (77 mg, 0.652 mmol) was added followed by three drops of dry DMF at room temperature under nitrogen atmosphere. The progress of the reaction was monitored by TLC. After 30 min. the TLC showed the completion of the reaction. The solvent was evaporated to dryness under reduced pressure and the residue was dissolved in THF (10 Ml). Syringic alcohol (176 mg, 0.957 mmol) was added at 0° C. After 30 min. the solvent was evaporated and the residue was dissolved in ethylacetate (100 ml). The organic layer was washed with water (2×100 ml), brine (1×100 ml), dried ($Na_2SO_4$) and concentrated. The crude product was purified by column chromatography using 50-100% ethylacetate in petrol.

Light pink powder. M. Pt: 84° C. $R_f$: 0.21 (80% ethylacetate/petrol). IR: ν ($cm^1$): 3300(b), 2938(m), 1674(s), 1517(s), 1450(s), 1372(s), 1211(s), 1087(s), 816(s), 690(s). $^1$H-NMR Spectrum: $δ_H$ (300 MHz, $CDCl_3$): 7.87-7.82 (1H, Ar), 7.49-7.46 (2H, Ar), 7.28-7.19 (4H, Ar), 7.11-7.06 (1H, Ar), 6.71 (1 h, —NH), 6.39 (2H, s, Ar), 5.60 (1H, br, —OH), 4.02 (1H, d, J=10.8 Hz, —$OCH_2$), 3.86 (1H, d, J=10.8 Hz, —$OCH_2$), 3.47 (1H, m, —N—$CH_2$—), 3.27 (2H, m, —N—$CH_2$—), 3.07 (1H, m, —N—$CH_2$—), 1.84 (3H, s, —$CH_3$). $^{13}$C-NMR Spectrum: $δ_C$ (75 MHz, $CDCl_3$): 23.59, 39.42, 40.54, 56.78, 66.22, 95.44, 105.30, 123.83, 124.07, 127.94, 128.09, 129.14, 129.37, 130.58, 131.52, 133.52, 135.05, 135.34, 137.17, 145.61, 147.44, 170.26, 170.74. LC/MS (in MeOH): Tr=6.44 min, M+Na=533.21, 535.22. Analysis calculated for C, 63.47; H, 5.33; N, 5.48; Found: C, 62.60; H, 5.89; N, 5.06.

2-Benzyl-3-(4-hydroxy-3,5-dimethoxybenzyloxy)-3-phenyl-2,3-dihydro-isoindolin-1-one (NU8205)

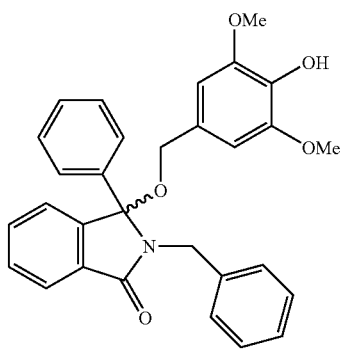

To a stirred solution of 2-benzyl-3-hydroxy-3-phenyl-2,3-dihydro-isoindolin-1-one (200 mg, 0.635 mmol) in 10 Ml of THF, thionyl chloride was added followed by three drops of dry DMF at room temp. under nitrogen atmosphere. The progress of the reaction was monitored by TLC using the aliquot of the reaction mixture in methanol. After completion of the reaction, the solvent was evaporated to dryness under reduced pressure and the residue was dissolved in THF (10 Ml). The reaction mixture was cooled to 0° C. using ice bath. After 15 min. syringic alcohol (258 mg, 1.40 mmol) was added at once and stirred for overnight. The solvent was evaporated and the crude product was purified by column chromatography using 30-60% ethylacetate in petrol. White solid. M. Pt: 55° C. Rf: 0.28 (40% ethylacetate/petrol). IR: ν ($cm^1$):3506 (m), 2936 (m), 1693 (s), 1608 (m), 1516 (m), 1458 (s), 1427 (m), 1381 (s), 1327 (s), 1210 (s), 1107 (s), 760 (s). $^1$H-NMR Spectrum: $δ_H$ (500 MHz, $CDCl_3$): 7.86 (1H, d, J=7.3 Hz, Ar), 7.38 (2H, m, Ar), 7.28 (2H, m, Ar), 7.23 (2H, d, J=6.1 Hz, Ar), 7.18 (3H, m, Ar), 7.06 (4H, m, Ar), 6.06 (2H, s, Ar), 5.48 (1H, bs, —OH), 4.74 (1H, d, J=7.4 Hz, —$CH_2$-Ph), 3.95 (1H, d, J=7.4 Hz, —$CH_2$-Ph), 3.72 (6H, s, —$OCH_3$), 3.58 (2H, q, J=10.6 Hz & 30.9 Hz, —O—$CH_2$—). $^{13}$C-NMR Spectrum: $δ_C$ (125 MHz, $CDCl_3$): 168.25, 146.64, 145.74, 138.44, 137.52, 134.19, 132.45, 131.61, 129.53, 129.29, 128.36, 128.05, 126.98, 126.38, 123.45, 123.09, 104.69, 95.62, 65.18, 56.21, 43.29. LC/MS (in MeOH): Tr=6.92. M+Na=504.18, 505.19. Analysis calculated for C, 74.83; H, 5.65; N, 2.91; Found: C, 74.34; H, 5.72; N, 2.68.

4-trimethylsilanylethoxymethoxy-benzonitrile

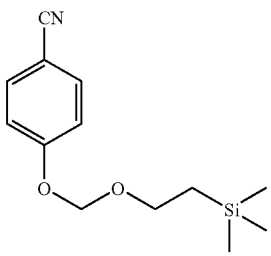

To a solution of 1.63 ml (9.23 mmol) of SEM-Cl in 10 ml of dry DCM were added 1.00 g (8.39 mmol) of 4-hydroxy benzonitrile, 103 mg (0.84 mmol) of DMAP and 2.34 ml (16.8 mmol) of $Et_3N$, stirring at RT under $N_2$. After stirring overnight, 10 ml of ether were added and the solids filtered off. The filtrate was evaporated and the product purified by flash chromatography (20% ethyl acetate in petrol), obtaining 945 mg (3.79 mmol, 48%) of a colourless oil.

$^1$H-NMR $δ_H$ (200 MHz, $CDCl_3$) ppm 0.00 (s, 9H, $CH_3$), 0.95 (m, 2H, $CH_2$Si), 3.75 (m, 2H, $CH_2$O), 5.27 (s, 2H, $OCH_2$O), 7.10 (d, 2H, Ar), 7.59 (d, 2H, Ar).

General Procedure for the Preparation of Isoindolinones from Aromatic Amides, Using the $^s$BuLi/TMEDA System.

In a typical example, 6.13 mmol of amide and 1.85 ml (12.3 mmol) of TMEDA were dissolved in 20 ml of dry THF, stirring at −78° C. under $N_2$. Then 9.4 ml (12.3 mmol) of 1.3M $^s$BuLi were added dropwise over 30 min. After stirring at −78° C. for 30 min, 6.44 mmol of the required benzonitrile in 5 ml of dry THF were added dropwise. The mixture was then stirred at −78° C. for 30 min and at −30° C. for 20 min. The resulting orange-red solution was quenched with a 5% sol. of $NH_4Cl$ and the aqueous layer was extracted twice with ethyl acetate. The combined organic extracts were washed with brine, dried over $MgSO_4$ and evaporated, to give a residue which was purified by flash chromatography (ethyl acetate in petrol, gradient from 20% to 50%).

2-Propyl-3-amino-3-(4-trimethylsilanylethoxymethoxyphenyl)-isoindolinone

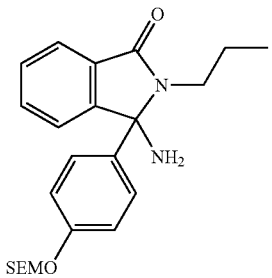

4-trimethylsilanylethoxymethoxy-benzonitrile was used as the starting benzonitrile. Colourless oil, 58%. $R_f$ 0.40 (50:50; ethylacetate:petrol)

IR ν (cm$^{-1}$): 3307, 1678; ES-MS m/z 413, 396, 296; $^1$H-NMR δ$_H$ (500 MHz, CDCl$_3$) ppm 0.00 (s, 9H, CH$_3$), 0.90 (t, 3H, CH$_3$; J=7.4 Hz), 0.96 (m, 2H, CH$_2$Si), 1.55 (m, 2H, CH$_2$), 2.14 (bs, 2H, NH$_2$), 3.00 (ddd, 1H, CH$_2$N; J=6.1, 10.0, 14.1 Hz), 3.52 (ddd, 1H, CH$_2$N; J=5.8, 10.0, 14.1 Hz), 3.75 (m, 2H, CH$_2$O), 5.21 (s, 2H, OCH$_2$O), 6.99 (d, 2H, Ar; J=8.8 Hz), 7.33 (m, 3H, Ar), 7.44 (m, 2H, Ar), 7.83 (m, 1H, Ar); $^{13}$C-NMR δ$_C$ (128 MHz, CDCl$_3$) ppm −1.4, 11.9, 18.0, 22.6, 41.3, 66.3, 79.8, 92.8, 116.3, 122.4, 123.2, 123.3, 127.5, 128.8, 130.7, 132.15, 132.19, 133.1, 150.7, 157.4, 167.8.

General Procedure for the acylation of 3-amino-isoindolinones.

In a typical example, to 0.75 mmol of 3-amino-isoindolinone in 2 ml of dry DCM were added, stirring at RT under N$_2$, 0.30 ml (2.25 mmol) of Et$_3$N and 1.50 mmol of the required benzoyl chloride. The reaction was followed by TLC, with typical reaction times of 24-48 h. When the reaction was judged to be complete, the mixture was diluted with 1 vol. of DCM, washed with 1N HCl, brine, dried over MgSO$_4$ and evaporated. The residue was then purified by flash chromatography (25% ethyl acetate in petrol). Analitically pure samples were obtained by further recrystallization from ethyl acetate/petrol.

2-Propyl-3-(4-trimethylsilanylethoxymethoxy-phenyl)-3-(4-$^t$Bu-benzamido)-isoindolin-1-one (NU8104)

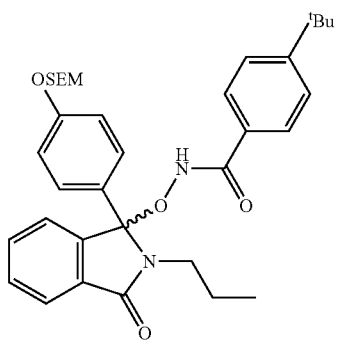

White solid, 65%. R$_f$ 0.70 (40:60; ethylacetate:petrol)
Mp: 151° C.; IR ν (cm$^{-1}$): 3281, 1682, 1678; ES-MS m/z 573, 396, 338; $^1$H-NMR δ$_H$ (500 MHz, CDCl$_3$) ppm 0.01 (s, 9H, SiMe$_3$), 0.85 (t, 3H, CH$_3$; J=7.3 Hz), 0.96 (m, 2H, CH$_2$Si), 1.34 (s, 9H, $^t$Bu), 1.50 (m, 1H, CH$_2$), 1.63 (m, 1H, CH$_2$), 3.22 (ddd, 1H, CH$_2$N; J=5.2, 10.4, 14.0 Hz), 3.63 (ddd, 1H, CH$_2$N; J=5.8, 10.6, 14.0 Hz), 3.74 (m, 2H, CH$_2$O), 5.21 (s, 2H, OCH$_2$O), 6.98 (s, NH), 7.06 (m, 2H, Ar), 7.41 (m, 7H, Ar), 7.74 (m, 2H, Ar), 7.84 (m, 1H, Ar); $^{13}$C-NMR δ$_C$ (128 MHz, CDCl$_3$) ppm −1.3, 11.9, 18.2, 22.0, 31.4, 35.1, 42.6, 66.5, 79.3, 92.9, 117.0, 122.2, 123.6, 125.9, 126.6, 127.0, 128.9, 131.0, 131.3, 131.7, 132.2, 148.1, 155.9, 158.0, 166.3, 168.7. Analysis for C$_{34}$H$_{44}$N$_2$O$_4$Si: calcd. C, 71.29; H, 7.74; N, 4.89; found C, 71.30; H, 7.55; N, 4.82.

3-Benzylsulfanyl-3-(4-chlorophenyl)-2-propylisoindolin-1-one

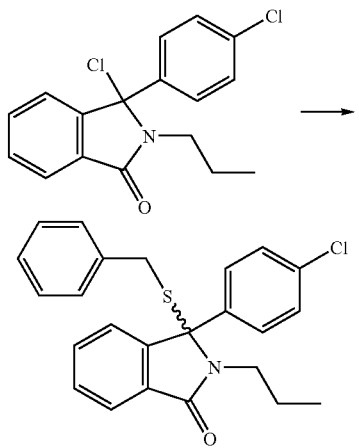

Distilled THF was added to 3-chloro-3-(4-chlorophenyl)-2-propylisoindolin-1-one (1.06 g, 3.31 mmol) followed by benzyl mercaptan (0.855 mL, 7.29 mmol) as for general procedure C. On addition of the benzyl mercaptan, a pale pink precipitate formed which turned white over time. The ethyl acetate was mostly removed under vacuum. On leaving overnight in the fridge, clear crystals formed. The crude product was purified by flash column chromatography (20:80, EtOAc:petrol) and recrystallised in the minimum amount of hot ethyl acetate giving large colourless crystals of 3-benzylsulfanyl-3-(4-chlorophenyl)-2-propyl-2,3-dihydroisoindolin-1-one (918 mg, 2.25 mmol, 68%). R$_f$ 0.68 (40:60 EtOAc:petrol). Mp. 131.5-133.4° C. λ$_{max}$ (CH$_3$OH)/nm 223.0, Abs 0.964. IR: 3161, 2968, 1665, 1608, 1467, 1435, 1402 cm$^{-1}$. $^1$H NMR (300 Hz, CDCl$_3$); δ 0.72 (t, 3H, J=7.5 Hz, N (CH$_2$)$_2$—CH$_3$), 1.37 (m, 1H, N—CH$_2$—CH$_2$—CH$_3$), 1.57 (m, 1H, N—CH$_2$—CH$_2$—CH$_3$), 2.80 (d, 1H, J=12 Hz, S—CH$_2$), 3.10 (d, 1H, J=12 Hz, S—CH$_2$), 3.17 (m, 1H, N—CH$_2$), 3.36 (m, 1H, N—CH$_2$), 6.92-7.81 (m, 13H, Ar). $^{13}$C NMR (75 Hz, CDCl$_3$); 111.8 (N—(CH$_2$)$_2$—CH$_3$), 21.5 (N—CH$_2$—CH$_2$), 33.4 (S—CH$_2$), 42.6 (N—CH$_2$), 78.2 (S—C—N), 123.2, 123.4, 127.3, 128.0, 128.5, 128.9, 128.9, 131.0, 132.8, 134.9, 135.8, 137.1, 148.3 (Ar), 167.9 (C=O). LC/MS-ES$^+$ m/z 410.6, 408.7, 286.1, 287.1. Anal. Calcd. for C$_{24}$H$_{22}$ClNOS: C, 70.66; H, 5.44; N, 3.43%. Found C, 70.60; H, 5.51; N, 3.51%.

3-(4-Chlorophenyl)-3-(3-hydroxycyclopentyloxy)-2-propylisoindolin-1-one (NU8253)

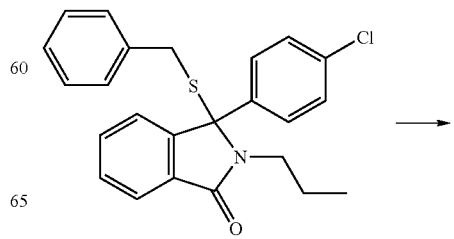

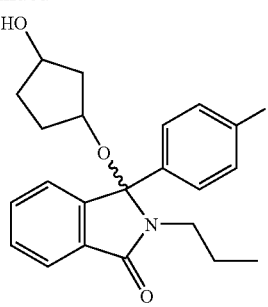

3-Benzylsulfanyl-3-(4-chlorophenyl)-2-propylisoindolin-1-one (200 mg, 0.490 mmol.) was reacted with NIS (121 mg, 0.539 mmol.), CSA (11 mg, 0.049 mmol.) and 1,3-cyclopentanediol (0.229 mL, 2.45 mmol.). The reaction was kept in the dark and stirred for 4 hours at room temperature and monitored by TLC. The solvent was then removed under vacuum, and the product taken up into ethyl acetate (30 mL), washed with sodium thiosulfate solution (2×20 mL), brine (20 mL) and dried with $Na_2SO_4$. The solvent was removed to give a pale yellow oil of 3-(4-chlorophenyl)-3-(3-hydroxycyclopentyloxy)-2-propylisoindolin-1-one. This was purified by HPLC to give colourless oil (111 mg, 0.288 mmol, 59%). $R_f$ 0.14 (40:60 EtOAc:petrol). $\lambda_{max}$ ($CH_3OH$)/nm 224.0, Abs 0.608. IR: 3400, 2967, 1685, 1601, 1466 cm$^{-1}$. $^1$H NMR (300 Hz, CDCl$_3$); δ 0.70 (t, 3H, J=7.0 Hz, N(CH$_2$)$_2$—CH$_3$), 1.10-1.25 (m, 2H, N—CH$_2$—CH$_2$—CH$_3$), 1.35-1.44 (m, 2H, cyclopentane C—H), 1.60-1.67 (m. 2H, cyclopentane C—H), 1.78-1.99 (m, 2H, cyclopentane C—H), 3.02 (m, 1H, N—CH$_2$), 3.16 (m, 1H, N—CH$_2$), 3.82 (m, 1H, HO—C—H), 4.31 (m, 1H, C—O—C—H), 7.02-7.43 (m, 7H, Ar), 7.79 (d, 1H, J=7.9 Hz, Ar). $^{13}$C NMR (75 Hz, CDCl$_3$): 12.2 (N—(CH$_2$)$_2$—CH$_3$), 21.8, 21.9, 22.6 (N—CH$_2$—CH$_2$), 31.6, 31.8, 32.1, 32.2, 32.7, 33.7, 33.8, 33.9, 34.3, 41.6, 41.8, 41.9, 43.6, 44.1, 45.7 (N—CH$_2$ and cyclopentane C), 72.2, 72.6, 72.7, 72.9, 73.0, 73.2, 73.8, 73.9, 74.4 (cyclopentane C—O), 94.7, 94.8 (quaternary O—C—N), 122.9, 123.7, 124.0, 124.1, 124.2, 124.3, 128.2, 128.2, 128.3, 128.8, 129.1, 129.9, 130.1, 130.2, 130.2, 132.3, 132.6, 132.7, 132.9, 134.6, 134.7, 138.1, 138.5, 146.3, 146.4, 146.5, 149.2 (Ar), 168.6, 168.7, 168.7 (C=O). LC/MS-ES$^+$ m/z 388.3, 386.3, 284.1, 286.1, 245.0, 243.0. Anal. Calcd. for $C_{22}H_{24}ClNO_3$: C, 68.48; H, 6.27; N, 3.63%. Found C, 68.05; H, 6.26; N, 3.67%. HRMS (EI) m/z: 385.1444. Found 385.1449.

3-(4-Chlorophenyl)-3-hydroxy-2-phenethylisoindolin-1-one

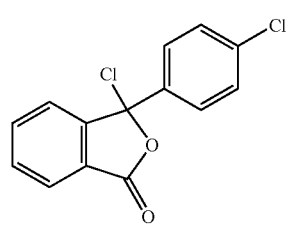

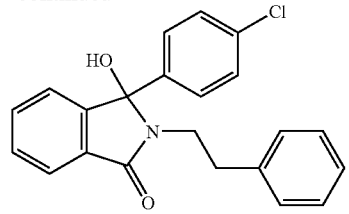

Distilled THF (50 mL) was added to 3-chloro-3-(4-chlorophenyl)isobenzofuran-1(3H)-one (5.36 g, 19.2 mmol) followed by phenethylamine (2.65 mL, 21.1 mmol) and triethylamine (3.21 mL, 23.0 mmol) as for general procedure A and recrystallised in acetonitrile to give pure white solid 3-(4-chlorophenyl)-3-hydroxy-2-phenethylisoindolinin-1-one (4.82 g, 13.3 mmol. 69%). $R_f$ 0.43 (40:60 EtOAc:petrol). Mp. 165.5-167.3° C. $\lambda_{max}$ ($CH_3OH$)/nm 226.5, Abs 0.759. IR: 3255, 1734, 1680, 1601, 1493, 1470 cm$^{-1}$. $^1$H NMR (300 Hz, DMSO); δ 2.64 (dt, 1H, J=11.1 Hz, 5.5 Hz, N—CH$_2$—CH$_2$—Ar), 2.82 (dt, 1H, J=10.1 Hz, 5.1 Hz, N—CH$_2$—CH$_2$—Ar) 3.12 (m, 1H, N—CH$_2$), 3.53 (m, 1H, N—CH$_2$), 7.10 (d, 2H, J=6.8 Hz Ar—H), 7.18-7.43 (m, 8H, Ar—H), 7.56 (m, 2H, Ar—H), 7.75 (m, 1H, Ar). $^{13}$C NMR (75 Hz, DMSO); δ 34.9 (N—(CH$_2$—CH$_2$—Ar), 41.0 (N—CH$_2$—CH$_2$), 90.5 (quaternary CO(Ar)N), 122.9, 123.1, 126.6, 128.3, 128.7, 128.8, 128.9, 129.8, 130.8, 133.0, 133.2, 139.4, 139.5, 149.5 (Ar), 166.8 (C=O). LC/MS-ES$^+$ m/z 143.0, 111.0. Anal. Calcd. for $C_{22}H_{18}ClNO_2$: C, 72.62; H, 4.99; N, 3.85%. Found C, 72.42; H, 5.04; N, 3.96%.

3-(4-Chlorophenyl)-3-(3-hydroxycyclopentyloxy)-2-phenethylisoindolin-1-one (NU8257)

3-(4-Chlorophenyl)-3-hydroxy-2-phenethylisoindolin-1-one (250 mg, 0.687 mmol.) was reacted with thionyl chloride (0.055 mL, 0.756 mmol.) and a catalytic amount of DMF as for general procedure B, and the solvent removed to give a colourless oil of the crude 3-chloro-3-(4-chlorophenyl)-2-phenethylisoindolin-1-one (256 mg, 0.687 mmol., 100%).

3-Chloro-3-(4-chlorophenyl)-2-phenethylisoindolin-1-one (256 mg, 0.687 mmol) was reacted with 1,3-cyclopentanediol (0.32 mL, 3.44 mmol.) as for general procedure F and the solvent evaporated under vacuum to leave a clear oil of 3-(4-chlorophenyl)-3-(3-hydroxycyclopentyloxy)-2-phenethylisoindolin-1-one. This was purified by HPLC (76.0 mg, 0.170 mmol., 25%). R$_f$ 0.13 (40:60 EtOAc:petrol). IR: 2359, 1958, 1684, 1601, 1491, 1464 cm$^{-1}$. $^1$H NMR (300 Hz, CDCl$_3$); δ 0.95-2.04 (m, 6H, cyclopentanediol C—H), 2.24 (m, 1H, N—CH$_2$—CH$_2$—Ar), 2.81 (m, 1H, N—CH$_2$—CH$_2$—Ar), 3.19 (m, 1H, N—CH$_2$), 3.42 (m, 1H, N—CH$_2$), 3.70-3.83 (m, 1H, HO—C—H), 4.32 (m, 0.5H, C—O—C-h), 4.43 (m, 0.5H, C—O—C—H), 6.95-7.23 (m, 11H, Ar), 7.45 (m, 2H, Ar), 7.81 (m, 1H, Ar). $^{13}$C NMR (75 Hz, CDCl$_3$); δ 31.7, 31.9, 32.2, 33.7, 33.9, 34.0, 34.6, 32.7, 35.2 (cyclopentane C), 41.6, 41.7, 41.8, 42.0, 42.1, 43.7, 44.1, 45.7, 50.9 (N—CH$_2$—CH$_2$) 72.3, 72.6, 73.0, 73.2, 73.9, 74.0 (cyclopentane C—O), 94.6, 94.7 (quaternary O—C—N), 123.0, 123.8, 123.9, 124.1, 124.2, 126.8, 128.1, 128.3, 128.4, 128.5, 128.9, 129.0, 129.1, 129.2, 129.2, 130.4, 130.4, 130.4, 132.8, 133.1, 134.9, 137.8, 137.8, 138.3, 139.3, 146.3, 146.3, 149.1 (Ar), 168.4, 168.6, 168.7 (C=O). LC/MS-ES$^+$ m/z 480.2, 478.1, 458.1, 456.1, 293.0. Anal. Calcd. for C$_{28}$H$_{22}$ClNO$_3$.0.25H$_2$O: C, 73.04; H, 4.93; N, 3.04%. Found C, 73.24; H, 5.00; N, 3.22%. HRMS (EI) m/z: 455.1288. Found 455.1297.

2-(4-Chlorobenzyl)-3-(4-chlorophenyl)-3-hydroxy-isoindolin-1-one

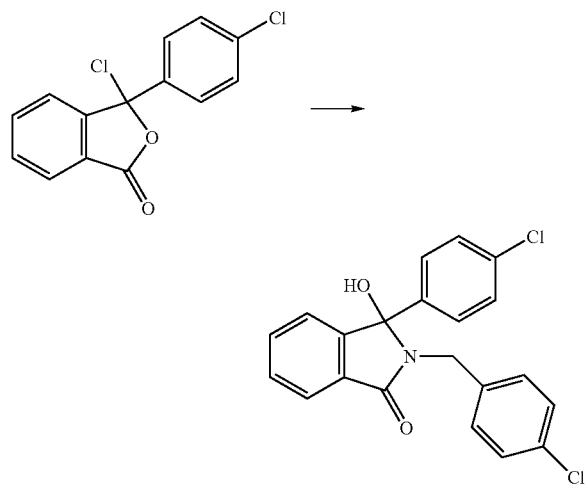

Distilled THF (50 mL) was added to 3-chloro-3-(4-chlorophenyl)isobenzofuran-1(3H)-one (1.50 g, 5.76 mmol) followed by 4-chlorobenzylamine (0.77 mL, 6.34 mmol) and triethylamine (0.96 mL, 6.91 mmol) as for general procedure A and recrystallised in acetonitrile to give pure white solid 2-(4-chlorobenzyl)-3-(4-chlorophenyl)-3-hydroxyisoindolin-1-one (945 mg, 2.46 mmol. 43%). R$_f$ 0.54 (40:60 EtOAc: petrol). Mp. 156.5-157.4° C. λ$_{max}$ (CH$_3$OH)/nm 221.0, Abs 0.850. IR: 3159, 1659, 1487, 1468 cm$^{-1}$. $^1$H NMR (300 Hz, CDCl$_3$); δ 3.07 (s, br, 1H, OH), 4.01 (d, 1H, J=15.0 Hz, N—CH$_2$), 4.52 (d, 1H, J=15.0 Hz, N—CH$_2$), 7.05 (m, 4H, Ar—H), 7.16-7.21 (m, 5H, Ar—H), 7.42 (m, 2H, Ar—H), 7.73 (m, 1H, Ar—H). $^{13}$C NMR (75 Hz, DMSO); δ 42.6 (N—CH$_2$), 91.5 (Ar$_2$(O)CN), 123.1, 124.0, 128.2, 128.7, 129.1, 130.4, 130.6, 133.4, 133.5, 135.0, 136.8, 137.0, 148.8 (Ar), 168.0 (C=O). LC/MS-ES$^+$ m/z 406.1, 366.0, 244.9, 242.9, 161.0. Anal. Calcd. for C$_{21}$H$_{15}$Cl$_2$NO$_2$.0.2H$_2$O: C, 65.03; H, 4.00; N, 3.61%. Found C, 65.08; H, 4.06; N, 3.88%. HRMS (EI) m/z: 244.0291. Found 244.0299.

2-(4-Chlorobenzyl)-3-(4-chlorophenyl)-3-(3-hydroxycyclopentyloxy)isoindolin-1-one (NU8274)

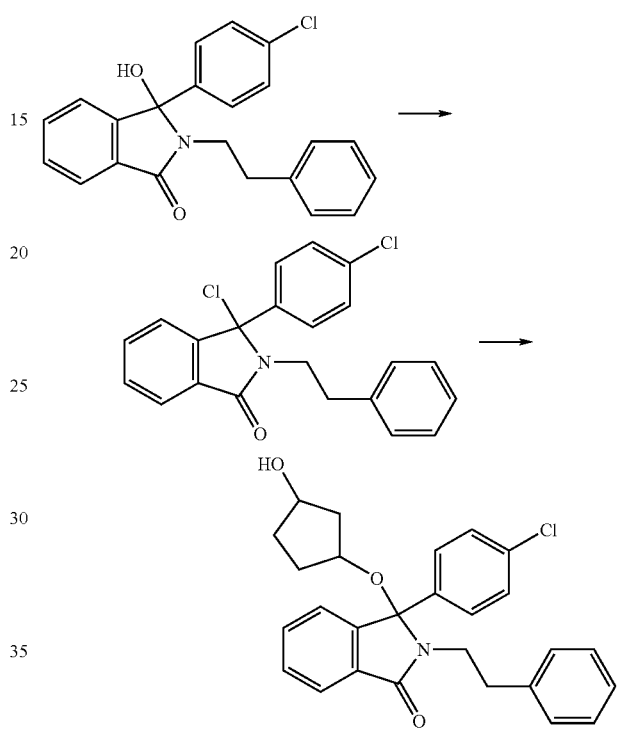

2-(4-Chlorobenzyl)-3-(4-chlorophenyl)-3-hydroxyisoindolinone (150 mg, 0.390 mmol.) was reacted with thionyl chloride (0.031 mL, 0.429 mmol.) and a catalytic amount of DMF as for general procedure B, and the solvent removed to give a colourless oil of the crude 3-chloro-2-(4-chlorobenzyl)-3-(4-chlorophenyl)isoindolin-1-one (157 mg, 0.390 mmol., 100%).

3-Chloro-2-(4-chlorobenzyl)-3-(4-chlorophenyl) isoindolin-1-one (157 mg, 0.390 mmol) was reacted with 1,3-cyclopentanediol (0.18 mL, 1.95 mmol.) as for general procedure C and the solvent evaporated under vacuum to leave a clear oil of crude 2-(4-chlorobenzyl)-3-(4-chlorophenyl)-3-(3-hydroxycyclopentyloxy)isoindolin-1-one. This was purified by HPLC to give the pure product which was a clear glass (83 mg, 0.177 mmol., 45%). R$_f$ 0.08 (40:60 EtOAc:petrol). λ$_{max}$ (CH$_3$OH)/nm=220.5 (Abs=1.333). IR: 3426, 2935, 1696, 1695, 1597, 1489, 1467 cm$^{-1}$. $^1$H NMR (300 Hz, DMSO); δ1.03-1.86 (m, 6H, cyclopentanediol C—H), 2.02 (m, 1H, N—CH$_2$), 3.48-3.75 (M, 1H, N—CH$_2$), 4.00-4.50 (m, 2H, cyclopentanediol O—C—H), 6.66-7.15 (m, 9H, Ar—H), 7.32-7.53 (m, 2H, Ar—H), 7.83 (m, 1H, Ar—H). $^{13}$C NMR (75 Hz, DMSO); δ 31.4 (N—CH$_2$), 32.1, 33.8, 34.0, 42.9, 44.1 (cyclopentanediol), 95.0 (Ar$_2$C(O)—N), 72.1, 73.0 (cyclopentanediol C—OH), 124.0, 124.3, 128.5, 128.6, 130.2, 130.8, 130.8, 132.7 (Ar). LC/MS-ES$^+$ m/z 470.3, 468.3, 245.1, 243.1. Anal. Calcd. for C$_{26}$H$_{23}$Cl$_2$NO$_3$.0.4H$_2$O: C, 65.66; H, 5.04; N, 2.95%. Found C, 65.49; H, 4.94; N, 3.02%. HRMS (EI) m/z: 467.1055. Found 467.1055.

2-Benzyl-3-(4-chlorophenyl)-3-(3-hydroxycyclopentyloxy)-2,3-dihydroisoindolin-1-one (NU8249)

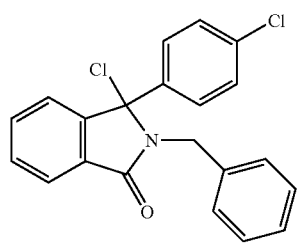

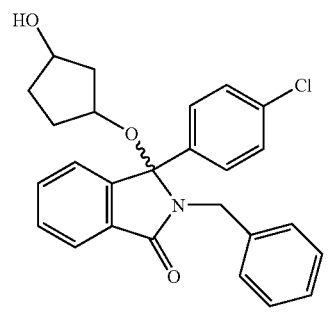

2-Benzyl-3-chloro-3-(4-chlorophenyl)-2,3-dihydroisoindolin-1-one (209 mg, 0.57 mmol) was reacted with 1,3-cyclopentanediol (0.26 mL, 2.85 mmol) as for general procedure C. The crude product was purified by HPLC(H$_2$O: MeOH, 270 nm) to give 2-benzyl-3-(4-chlorophenyl)-3-(3-hydroxycyclopentyloxy)-2,3-dihydroisoindolin-1-one as a clear glass (117 mg, 0.26 mmol, 63%); R$_f$=0.20 (40:60: EtOAc:petrol). $\lambda_{max}$ (CH$_3$OH)/nm 229, Abs 0.449. IR: 3362, 2934, 1683, 1489, 1464, 1388 cm$^{-1}$. $^1$H NMR: (300 MHz, d$_6$-DMSO) δ 1.09 (m, 1H, cyclopentane), 1.24 (m, 2H, cyclopentane), 1.49 (m, 2H, cyclopentane), 1.80 (m, 1H, cyclopentane), 3.71 (m, 1H, cyclopentane), 4.18 (m, 1H, cyclopentane), 4.18 (m, 1H, N—CH$_2$), 4.38 (d, 1H, J=14.8 Hz, N—CH$_2$), 7.06 (m, 10H, Ar—H), 7.14 (m, 2H, Ar—H), 7.39 (m, 2H, Ar—H), 7.42 (m, 2H, Ar—H), 7.81 (m, 1H, Ar—H).

$^{13}$C NMR: (75 MHz, d$_6$-DMSO) δ 30.7, 31, 31.1, 32, 32.1, 32.8, 33.5, 33.7, 33.9, 34.3, 42.9, 43.3, 43.4, 44.1, 45.6, 71.9, 72.6, 72.8, 73, 73.2, 73.3, 73.4, 74, 74.1, 77, 77.4, 77.8, 91.5, 95.1, 123, 123.8, 123.9, 124.3, 124.4, 127.4, 127.5, 128.2, 128.5, 128.6, 128.7, 128.9, 129.1, 129.3, 129.4, 130.1, 130.2, 131.8, 132.7, 132.7, 133.2, 134.5, 137.8, 138, 146.4, 146.5, 146.6, 149, 168, 168.8, 168.9. LC/MS-ES$^+$ m/z 242.9, 332.1, 434.1 [MH$^+$]. Anal. Calcd. for C$_{26}$H$_{24}$ClNO$_3$: C, 71.97; H, 5.57; N, 3.23%. Found C, 71.39; H, 5.40; N, 3.46%. HRMS (EI) m/z Calcd. for C$_{26}$H$_{24}$ClNO$_3$: 433.1444. Found 433.1436.

3-(4-Chlorophenyl)-3-hydroxy-2-(4-nitrobenzyl)-2,3-dihydroisoindolin-1-one

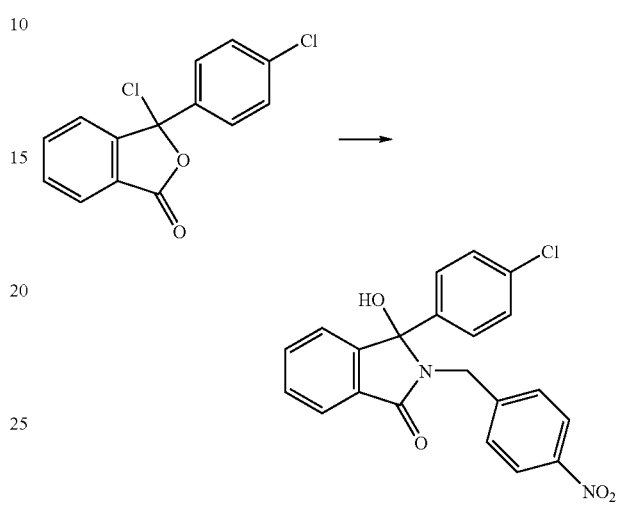

Distilled THF (25 mL) was added to 3-chloro-3-(4-chlorophenyl)-3H-isobenzofuran-1-one (3.2 g, 11.5 mmol) followed by 4-nitrobenzylamine hydrochloride (2.3 g, 12.6 mmol) and triethylamine (4.8 mL, 34.5 mmol) as for general procedure A. The crude product was recrystallised in the minimum amount of boiling ethyl acetate to give 3-(4-chlorophenyl)-3-hydroxy-2-(4-nitrobenzyl)-2,3-dihydroisoindolin-1-one as a light yellow solid (2.95 g, 7.47 mmol, 65%); R$_f$=0.4 (40:60:EtOAc:petrol). 197.1-199.7° C. $\lambda_{max}$ (CH$_3$OH)/nm 220, Abs 0.765. IR: 3215, 1676, 1517, 1395, 1341 cm$^{-1}$. $^1$H NMR: (300 MHz, d$_6$-DMSO) δ 4.35 (d, 1H, J=16.3 Hz, N—CH$_2$), 4.61 (d, 1H, J=16.3 Hz, N—CH$_2$), 7.28 (m, 4H, Ar—H), 7.45 (m, 3H, Ar—H), 7.58 (m, 2H, Ar—H), 7.79 (m, 1H, Ar—H), 8.05 (m, 2H, Ar—H). $^{13}$C NMR: (75 MHz, d$_6$-DMSO) δ 42.1, 90.5, 123.1, 123.3, 128.4, 128.7, 129.1, 129.9, 130.3, 133.2, 133.3, 138.9, 146.4, 146.5, 149.4, 167.1. LC/MS-ES$^+$ m/z 307.2, 368.2, 377.1. Anal. Calcd. for C$_{21}$H$_{15}$ClN$_2$O$_4$: C, 63.89; H, 3.83; N, 7.10%. Found C, 63.78; H, 3.92; N, 7.12%. HRMS (EI) m/z Calcd. for C$_{21}$H$_{15}$ClN$_2$O$_4$: 394.0720. Found 394.0714.

3-Chloro-3-(4-chlorophenyl)-2-(4-nitrobenzyl)-2,3-dihydroisoindolin-1-one

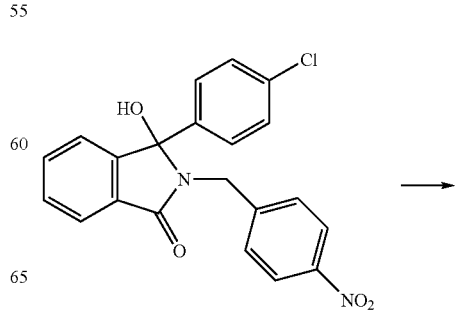

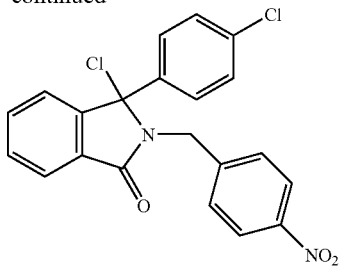

3-(4-Chlorophenyl)-3-hydroxy-2-(4-nitrobenzyl)-2,3-dihydroisoindolin-1-one (150 mg, 0.37 mmol) was reacted with thionyl chloride (0.03 mL, 0.45 mmol) and a catalytic amount of DMF (3 drops) as for general procedure B. Removal of the solvent gave 3-chloro-3-(4-chlorophenyl)-2-(4-nitrobenzyl)-2,3-dihydroisoindolin-1-one as a colourless oil (156 mg, 0.37 mmol, 100%).

3-(4-Chlorophenyl)-3-(3-hydroxycyclopentyloxy)-2-(4-nitrobenzyl)-2,3-dihydroisoindolin-1-one (NU8261)

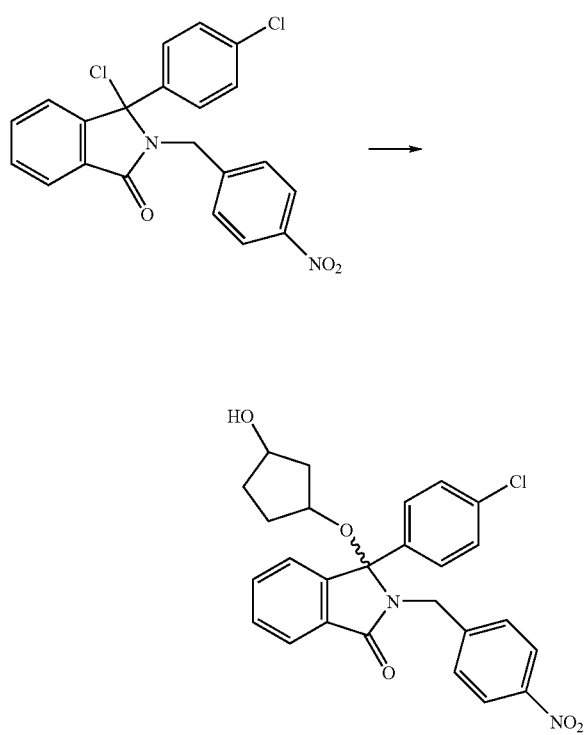

3-Chloro-3-(4-chlorophenyl)-2-(4-nitrobenzyl)-2,3-dihydroisoindolin-1-one (156 mg, 0.37 mmol) was reacted with 1,3-cyclopentanediol (0.17 mL, 1.89 mmol) as for general procedure C. The crude product was purified by HPLC ($H_2O$: MeOH, 270 nm) to give 3-(4-chloro-phenyl)-3-(3-hydroxycyclopentyloxy)-2-(4-nitrobenzyl)-2,3-dihydroisoindolin-1-one as a clear glass (94 mg, 0.19 mmol, 52%); $R_f$=0.1 (40:60:EtOAc:petrol). $\lambda_{max}$ ($CH_3OH$)/nm 230, Abs 1.513. IR: 3377, 2941, 4693, 1519, 1340, 1094 cm$^{-1}$. $^1$H NMR: (300 MHz, CDCl$_3$) δ 1.19 (m, 1H, cyclopentane), 1.35 (m, 2H, cyclopentane), 1.62 (m, 2H, cyclopentane), 1.89 (m, 1H, cyclopentane), 3.75 (m, 1H, cyclopentane), 4.26 (m, 1H, cyclopentane), 4.31 (m, 1H, N—CH$_2$), 4.50 (d, 1H, J=15.2 Hz, N—CH$_2$), 7.04 (m, 5H, Ar—H), 7.16 (m, 2H, Ar—H), 7.45 (m, 2H, Ar—H), 7.83 (m, 1H, Ar—H), 7.90 (m, 2H, Ar—H). $^{13}$C NMR: (75 MHz, CDCl$_3$) δ 29.8, 31.1, 31.2, 31.4, 32, 32.1, 33.6, 33.7, 33.9, 34.3, 42.5, 42.7, 43.1, 44, 45.6, 53.8, 72, 72.5, 72.7, 73, 73.3, 73.4, 74.1, 74.2, 74.4, 91.4, 94.8, 123.6, 123.7, 124, 124.1, 124.1, 124.4, 124.4, 128.3, 128.4, 128.7, 128.8, 129.1, 129.8, 130, 130.1, 130.3, 130.5, 130.5, 131.5, 133.2, 135, 137.4, 145.3, 145.3, 146.2, 147.2, 168.1, 168.7, 168.8, 168.9. LC/MS-ES$^+$ m/z 243, 377.1, 479.2 [MH$^+$], 501.1 [MNa$^+$]. Anal. Calcd. for $C_{26}H_{23}ClN_2O_5 \cdot 0.2H_2O$: C, 64.72; H, 4.89; N, 5.81%. Found C, 64.49; H, 4.90; N, 5.95%. HRMS (EI) m/z Calcd. for $C_{26}H_{23}ClN_2O_5$: 478.1295. Found 478.1286.

3-(4-Fluorophenyl)-3-hydroxy-2-propyl-2,3-dihydroisoindolin-1-one (NU8275)

Distilled THF (25 mL) was added to 3-chloro-3-(4-fluorophenyl)-3H-isobenzofuran-1-one (5.35 g, 20.4 mmol) followed by propylamine (1.85 mL, 22.5 mmol) and triethylamine (2.85 mL, 26.5 mmol) as for general procedure A. The crude product was recrystallised in the minimum amount of boiling ethyl acetate to give 3-(4-fluorophenyl)-3-hydroxy-2-propyl-2,3-dihydroisoindolin-1-one as a white solid (4.35 g, 15.2 mmol, 75%); $R_f$=0.48 (40:60: EtOAc:petrol). mp 172.3-174.6° C. $\lambda_{max}$ ($CH_3OH$)/nm 210, Abs 2.398. IR: 3231, 2965, 1673, 1602, 1504, 1407, 1223 cm$^{-1}$. $^1$H NMR: (300 MHz, d$_6$-DMSO) δ 0.75 (t, 3H, J=7.4 Hz, CH$_2$—CH$_2$—CH$_3$), 1.42 (m, 2H, N—CH$_2$—CH$_2$), 2.87 (m, 1H, N—CH$_2$), 3.14 (m, 1H, N—CH$_2$), 7.15 (m, 2H, Ar—H), 7.25 (m, 1H, Ar—H), 7.35 (m, 2H, Ar—H), 7.53 (dquin, 2H, J=7.4, 1.4 Hz, Ar—H), 7.71 (m, 1H, Ar—H). $^{13}$C NMR: (75 MHz, d$_6$-DMSO) δ 11.8, 22, 90.4, 115.4, 115.7, 122.7, 123, 128.3, 128.4, 129.5, 130.8, 132.7, 136.8, 136.9, 149.7, 160.5, 162.2, 163.7, 166.8. LC/MS-ES$^+$ m/z 161.1, 227.1, 268.1, 286.1 [MH$^+$]. Anal. Calcd. for $C_{17}H_{16}FNO_2$: C, 71.56; H, 5.65; N, 4.91%. Found C, 71.61; H, 5.70; N, 4.99%. HRMS (EI) m/z Calcd. for $C_{17}H_{16}FNO_2$: 285.1165. Found 285.1166.

3-Chloro-3-(4-fluorophenyl)-2-propyl-2,3-dihydroisoindolin-1-one

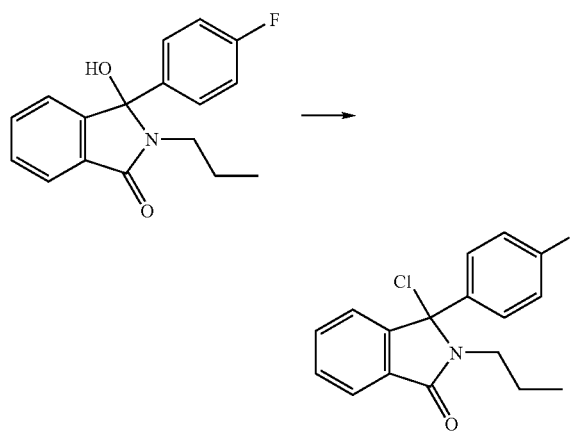

3-(4-Fluorophenyl)-3-hydroxy-2-propyl-2,3-dihydroisoindolin-1-one (200 mg, 0.7 mmol) was reacted with thionyl chloride (0.06 mL, 0.84 mmol) and a catalytic amount of DMF (3 drops) as for general procedure B. Removal of the solvent gave 3-chloro-3-(4-fluorophenyl)-2-propyl-2,3-dihydroisoindolin-1-one as a colourless oil (212 mg, 0.69 mmol, 100%).

3-(4-Fluorophenyl)-3-(3-hydroxycyclopentyloxy)-2-propyl-2,3-dihydroisoindolin-1-one (NU8279)

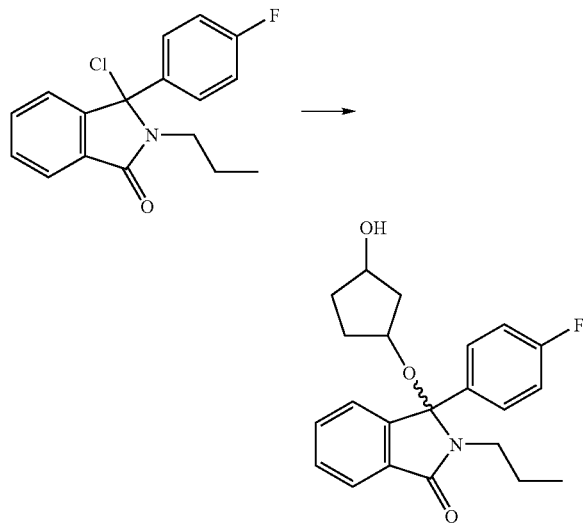

3-Chloro-3-(4-fluorophenyl)-2-propyl-2,3-dihydroisoindolin-1-one (212 mg, 0.69 mmol) was reacted with 1,3-cyclopentanediol (0.65 mL, 6.9 mmol) as for general procedure C. The crude product was purified by HPLC ($H_2O$:MeOH, 270 nm) to give 3-(4-fluorophenyl)-3-(3-hydroxycyclopentyloxy)-2-propyl-2,3-dihydroisoindolin-1-one as a clear glass (126 mg, 0.34 mmol, 49%); $R_f$=0.21 (40:60: EtOAc: petrol). $\lambda_{max}$ ($CH_3OH$)/nm 220.5, Abs 3.700. IR: 3387, 2936, 1683, 1604, 1505, 1366 $cm^{-1}$. $^1H$ NMR: (300 MHz, $d_4$-MeOH) δ 0.77 (t, 3H, J=7.4 Hz, $CH_2$—$CH_2$—$CH_3$), 1.15 (m, 1H, N—$CH_2$—$CH_2$), 1.32 (m, 1H, N—$CH_2$—$CH_2$), 1.40-2.05 (m, 6H, cyclopentane), 3.12 (m, 1H, N—$CH_2$), 3.29 (m, 1H, N—$CH_2$), 3.90 (m, 1H, cyclopentane), 4.31 (m, 1H, cyclopentane), 7.07 (t, 2H, J=9 Hz, Ar—H), 7.23 (m, 1H, Ar—H), 7.39 (m, 2H, Ar—H), 7.60 (m, 2H, Ar—H), 7.87 (m, 1H, Ar—H). $^{13}C$ NMR: (125 MHz, $d_4$-MeOH) δ 12.2, 22.9, 32.7, 33.1, 34.2, 43.1, 44.3, 44.8, 72.8, 73, 75.7, 96.5, 116.3, 116.6, 124.3, 125.7, 130, 130.1, 131.6, 133.6, 134.1, 137.1, 148.1, 166.2, 170.7. LC/MS-ES$^+$ m/z 227.1, 268.1, 370.3 [MH$^+$], 392.3 [MNa$^+$]. HRMS (EI) m/z Calcd. for $C_{22}H_{24}FNO_3$: 369.1740. Found 369.1737.

3-(4-Chlorophenyl)-2-cyclopropylmethyl-3-hydroxy-2,3-dihydroisoindolin-1-one (NU8265)

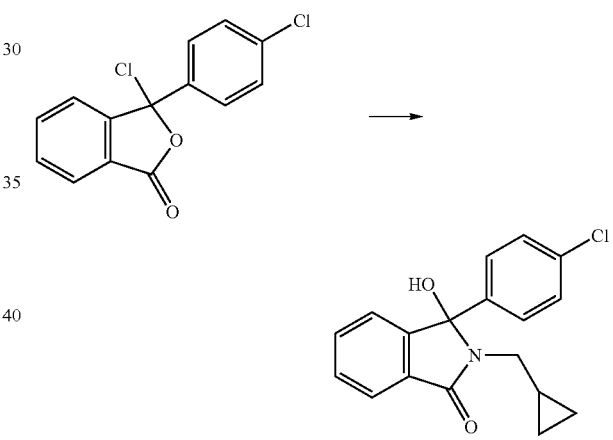

Distilled THF (25 mL) was added to 3-chloro-3-(4-chlorophenyl)-3H-isobenzofuran-1-one (2.3 g, 8.05 mmol) followed by aminomethylcyclopropane hydrochloride (952 mg, 8.86 mmol) and triethylamine (3.36 mL, 24.1 mmol) as for general procedure A. The crude product was recrystallised in the minimum amount of boiling ethyl acetate to give 3-(4-chlorophenyl)-2-cyclopropylmethyl-3-hydroxy-2,3-dihydroisoindolin-1-one as a white solid (1.62 g, 7.47 mmol, 65%); $R_f$=0.5 (40:60: EtOAc:petrol). 194.2-197.1° C. $\lambda_{max}$ ($CH_3OH$)/nm 220, Abs 2.155. IR: 3269, 1684, 1403 $cm^{-1}$. $^1H$ NMR: (300 MHz, $d_6$-DMSO) δ −0.26 (m, 1H, cyclopropane), 0.00 (m, 3H, cyclopropane), 0.56 (m, 1H, N—$CH_2$—CH), 2.71 (dd, 1H, J=14.3, 6.7 Hz, N—$CH_2$), 2.88 (dd, 1H, J=14.3, 7.3 Hz, N—$CH_2$), 6.99 (m, 2H, OH exchangeable with $D_2O$, Ar—H), 7.10 (d, 2H, J=8.7 Hz, Ar—H), 7.17 (d, 2H, J=8.8 Hz, Ar—H), 7.30 (m, 2H, Ar—H), 7.49 (m, 1H, Ar—H). $^{13}C$ NMR: (75 MHz, $d_6$-DMSO) δ 4.1, 5, 43.6, 90.1, 122.8, 123, 128.3, 128.7, 129.7, 130.7, 132.9, 133, 139.7, 149.4, 167.1. LC/MS-ES$^+$ m/z 242.9, 244.9, 296.1, 314.1 [M$^+$]. Anal. Calcd. for $C_{18}H_{16}ClNO_2$: C, 68.90; H, 5.14; N, 4.46%. Found

3-Chloro-3-(4-chlorophenyl)-2-cyclopropylmethyl-2,3-dihydroisoindolin-1-one

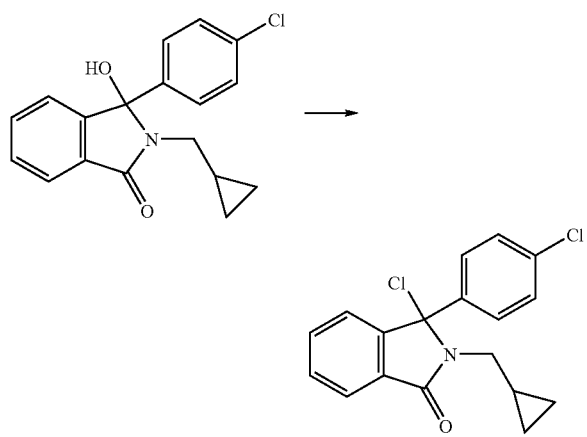

3-(4-Chlorophenyl)-2-cyclopropylmethyl-3-hydroxy-2,3-dihydroisoindolin-1-one (125 mg, 0.39 mmol) was reacted with thionyl chloride (0.03 mL, 0.47 mmol) and a catalytic amount of DMF (3 drops) as for general procedure B. Removal of the solvent gave 3-chloro-3-(4-chlorophenyl)-2-cyclopropylmethyl-2,3-dihydroisoindolin-1-one as a colourless oil (129 mg, 0.39 mmol, 100%).

3-(4-Chlorophenyl)-2-cyclopropylmethyl-3-(3-hydroxycyclopentyloxy)-2,3-dihydro-isoindolin-1-one (NU8280)

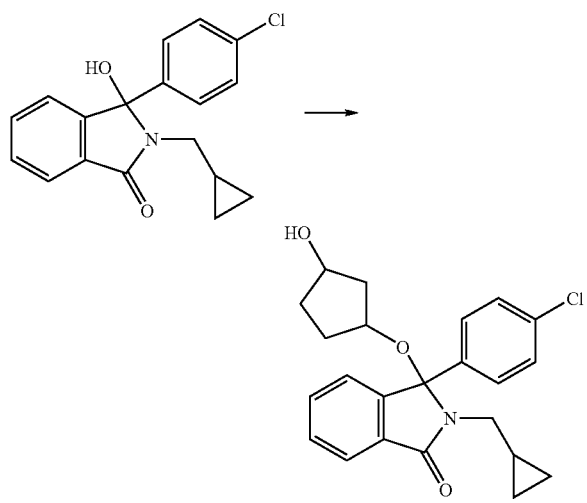

3-Chloro-3-(4-chlorophenyl)-2-cyclopropylmethyl-2,3-dihydroisoindolin-1-one (209 mg, 0.63 mmol) was reacted with 1,3-cyclopentanediol (0.3 mL, 3.15 mmol) as for general procedure C. The crude product was purified by HPLC (H$_2$O: MeOH, 270 nm) to give 3-(4-chlorophenyl)-2-cyclopropylmethyl-3-(3-hydroxycyclopentyloxy)-2,3-dihydro-isoindolin-1-one as a clear glass (127 mg, 0.31 mmol, 51%); R$_f$=0.22 (40:60:EtOAc:petrol). λ$_{max}$ (CH$_3$OH)/nm 225, Abs 3.823. IR: 3396, 2941, 1683, 1375, 1087 cm$^{-1}$. $^1$H NMR: (300 MHz, d$_6$-DMSO) δ −0.35 (m, 1H, cyclopropane), 0.05 (m, 3H, cyclopropane), 0.45 (m, 1H, N—CH$_2$—CH), 1.05-1.75 (m, 6H, cyclopentane), 2.97 (d, 1H, J=9.1 Hz, N—CH$_2$), 3.02 (d, 1H, J=9 Hz, N—CH$_2$), 3.62 (m, 1H, cyclopentane), 3.94 (m, 1H, cyclopentane), 4.17 (d, 1H, J=6 Hz, OH), 7.05 (m, 1H, Ar—H), 7.20 (m, 4H, Ar—H), 7.42 (m, 2H, Ar—H), 7.62 (m, 1H, Ar—H). $^{13}$C NMR: (125 MHz, d$_6$-DMSO) δ 3.9, 4.6, 10.1, 30.8, 31.2, 32.7, 38.9, 39.1, 39.3, 39.5, 39.6, 39.8, 40, 42.5, 43.2, 43.5, 69.6, 70, 73.4, 92.5, 122.7, 124, 128.2, 128.3, 130, 132.5, 132.9, 138.4, 145.9, 167.2, 167.3. LC/MS-ES$^+$ m/z 243, 245, 295.1, 314.1, 316.1, 398.2 [MH$^+$]. Anal. Calcd. for C$_{23}$H$_{24}$ClNO$_3$:C, 69.43; H, 6.08; N, 3.52%. Found C, 69.02; H, 6.15; N, 3.47%. HRMS (EI) m/z Calcd. for C$_{23}$H$_{24}$ClNO$_3$: 397.1444. Found 397.1432.

4-Allyloxybenzyl Alcohol

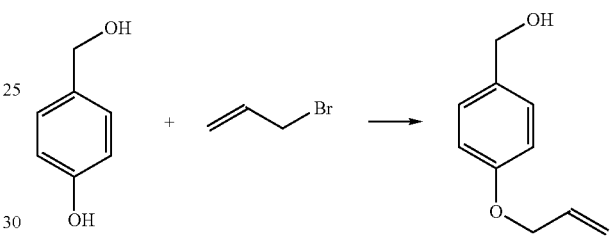

A mixture of 4-hydroxybenzylalcohol (1.52 g, 12.2 mmol.), allyl bromide (1.1 ml, 12.2 mmol.), acetonitrile (40 ml), and potassium carbonate (2.54 g, 18.4 mmol.) was refluxed for 18 hours, then concentrated in vacuo. The residue was dissolved in ethyl acetate and washed with water and brine. The organic layer was dried (MgSO$_4$) and evaporated to give the product as a yellow oil (0.72 g, 71%). $^1$H NMR (300 MHz, CDCl$_3$) δ 2.1 (s, 1H), 4.55 (m, 2H), 4.6 (s, 2H), 5.3 (d, 1H, J=11.5 Hz), 5.43 (d, 1H, J=16.5 Hz), 6.1 (m, 1H), 6.94 (m, 2H), 7.33 (m, 2H); $^{13}$C NMR (75 MHz, CDCl$_3$) δ 65.3, 69.2, 115.2, 118.1, 129.0, 129.4, 133.7, 158.6.

3-Allyloxy-4-methoxybenzyl Alcohol

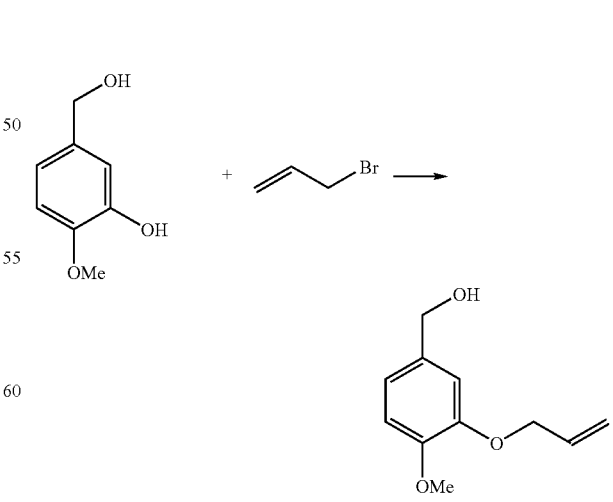

A mixture of 3-hydroxy-4-methoxybenzylalcohol (0.80 g, 7.79 mmol.), allyl bromide (0.45 ml, 5.9 mmol.), acetonitrile (20 ml), and potassium carbonate (1.08 g, 7.8 mmol.) was refluxed for 18 hours, then concentrated in vacuo. The residue was dissolved in ethyl acetate and washed with water and brine. The organic layer was dried (MgSO$_4$) and evaporated to give the product as a yellow oil (1.14 g, 57%). $^1$H NMR (300 MHz, CDCl$_3$) δ 1.90 (s, 1H), 3.79 (s, 3H), 4.52-4.54 (m, 4H), 5.2 (d, 1H, J=12 Hz), 5.32 (d, 1H, J=17.25 Hz), 6.0 (m, 1H), 6.77 (s, 2H), 6.85 (s, 1H); $^{13}$C NMR (75 MHz, CDCl$_3$) δ 56.3, 65.6, 70.3, 111.2, 113.6, 118.4, 119.7, 133.7, 134.4, 147.8, 149.9.

3-(4-Chlorophenyl)-3-(4-allyloxybenzyl)-2-propyl-2,3-dihydroisoindolinone

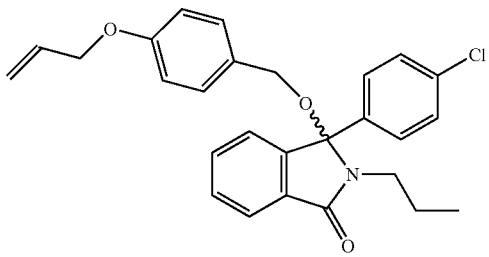

3-(4-Chlorophenyl)-3-hydroxy-2-propyl-2,3-dihydroisoindolinone (0.50 g, 1.66 mmol), THF (10 ml), thionyl chloride (0.15 ml, 2.0 mmol), DMF (3 drops). General procedure B.

The product was dissolved in THF (20 ml), and K$_2$CO$_3$ (0.28 g, 2 mmol), and 4-allyloxybenzyl alcohol (0.33 g, 2.88 mmol) was added according to general procedure C giving the product (0.63 g, 85%). $^1$H NMR (300 MHz, CDCl$_3$) δ 0.74 (t, 3H, J=7.3 Hz, NCH$_2$—CH$_2$—CH$_3$), 1.31 (m, 2H, N—CH$_2$—CH$_2$), 1.47 (m, 2H, N—CH$_2$—CH$_2$), 3.04 (m, 1H, N—CH$_2$), 3.22 (m, 1H, N—CH$_2$), 3.83 (d, 1H, J=10.89, O—CH$_2$), 4.08 (d, 1H, J=10.92, O—CH$_2$), 4.47 (s, 2H, O—CH$_2$—CH—CH$_2$), 5.22 (d, 1H, J=8.09, O—CH$_2$—CH—CH$_2$), 5.35 (d, 1H, J=17.22, O—CH$_2$—CH—CH$_2$), 5.98 (m, 1H, O—CH$_2$—CH—CH$_2$), 6.83 (m, 2H, Ar—H), 7.06-7.44 (m, 9H, Ar—H). 7.85 (s, 1H, Ar—H). $^{13}$C NMR: (75 MHz, CDCl$_3$) δ 12.1, 22.0, 41.9, 65.0, 69.2, 95.1, 115.1, 118.2, 122.9, 123.4, 128.1, 129.1, 129.3, 129.9, 130.2, 132.4, 132.9, 133.6, 134.8, 138.1, 145.6, 158.6, 168.7. LC/MS-ES$^+$ m/z 148.8, 285.1, 287.1, 470.5.

3-(4-Chlorophenyl)-3-(3-allyloxy-4-methoxybenzyl)-2-propyl-2,3-dihydroisoindolinone

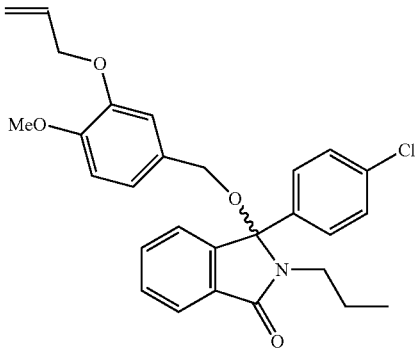

3-(4-Chlorophenyl)-3-hydroxy-2-propyl-2,3-dihydroisoindolinone (0.50 g, 1.66 mmol), THF (10 ml), thionyl chloride (0.15 ml, 2.0 mmol), DMF (3 drops). General procedure B.

The product was dissolved in THF (20 ml), and K$_2$CO$_3$ (0.28 g, 2 mmol), and 3-allyloxy-4-methoxybenzyl alcohol (0.38 g, 2.0 mmol) was added according to general procedure C giving the product (0.42 g, 53%).

$^1$H NMR: (300 MHz, CDCl$_3$) δ 0.76 (m, 3H, NCH$_2$—CH$_2$—CH$_3$), 1.19 (m, 2H, N—CH$_2$—CH$_2$), 1.31 (m, 2H, N—CH$_2$—CH$_2$), 3.01 (m, 1H, N—CH$_2$), 3.21 (m, 1H, N—CH$_2$), 3.80 (s, 3H, OCH$_3$), 3.83 (d, 1H, J=14.26, O—CH$_2$), 4.07 (d, 1H, J=11.08, O—CH$_2$), 4.54 (s, 2H, O—CH$_2$—CH—CH$_2$), 5.22 (d, 1H, J=10.44, O—CH$_2$—CH—CH$_2$), 5.34 (d, 1H, J=17.29, O—CH$_2$—CH—CH$_2$), 6.01 (m, 1H, O—CH$_2$—CH—CH$_2$), 6.72-7.82 (m, 10H, Ar—H), 7.85 (d, 1H, Ar—H). $^{13}$C NMR: (75 MHz, CDCl$_3$) δ 12.2, 22.0, 41.9, 56.4, 65.1, 70.2, 95.1, 111.9, 113.8, 118.4, 120.7, 123.5, 123.9, 128.3, 129.0, 130.1, 131.2, 132.4, 132.9, 133.7, 134.8, 138.1, 145.6, 148.4, 149.5, 168.6. LC/MS-ES$^+$ m/z 118.8, 178.5, 285.1, 287.1, 500.4.

3-(4-Chlorophenyl)-3-(4-hydroxybenzyl)-2-propyl-2,3-dihydroisoindolinone (NU8243)

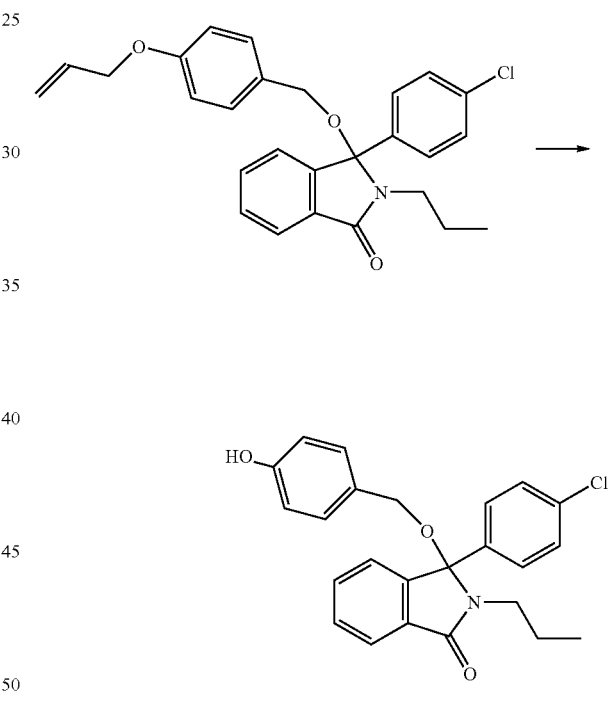

A mixture of 3-(4-chlorophenyl)-3-(4-allyloxybenzyl)-2-propyl-2,3-dihydroisoindolinone (0.190 g, 0.43 mmol), Pd(PPh$_3$)$_4$ (10 mg, 0.009 mmol), K$_2$CO$_3$ (0.19 g, 1.35 mmol) in degassed, anhydrous methanol (10 ml), was stirred 16 h, then concentrated in vacuo. Chromatography (silica; 35% EtOAc, petrol) gave the product (160 mg, 93%). $^1$H NMR: (300 MHz, CDCl$_3$) δ 0.72 (m, 3H, J=7.3, NCH$_2$—CH$_2$—CH$_3$), 1.28 (m, 2H, N—CH$_2$—CH$_2$), 1.46 (m, 2H, N—CH$_2$—CH$_2$), 2.1 (s, 1H, OH), 3.05 (m, 1H, N—CH$_2$), 3.22 (m, 1H, N—CH$_2$), 3.82 (d, 1H, J=10.8, O—CH$_2$), 4.04 (d, 1H, J=10.8, O—CH$_2$), 6.8 (d, 2H, Ar—H), 7.04-7.45 (m, 9H, Ar—H), 7.84 (m, 1H, Ar—H). $^{13}$C NMR: (75 MHz, CDCl$_3$) δ 12.2, 22.0, 41.9, 65.2, 95.3, 115.9, 123.5, 123.7, 128.1, 128.3, 129.0, 129.6, 130.4, 130.9, 133.1, 134.9, 137.9, 145.7, 156.8, 169.1. LC/MS-ES+ m/z 244.2, 246.2, 285.1, 430.6.

3-(4-Chlorophenyl)-3-(3-hydroxy-4-methoxybenzyl)-2-propyl-2,3-dihydroisoindolinone (NU8244)

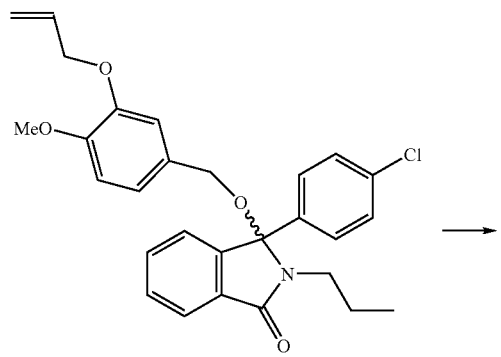

A mixture of 3-(4-chlorophenyl)-3-(3-allyl-4-methoxybenzyl)-2-propyl-2,3-dihydroisoindolinone (0.210 g, 0.44 mmol), Pd(PPh$_3$)$_4$ (10 mg, 0.009 mmol), K$_2$CO$_3$ (0.19 g, 1.35 mmol) in degassed, anhydrous methanol (10 ml), was stirred 2 h, then concentrated in vacuo. Chromatography (silica; 30% EtOAc, petrol) gave the product (130 mg, 68%). $^1$H NMR: (300 MHz, CDCl$_3$) δ 0.74 (m, 3H, J=7.4, NCH$_2$—CH$_2$—CH$_3$), 1.18 (m, 2H, N—CH$_2$—CH$_2$), 1.3 (m, 2H, N—CH$_2$—CH$_2$), 3.02 (m, 1H, N—CH$_2$), 3.22 (m, 1H, N—CH$_2$), 3.81 (s, 3H, OCH$_3$), 3.80 (d, 1H, J=9.1, O—CH$_2$), 4.04 (d, 1H, J=10.7, O—CH$_2$), 5.77 (s, 1H, OH), 6.62-6.9 (m, 3H, Ar—H), 7.06-7.46 (m, 7H, Ar—H), 7.81 (m, 1H, Ar—H). $^{13}$C NMR: (75 MHz, CDCl$_3$) δ 12.2, 22.0, 41.9, 56.4, 65.0, 95.1, 110.8, 114.4, 119.6, 123.4, 123.9, 128.3, 129.0, 130.3, 131.0, 132.3, 133.0, 134.8, 138.0, 145.6, 146.0, 146.7, 168.7. LC/MS-ES+ m/z 138.8, 162.7, 244.3, 285.1, 287.1, 438.7.

2-Benzyl-3-chloro-3-phenyl-2,3-dihydroisoindolin-1-one (11a)

A solution of 10a (0.25 g, 0.79 mmol) in THF (20 mL) was reacted with thionyl chloride (0.07 mL, 0.87 mmol) and DMF (3 drops), the mixture was stirred for 16 h, and concentrated in vacuo giving 10a as an orange solid (0.27 g, 0.79 mmol) which was used without further purification.

N-[2-(2-Benzyl-3-oxo-1-phenyl-2,3-dihydro-1H-isoindolin-1-yloxy)ethyl]-2,4-dihydroxybenzamide (59) (NU8203)

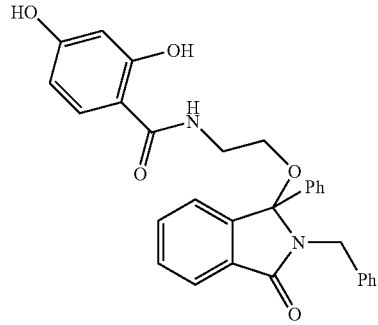

General procedure H: 11a (316 mg, 0.95 mmol), 2,4-dihydroxy-N-(2-hydroxyethyl)benzamide (342 mg, 1.73 mmol). Chromatography (50% EtOAc, petrol), HPLC and recrystallization (EtOAc) gave 59 as an orange oil (240 mg, 0.48 mmol, 61%). λ$_{max}$ (CH$_3$OH)/nm 208.5, Abs 0.937. IR: 3333, 1678, 1637 cm$^{-1}$. $^1$H NMR (300 MHz, CDCl$_3$) δ 2.66 (m, 1H, O—CH$_2$), 2.28 (m, 1H, O—CH$_2$), 2.95 (m, 1H, O—CH$_2$—CH$_2$), 3.05 (m, 1H, O—CH$_2$—CH$_2$), 3.82 (d, 1H, J=14.7 Hz, N—CH$_2$), 4.83 (d, 1H, J=14.7 Hz, N—CH$_2$), 6.05 (m, 1H, NH), 6.36 (m, 1H, Ar—H), 6.38 (m, 1H, Ar—OH), 7.00 (m, 1H, Ar—H), 7.20 (m, 12H, Ar—H), 7.38 (m, 2H, Ar—H), 7.84 (m, 1H, Ar—H), 12.37 (bs, 1H, Ar—OH). $^{13}$C NMR (75 MHz, CDCl$_3$) δ 38.9, 43.6, 61.8, 96.2, 104.5, 107.5, 107.7, 123.3, 124.1, 126.6, 128.7, 129, 129.1, 129.5, 130.3, 131.6, 133.4, 137.8, 138.3, 145.6, 161.9, 163.9, 169, 170.1. LCMS (ESI+) m/z 494 [M+H]+. Anal. Calcd. for C$_{30}$H$_{26}$N$_2$O$_5$:C, 72.86; H, 5.30; N, 5.66%. Found C, 72.46; H, 5.55; N, 5.73%.

2-Benzyl-3-phenyl-3-(2-phenylaminoethoxy)-2,3-dihydroisoindolin-1-one (60) (NU8204)

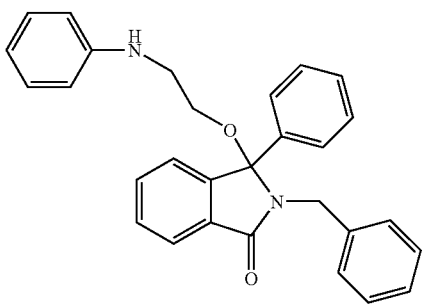

General procedure H: 11a (635 mg, 1.9 mmol), and 2-anilino ethanol (573 mg, 4.18 mmol). Chromatography (silica; 40% EtOAc, petroleum ether) gave 60 as a light yellow solid (550 mg, 66%), mp 50° C. IR ν (cm$^{-1}$): 3375, 3028, 2924, 2876, 1691, 1601, 1494, 1466, 1382, 1351, 1323, 1062. $^1$H-NMR: δ$_H$ (300 MHz, CDCl$_3$): 7.82 (1H, d, J=6.5, Ar), 7.36 (2H, dq, J=7.4 & 1.2 Hz, Ar), 7.22 (7H, s, Ar), 7.13 (3H, m, Ar), 7.04 (2H, t, J=7.4 Hz, Ar), 6.98 (1H, d, J=6.5 Hz, Ar), 6.60 (1H, t, J=7.3 Hz, Ar), 6.39 (2H, d, J=7.8 Hz, Ar), 4.78

(1H, d, J=4.7 Hz, —CH$_2$-Ph), 3.81 (1H, d, J=4.7 Hz, —CH$_2$-Ph), 3.50 (1H, br, —NH), 2.75 (4H, m, —O—CH$_2$—CH$_2$—NH). $^{13}$C-NMR: δ$_C$ (75 MHz, CDCl$_3$): 168.62, 148.29, 145.86, 138.79, 138.19, 133.08, 131.99, 130.10, 129.73, 129.59, 128.93, 128.66, 127.76, 126.82, 124.03, 123.39, 117.95, 113.35, 96.01, 61.81, 43.56, 43.39. LCMS (ESI+) 299 [M+Na]$^+$. Anal. Calcd. for C$_{29}$H$_6$N$_2$O$_{22}$ C, 80.16; H, 6.03; N, 6.45. Found: C, 79.32; H, 6.02; N, 6.12.

2-[2-(t-Butyldiphenylsilanyloxy)ethyl]-3-phenyl-3-propoxy-2,3-dihydroisoindolin-1-one (76)

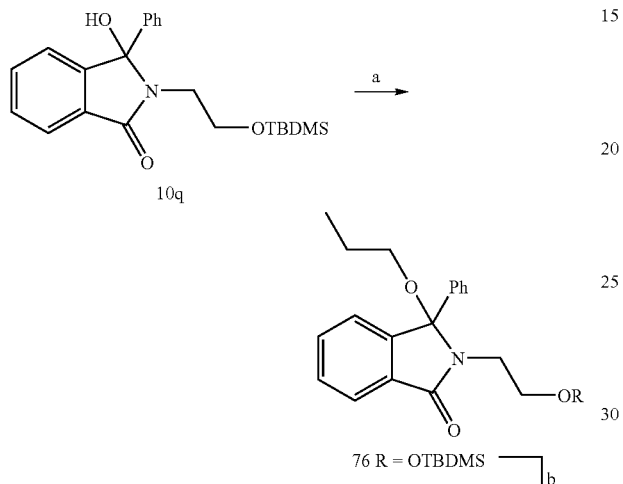

General procedure I: 10q (400 mg, 0.79 mmol), thionyl chloride (0.187 g, 1.57 mmol), THF (10 mL), n-propanol (70 µL, 1.18 mmol), triethylamine (158 mg, 1.6 mmol). Chromatography (silica; 40% EtOAc, petroleum ether) gave 76 as a white solid (240 mg, 55%) $^1$H-NMR (300 MHz, CDCl$_3$) δ$_H$ 7.78 (1H, m, Ar); 7.52 (4H, m, Ar); 7.29 (13H, m, Ar); 7.04 (1H, m, Ar); 3.55 (2H, m, OCH$_2$); 3.42 (1H, m, OCH$_2$); 3.24 (1H, m, OCH$_2$); 2.98 (1H, q, J=7.05 Hz, NCH$_2$); 2.69 (1H, q, J=7.05 Hz, NCH$_2$); 1.39 (2H, m, CH$_2$); 0.92 (9H, s, $^t$Bu); 0.77 (3H, t, J=7.4 Hz, CH$_3$). $^{13}$C-NMR (75 MHz, CDCl$_3$) δ$_C$ 11.13, 19.51, 23.03, 27.13, 41.38, 61.04, 64.41, 95.01, 123.43, 123.64, 126.60, 127.98, 128.72, 129.84, 129.92, 132.20, 132.71, 133.98, 135.84, 135.88, 139.41, 146.28, 168.69.

2-(2-Hydroxyethyl)-3-phenyl-3-propoxy-2,3-dihydroisoindolin-1-one (77) (NU8206)

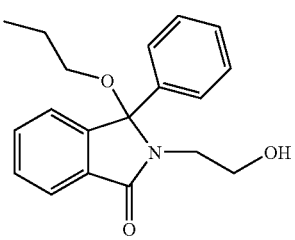

TBAF (1M solution in THF; 190 mg, 0.73 mmol) was added dropwise to a solution of 76 (200 mg, 0.36 mmol) in THF (10 mL). After 30 min. the solvent was evaporated to dryness and the residue was partitioned between EtOAc (100 ml) and water (50 ml). The organic layer was washed with water (2×20 ml), brine (20 ml), dried and concentrated. Chromatography (silica; 60% EtOAc, petroleum ether) gave 67 as a white solid. (110 mg, 98%) mpt 85° C. IR ν (cm$^{-1}$): 3456, 2961, 2931, 2877, 1683, 1463, 1443, 1388, 1311, 1251, 1072, 1047, 752, 695. $^1$H-NMR (300 MHz, CDCl$_3$) δ$_H$ 7.81 (1H, m, Ar), 7.43 (2H, m, Ar), 7.32 (2H, m, Ar), 7.25 (3H, m, Ar), 7.09 (1H, m, Ar), 3.95 (1H, br, s, —OH), 3.56 (2H, m, —O—CH$_2$—CH$_2$—CH$_3$), 3.42 (1H, ddd, J=14.8, 6.63 & 3.1 Hz, —O—CH$_2$—CH$_2$—N), 3.25 (1H, ddd, J=14.8, 6.63 & 3.1 Hz, —O—CH$_2$—CH$_2$—N), 3.09 (1H, dt, J=8.84, 6.35 & 2.5 Hz, —O—CH$_2$—CH$_2$—N), 2.83 (1H, dt, J=8.84, 6.35 & 2.5 Hz, —O—CH$_2$—CH$_2$—N), 1.56 (2H, q, J=7.00 Hz, —O—CH$_2$—CH$_2$—CH$_3$), 0.88 (3H, t, J=7.4 Hz, —O—CH$_2$—CH$_2$—CH$_3$). $^{13}$C-NMR (75 MHz, CDCl$_3$) δ$_C$ 170.48, 146.25, 138.79, 133.16, 131.65, 130.12, 129.01, 126.53, 123.91, 123.55, 95.61, 64.89, 62.41, 43.83, 23.13, 11.22. LCMS (ESI+) m/z 334 [M+Na]. Anal. Calcd. for C$_{19}$H$_{21}$NO$_3$: C, 73.29; H, 6.80; N, 4.50. Found: C, 73.05; H, 6.78; N, 4.36.

5-(2-Benzyl-3-oxo-1-phenyl-2,3-dihydro-1H-isoindolin-1-yloxymethyl)-furan-2-carbaldehyde (58) (NU8207)

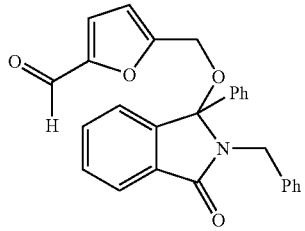

General procedure H: 11a (316 mg, 0.95 mmol), 5-hydroxymethylfuran-2-carbaldehyde (264 mg, 2.1 mmol). Chromatography (40:60 EtOAc:petrol) gave 58 as a grey oil (99 mg, 0.23 mmol, 23%); R$_f$ 0.27 (40:60 EtOAc:petrol). λ$_{max}$ (CH$_3$OH)/nm 208.5, Abs 0.301. IR: 2995, 1690, 1676 cm$^{-1}$. $^1$H NMR: (500 MHz, CDCl$_3$) δ 3.58 (d, 1H, J=12.5 Hz, O—CH$_2$), 3.69 (d, 1H, J=12.8 Hz, O—CH$_2$), 3.82 (d, 1H, J=14.6 Hz, N—CH$_2$), 4.86 (d, 1H, J=14.7 Hz, N—CH$_2$), 5.82 (d, 1H, J=3.6 Hz, Hb), 6.97 (d, 1H, J=3.4 Hz, Ha), 7.09 (m, 1H, Ar—H), 7.19 (m, 10H, Ar—H), 7.40 (m, 1H, Ar—H), 7.44 (m, 1H, Ar—H), 7.86 (d, 1H, J=7.3, Ar—H), 9.47 (s, 1H, CHO) $^{13}$C NMR (75 MHz, CDCl$_3$) δ 43.6, 61.3, 96.2, 110.3, 112.5, 114.5, 123.5, 123.6, 125.6, 125.8, 128.6, 128.9, 131.2, 152.9, 168.2, 178.1. LCMS (ESI+) m/z 424 [M+H]$^+$, 446 [M+Na]$^+$. Anal. Calcd. for C$_{27}$H$_{21}$NO$_4$:C, 76.58; H, 5.00; N, 3.31%. Found C, 76.37; H, 5.13; N, 3.00%.

3-(3-Allyloxybenzyloxy)-2-benzyl-3-phenyl-2,3-dihydroisoindolin-1-one (53)

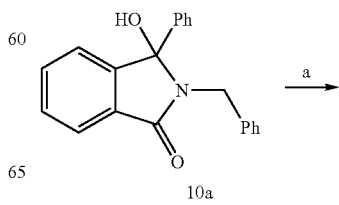

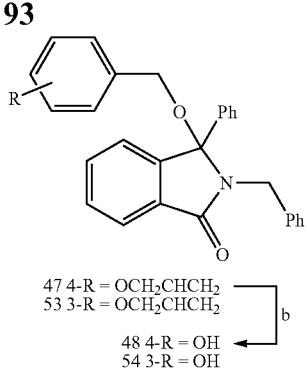

47 4-R = OCH₂CHCH₂
53 3-R = OCH₂CHCH₂

48 4-R = OH
54 3-R = OH b

General procedure H: 11a (632 mg, 1.9 mmol), (3-allyloxyphenyl)methanol (373 mg, 2.28 mmol) and potassium carbonate (393 mg, 2.85 mmol). Chromatography (30% EtOAc, petrol) to gave 53 as a colourless oil (656 mg, 1.4 mmol, 74%); $R_f$ 0.50 (40:60 EtOAc:petrol). $\lambda_{max}$ (CH$_3$OH)/nm 216, Abs 1.066. IR: 3032, 2908, 1700 cm$^{-1}$. $^1$H NMR: (500 MHz, CDCl$_3$) δ 3.60 (d, 1H, J=11.3 Hz, O—CH$_2$), 3.67 (d, 1H, J=11 Hz, O—CH$_2$), 3.97 (1H, J=14.6 Hz, N—CH$_2$), 4.42 (dt, 2H, J=5.4$_{vic}$, 1.3$_{allylic}$ Hz, O—CH$_2$—CH=CH$_2$), 4.73 (1H, J=14.7 Hz, N—CH$_2$), 5.23 (dq, 1H, J=10.4$_{cis}$, 1.5$_{allylic}$ Hz, CH=CH$_2$), 5.34 (dq, 1H, J=17.1$_{trans}$, 1.5$_{allylic}$ Hz, CH=CH$_2$), 5.99 (m, 1H, CH=CH$_2$), 6.48 (m, 2H, Ar—H), 6.70 (dd, 1H, J=8.2, 1.9 Hz, Ar—H), 7.07 (m, 5H, Ar—H), 7.21 (m, 5H, Ar—H), 7.31 (m, 2H, Ar—H), 7.41 (m, 2H, Ar—H), 7.87 (m, 1H, Ar—H). $^{13}$C NMR: (75 MHz, CDCl$_3$) δ 43.7, 65, 69.1, 96.1, 113.9, 114.3, 118, 120.2, 123.5, 123.9, 126.9, 127.5, 128.5, 128.8, 129.8, 130, 132.1, 133, 133.7, 137.8, 138.8, 139.3, 146, 158.8, 168.7. LCMS (ESI+) m/z 462 [M+H]$^+$, 484.1 [M+Na]$^+$. Anal. Calcd. for C$_{31}$H$_{27}$NO$_3$: C, 80.67; H, 5.90; N, 3.03%. Found C, 80.23; H, 5.53; N, 2.62%.

1H, Ar—H). $^{13}$C NMR (75 MHz, CDCl$_3$). δ 43.8, 64.9, 96.1, 114.6, 114.7, 120, 123.5, 124, 126.9, 127.5, 128.6, 128.8, 129.6, 129.8, 130.1, 132, 133, 137.9, 138.8, 139.5, 146, 155.7, 168.8.). LCMS (ESI+) m/z 422 [M+H]$^+$, 444 [M+Na]$^+$. Anal. Calcd. for C$_{28}$H$_{23}$NO$_3$.0.33H$_2$O: C, 78.67; H, 5.58; N, 3.28%. Found C, 78.62; H, 5.29; N, 3.08%.

3-(4-Allyloxybenzyloxy)-2-benzyl-3-phenyl-2,3-dihydroisoindolin-1-one (47)

General procedure H: 11a (316 mg, 0.95 mmol), 4-allyloxyphenylmethanol (186 mg, 1.14 mmol) and potassium carbonate (196 mg, 1.42 mmol). Chromatography (30% EtOAc, petrol) gave 47 as a colourless oil (266 mg, 0.5 mmol, 61%). $\lambda_{max}$ (CH$_3$OH)/nm 220, Abs 0.958. IR 3036, 2935, 1703 cm$^{-1}$. $^1$H NMR (500 MHz, CDCl$_3$) δ 3.55 (d, 1H, J=10.7 Hz, O—CH$_2$), 3.63 (d, 1H, J=10.7 Hz, O—CH$_2$), 3.94 (1H, J=14.4 Hz, N—CH$_2$), 4.42 (d, 2H, J=5.4$_{vic}$, Hz, O—CH$_2$—CH=CH$_2$), 4.73 (1H, J=14.7 Hz, N—CH$_2$), 5.19 (dd, 1H, J=10.4$_{cis}$, 1.3$_{gem}$ Hz, CH=CH$_2$), 5.31 (dd, 1H, J=17.4$_{trans}$, 1.6$_{gem}$ Hz, CH=CH$_2$), 5.95 (m, 1H, CH=CH$_2$), 6.69 (d, 2H, J=8.9 Hz, Ar—H), 6.74 (d, 2H, J=8.6 Hz, Ar—H), 7.08 (m, 4H, Ar—H), 7.16 (m, 5H, Ar—H), 7.31 (m, 2H, Ar—H), 7.39 (m, 2H, Ar—H), 7.87 (m, 1H, Ar—H). $^{13}$C NMR (75 MHz, CDCl$_3$) δ 43.3, 64.5, 68.7, 95.6, 114.2, 117.6, 123, 123.5, 126.5, 127.1, 128.1, 128.3, 128.4, 129, 129.4, 129.5, 129.6, 131.7, 132.5, 133.2, 137.5, 138.5, 145.8, 158, 168.3. LCMS (ESI+) m/z 298.1, 462.2 [M+H]$^+$, 484.2 [M+Na]$^+$.

2-Benzyl-3-(4-hydroxybenzyloxy)-3-phenyl-2,3-dihydroisoindolin-1-one (48) (NU8215)

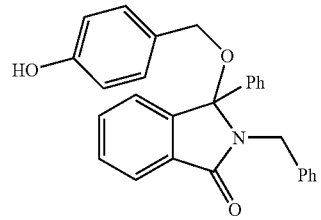

To a degassed solution of 47 (145 mg, 0.31 mmol) in MeOH (12 mL) was added palladium tetrakistriphenylphosphine (3.5 mg, 1 mol %) and potassium carbonate (128 mg, 0.93 mmol). The mixture was stirred at rt for 2 h then concentrated in vacuo. Chromatography (30% EtOAc, petrol) gave 48 as a white solid, (104 mg, 0.24 mmol, 80%) mp 119.6-121.3° C. $\lambda_{max}$ (CH$_3$OH)/nm 211, Abs 0.822. IR: 3214, 3031, 1674 cm$^{-1}$. $^1$H NMR (300 MHz, CDCl$_3$) δ 3.54 (d, 1H, J=10.5 Hz, O—CH$_2$), 3.62 (d, 1H, J=10.6, O—CH$_2$), 3.92 (d, 1H, J=14.6 Hz, N—CH$_2$), 4.72 (d, 1H, J=14.7 Hz, N—CH$_2$), 6.69 (s, 1H, Ar—OH), 7.08 (m, 4H, Ar—H), 7.22 (m, 11H, Ar—H), 7.41 (m, 2H, Ar—H), 7.78 (m, 1H, Ar—H). $^{13}$C NMR (75 MHz, CDCl$_3$) δ 43.8, 66.1, 96.1, 115.4, 123.5, 124, 124.2, 126.9, 127.6, 128.4, 128.6, 128.8, 129.4, 129.7, 129.8, 130, 131.9, 133.1, 137.8, 138.8, 146.2, 169). LCMS (ESI+) m/z 422.1 [M+H]$^+$, 444.1 [M+Na]$^+$. Anal. Calcd. for C$_{28}$H$_{23}$NO$_3$: C, 79.79; H, 5.50; N, 3.32%. Found C, 79.65; H, 5.59; N, 3.39%.

2-Benzyl-3-(3-hydroxybenzyloxy)-3-phenyl-2,3-dihydroisoindolin-1-one (54) (NU8208)

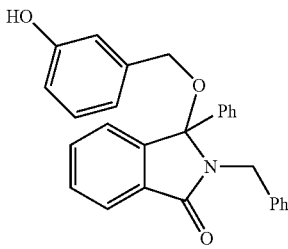

To a degassed solution of 53 (196 mg, 0.42 mmol) in MeOH (12 mL) was added palladiumtetrakis triphenylphosphine (4.8 mg, 1 mol %) and potassium carbonate (173 mg, 1.26 mmol). The mixture was stirred at rt for 2 h then concentrated in vacuo. Chromatography (30% EtOAc, petrol) gave 54 as a white solid, (125 mg, 0.29 mmol, 71%); mp 122-123° C. $\lambda_{max}$ (CH$_3$OH)/nm 206, Abs 0.222. IR: 3228, 3031, 1674 cm$^{-1}$. $^1$H NMR (300 MHz, CDCl$_3$) δ 3.58 (d, 1H, J=11.2 Hz, O—CH$_2$), 3.67 (d, 1H, J=11.2, O—CH$_2$), 3.94 (d, 1H, J=14.6 Hz, N—CH$_2$), 4.75 (1H, J=14.6 Hz, N—CH$_2$), 4.89 (s, 1H, Ar—OH), 6.30 (m, 1H, Ar—H), 6.45 (d, 1H, J=7.6 Hz, Ar—H), 6.63 (dd, 1H, J=8.1, 2.5 Hz, Ar—H), 7.00-7.31 (m, 12H, Ar—H), 7.42 (m, 2H, Ar—H), 7.88 (m,

3-(3,5-Dimethoxy-4-hydroxybenzyloxy)-2-propyl-3-[4-(2-trimethylsilylethoxymethoxy)phenyl]-2,3-dihydroisoindolin-1-one (110) (NU8209)

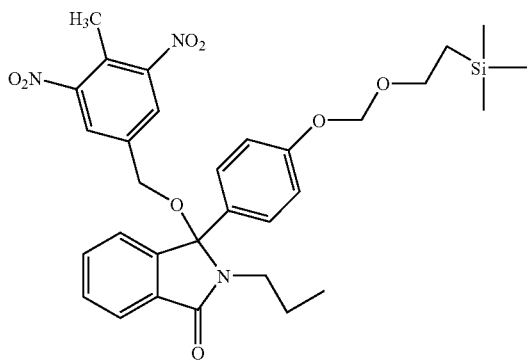

General procedure I: 10j (0.31 mmol), syringic alcohol (127 mg, 0.69 mmol). Chromatography (35:65 EtOAc:petrol) and (C18 silica; 20% MeOH, H$_{2O}$ to 100% MeOH gradient) gave 110 as a colourless oil (38 mg, 0.065 mmol, 2%). $\lambda_{max}$ (CH$_3$OH)/nm 210, Abs 0.336. IR: 3371, 2947, 1689, 1604, 1460, 1427, 1372 cm$^{-1}$. $^1$H NMR (300 MHz, CDCl$_3$) δ −0.02 (s, 9H, Si—(CH$_3$)$_3$), 0.83 (t, 3H, J=7.4 Hz, CH$_2$—CH$_2$—CH$_3$), 0.95 (m, 2H, R—O—CH$_2$—CH$_2$—Si), 1.43 (m, 1H, N—CH$_2$—CH$_2$), 1.55 (m, 1H, N—CH$_2$—CH$_2$), 3.12 (m, 1H, N—CH$_2$), 3.34 (m, 1H, N—CH$_2$), 3.75 (m, 2H, O—CH$_2$—CH$_2$—Si), 3.89 (s, 6H, OMe), 3.94 (d, 1H, J=11.2 Hz, O—CH$_2$), 4.17 (d, 1H, J=11.3 Hz, O—CH$_2$), 5.22 (s, 2H, O—CH$_2$—O), 5.55 (s, 1H, OH), 6.49 (s, 2H, Ar—H), 7.00 (d, 2H, J=9.1 Hz, Ar—H), 7.17 (m, 1H, Ar—H), 7.34 (d, 2H, J=8.8 Hz, Ar—H), 7.49 (m, 2H, Ar—H), 7.90 (m, 1H, Ar—H). $^{13}$C NMR (75 MHz, CDCl$_3$) δ −3.3, 9.8, 16, 19.6, 39.5, 54.3, 63.1, 64.3, 90.8, 93.1, 102.2, 114, 121.2, 121.3, 125.6, 126.7, 127.6, 129.8, 130, 130.3, 132.2, 143.7, 144.9, 155.5, 160.3, 166.3. LCMS (ESI+) m/z 355, 396.1, 397.1, 414.1, 602 [M+Na]$^+$. Anal. Calcd. for C$_{32}$H$_{41}$NO$_7$Si: C, 66.29; H, 7.13; N, 2.42%. Found C, 67.26; H, 7.22; N, 1.65%; HRMS (EI) m/z Calcd. for C$_{32}$H$_{41}$NO$_7$Si: 579.2652. Found 579.2673.

2-Benzyl-3-(2-bromoethoxy)-3-phenyl-2,3-dihydroisoindolin-1-one (51)

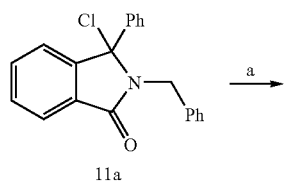

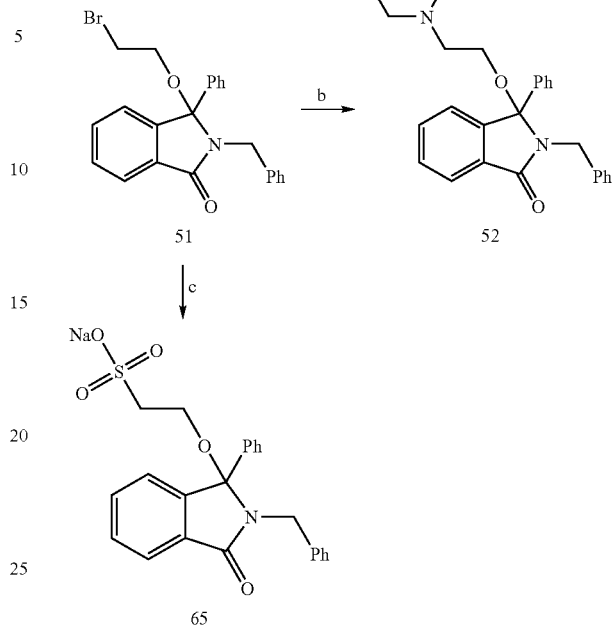

General procedure H: 11a (316 mg, 0.95 mmol), 2-bromoethanol (0.15 mL, 2.1 mmol). Chromatography (40% EtOAc, petrol) gave 51 as a colourless oil (320 mg, 0.75 mmol, 80%). $\lambda_{max}$ (CH$_3$OH)/nm 218, Abs 0.624. IR 3027, 1689, 1450 cm$^{-1}$. $^1$H NMR (300 MHz, CDCl$_3$) δ 2.91 (m, 4H, O—CH$_2$—CH$_2$—Br), 3.88 (d, 1H, J=14.6 Hz, N—CH$_2$), 4.98 (d, 1H, J=14.6 Hz, N—CH$_2$), 7.18 (m, 1H, Ar—H), 7.33 (m, 10H, Ar—H), 7.50 (m, 2H, Ar—H), 7.93 (m, 1H, Ar—H). $^{13}$C NMR (75 MHz, CDCl$_3$) δ 30.1, 43.5, 63.1, 95.9, 123.6, 124.1, 126.8, 127.7, 128.6, 129, 130.2, 131.7, 133.1, 138.1, 138.5, 145.5, 168.5. LCMS (ESI+) m/z 424 [M+H]$^+$.

Sodium 2-(2-Benzyl-3-oxo-1-phenylisoindolin-1-yloxy)ethanesulfonate (65) (NU8210)

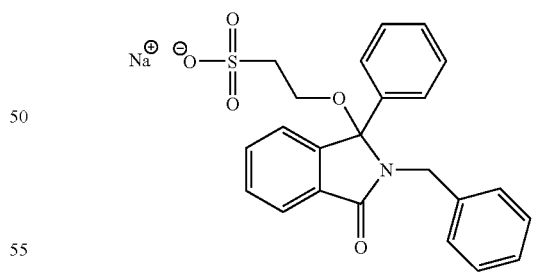

A mixture of 51, sodium sulfite (200 mg, 1.65 mmol) in DME (10 mL) and water (10 mL) was heated to reflux for 24 h, then evaporated to dryness. The residue was extracted with hot methanol (4×15 mL) and the combined extracts concentrated in vacuo giving a white solid which was washed with ether (20 mL) and petroleum ether (20 mL), then dissolved in DCM (50 mL) filtered and evaporated to give 65 as a white solid (95 mg, 26%), mpt 56° C. IR ν (cm$^{-1}$): 3437, 2929, 1689, 1454, 1373, 1175, 1036, 748, 686. $^1$H-NMR (300 MHz, CDCl$_3$) δ$_H$ 7.78 (1H, m, Ar), 7.46 (2H, m, Ar), 7.25-7.00

(11H, m, Ar), 4.69 (1H, d, J=14.88 Hz, N—CH$_2$-Ph), 3.95 (1H, d, J=14.88 Hz, N—CH$_2$-Ph), 3.12 (1H, m, O—CH$_2$—CH$_2$—SO$_3$Na), 2.99 (1H, m, O—CH$_2$—CH$_2$—SO$_3$Na), 2.62 (1H, m, O—CH$_2$—CH$_2$—SO$_3$Na), 2.31 (1H, m, O—CH$_2$—CH$_2$—SO$_3$Na). $^{13}$C-NMR (75 MHz, CDCl$_3$) $\delta_C$ 44.50, 51.97, 60.50, 97.54, 124.75, 125.22, 127.89, 128.06, 128.78, 129.77, 129.93, 130.02, 130.28, 130.43, 130.58, 131.53, 132.88, 134.69, 139.20, 139.96, 147.30, 170.69. LCMS (ESI+) 446 [M+1]$^+$. Anal. Calcd. for C$_{23}$H$_{20}$NNaO$_5$S: C, 62.01; H, 4.53; N, 3.14. Found: C, 64.48; H, 6.16; N, 2.26.

2-Benzyl-3-phenyl-3-(2-piperazin-1-ylethoxy)-2,3-dihydroisoindolin-1-one (52) (NU8211)

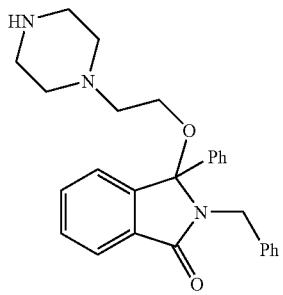

A mixture of 51 (289 mg, 0.6 mmol) and piperazine, (516 mg, 6 mmol) in MeOH (10 mL) was refluxed for 16 h, then concentrated in vacuo. The residues were dissolved in EtOAc (40 mL), washed with water (10×20 mL), brine (2×10 mL), dried (MgSO$_4$) and concentrated in vacuo. The residues were triturated in ether giving 52 as a white solid (80 mg, 0.18 mmol, 31%). mp 137.9-139.5° C. $\lambda_{max}$ (CH$_3$OH)/nm 206.5, Abs 0.651. IR: 3341, 2927, 1681 cm$^{-1}$. $^1$H NMR (500 MHz, CDCl$_3$) δ 1.89 (m, 1H, O—CH$_2$), 2.13 (m, 4H, HN—(CH$_2$)$_2$), 2.15 (bs, 1H, NH), 2.72 (m, 6H, CH$_2$—N—(CH$_2$)$_2$), 2.79 (m, 1H, O—CH$_2$), 3.82 (d, 1H, J=14.9 Hz, N—CH$_2$), 4.78 (d, 1H, J=14.7 Hz, N—CH$_2$), 7.06 (m, 1H, Ar—H), 7.17 (m, 10H, Ar—H), 7.40 (m, 2H, Ar—H), 7.83 (m, 1H, Ar—H). $^{13}$C NMR (125 MHz, CDCl$_3$) δ43.1, 45.8, 54.4, 57.2, 60.3, 95.6, 123, 123.6, 126.4, 127.2, 128.2, 128.41, 128.45, 129.3, 129.5, 131.6, 132.5, 137.8, 145.6, 168.3. LCMS (ESI+) m/z 298, 428.2 [M+H]$^+$. Anal. Calcd. for C$_{27}$H$_{29}$N$_3$O$_2$: C, 75.85; H, 6.84; N, 9.83%. Found C, 75.61; H, 6.75; N, 9.63%.

2-Benzyl-3-(2-butyl-3H-imidazol-4-ylmethoxy)-3-phenyl-2,3-dihydroisoindolin-1-one (46) (NU8212)

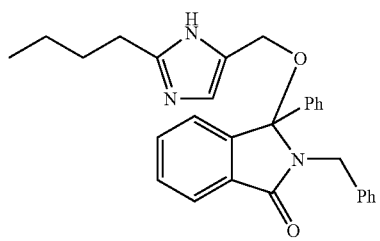

General procedure H: 11a (170 mg, 0.54 mmol), 2-butyl-3H-imidazol-4-yl)methanol (100 mg, 0.65 mmol). Chromatography (80% EtOAc, petrol) gave 46 as a white solid (104 mg, 0.2 mmol, 42%). mp 110-112.2° C. $\lambda_{max}$ (CH$_3$OH)/nm 213, Abs 0.995. IR 2929, 1689, 1349 cm$^{-1}$. $^1$H NMR (300 MHz, CDCl$_3$) δ 0.85 (t, 3H, J=7.3 Hz, CH$_3$), 1.28 (sext, 2H, J=7.6 Hz, CH$_3$—CH$_2$—CH$_2$), 1.55 (quint, 2H, J=7.7 Hz, CH$_3$—CH$_2$—CH$_2$—CH$_2$), 2.49 (t, 2H, J=7.6 Hz, CH$_3$—CH$_2$—CH$_2$—CH$_2$), 3.62 (d, 1H, J=11.1 Hz, O—CH$_2$), 3.68 (d, 1H, J=11.1 Hz, O—CH$_2$), 3.77 (d, 1H, J=14.9 Hz, N—CH$_2$), 4.92 (d, 1H, J=14.8 Hz, N—CH$_2$), 6.35 (bs, 1H, NH), 7.11 (m, 1H, Ar—H), 7.23 (m, 11H, Ar—H, +Ha), 7.77 (m, 2H, Ar—H), 7.88 (m, 1H, Ar—H). $^{13}$C NMR (75 MHz, CDCl$_3$) δ 14.5, 22.7, 23, 28.6, 43.5, 96.1, 123.7, 124, 126.8, 127.6, 128.8, 129.7, 130, 131.1, 133.1, 138.6, 145.8, 149.4, 168.9. LCMS (ESI+) m/z 453.2 [M+H]$^+$. Anal. Calcd. for C$_{29}$H$_{29}$N$_3$O$_2$: C, 77.13; H, 6.47; N, 9.31%. Found C, 73.30; H, 6.25; N, 8.64%.

3-(4-t-Butylbenzyloxy)-2-[2-(3H-imidazol-4-yl)-ethyl]-3-phenyl-2,3-dihydroisoindolin-1-one (57) (NU8214)

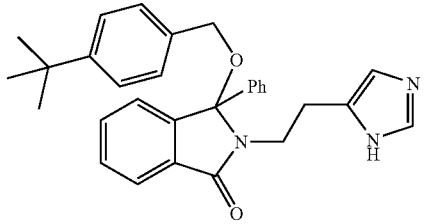

General procedure I: 10e (0.10 g, 0.32 mmol), 4-t-butyl-benzyl alcohol (0.06 mL, 0.35 mmol) in presence of triethylamine (0.10 mL, 0.70 mmol) in THF (8 mL). Trituration from petrol gave 57 as an off-white solid (80%) mp 187-188° C. UV $\lambda_{max}$=231 nm. FTIR ν (cm$^{-1}$): 3387 (NH), 3093-2954 (C—HAr), 1705 (C═O amide); $^1$H NMR (300 MHz, CDCl$_3$) $\delta_H$ (ppm) 1.22 (9H, s, t-Bu), 2.76 (1H, m, CH$_2$), 2.99 (1H, m, CH$_2$), 3.24 (1H, m, NCH$_2$), 4.4 (1H, m, NCH$_2$), 5.71 (2H, s, OCH$_2$), 6.90 (1H, bs, HNCH═N), 6.99 (1H, dd, J$_{H-H}$=2.8 Hz, C═CH), 7.35 (7H, m, Ar—H), 7.59 (1H, t, J$_{H-H}$=7.55 Hz, Ar—H), 7.83 (2H, t, 7.84 Hz, Ar—H), 8.5 (1H, d, J$_{H-H}$=7.67 Hz, Ar—H); $^{13}$C NMR (125 MHz, CDCl$_3$) $\delta_C$ (ppm) 19.8 (CH$_2$), 31.6 (CH$_3$), 32.7 (CH$_2$), 35.1 (CH), 53.8 (CH$_2$), 82 (CNO), 117.5-143.9 (CH—Ar), 153.2 (N═C—N), 167.4 (C═O). LCMS (ESI+): m/z=466, [M+Na]$^+$. Anal. Calc. for C$_{30}$H$_{31}$N$_2$O$_3$: C, 77.39; H, 6.71; N, 9.03%; Found: C, 67.63; H, 5.82; N, 7.73%.

2-Methylacrylic acid 2-{1-[2-(t-butyldimethylsilanyloxy)-1-(t-butyldimethylsilanyloxymethyl)-2-phenyl-ethylamino]-3-oxo-1-phenyl-1,3-dihydroisoindolin-2-yl}ethyl ester (90)

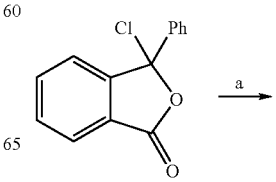

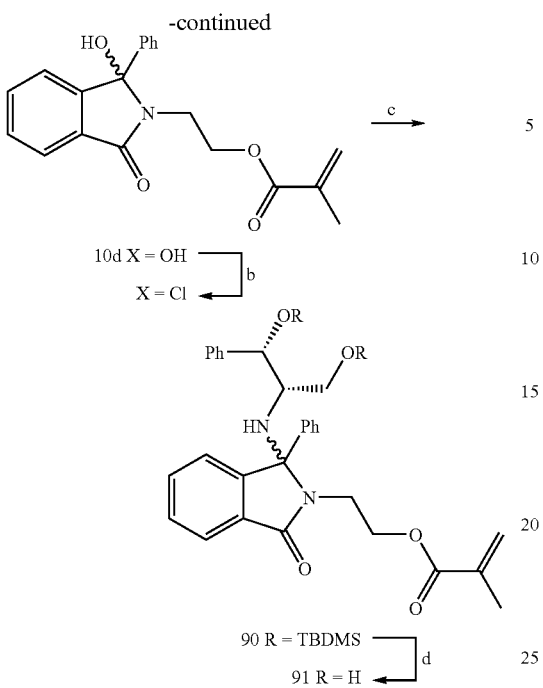

General procedure I: 10d (0.57 g, 1.7 mmol), 2-(t-butyldimethylsilanyloxy)-1-(t-butyldimethylsilanyloxymethyl)-2-phenylethylamine (0.74 g, 1.87 mmol), and triethylamine (0.52 mL, 3.74 mmol) in DMF (17 mL). Chromatography (EtOAc, petrol; 3:17) gave 90 as an oil (0.19 g, 0.2 mmol, 12%) as a mixture of diastereoisomers in 1:1 ratio. FTIR ν (cm$^{-1}$): 2933 (C—H Ar), 1699 (C=O). $^1$H NMR (300 MHz, CDCl$_3$) δ$_H$ (ppm) 0 (12H, m, 4CH$_3$), 0.91 (9H, d, t-Bu), 1.05 (9H, d, t-Bu), 1.70 (3H, s, CH$_3$), 1.98 (1H, d, CH$_2$), 2.4 (1H, m, NCH$_2$), 2.76 (1H, m, OCH$_2$), 3.03 (1H, m, OCH$_2$), 3.62 (3H, m, OCH$_2$ and OCH), 4.23 (1H, m, NCH), 5.06 (1H, s, CH), 5.27 (1H, s, CH), 5.63 (1H, s, CH), 6.16 (1H, s, CH), 7.35 (13H, m, Ar—H), 7.91 (1H, m, H$_4$); $^{13}$C NMR (75 MHz, CDCl$_3$) δ$_C$ (ppm) −5.6 (CH$_3$), −5.4 (CH$_3$), −5.3 (CH$_3$), −5.1 (CH$_3$), −4.7 (CH$_3$), −4.4 (CH$_3$), 17.9 (CH$_3$), 25.8 (CH$_3$), 25.9 (CH$_3$), 26 (CH$_3$), 35.8 (CH$_2$), 37.5 (CH$_2$), 59.6 (OCH$_2$), 60 (NCH$_2$), 61 (OCH), 72.1 (NCH), 82 (OCH$_2$), 123.2-143.

2-Methylacrylic acid 2-[1-(2-hydroxy-1-hydroxymethyl-2-phenylethylamino)-3-oxo-1-phenyl-1,3-dihydroisoindolin-2-yl]ethyl ester (91) (NU8216)

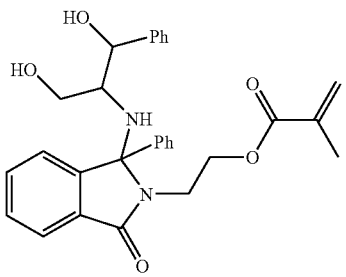

To a solution of 90 in THF (5 mL) was added TBAF (1 M in THF; 0.47 mL, 0.47 mmol). The mixture was stirred 16 h, then diluted with water (5 mL) and extracted with EtOAc (3×10 mL). The organic layers were combined and washed with saturated brine (10 mL), dried (MgSO$_4$), and concentrated in vacuo. Chromatography (EtOAc, petrol; 95:5), gave 91 (0.08 g, 0.20 mmol, 76%) as a single diastereoisomer, m$^p$187-188° C. UV λ$_{max}$=237 nm. FTIR ν (cm−1) 3343 (NH, OH), 3032-2932 (C—H Ar), 1672 (C=O); $^1$H NMR (300 MHz, CDCl$_3$) δ$_H$ (ppm) 1.77 (3H, s, CH$_3$), 2.14 (1H, dd, CH$_2$OH), 2.18 (1H, bs, OH), 2.50 (1H, dd, CH$_{2dia}$OH), 2.45 (1H, bs, OH$_{dia}$), 3 (1H, q, NCH$_2$), 3.10 (1H, bs, NH), 3.40 (3H, m, NCH$_2$, NCH$_{dia}$), 3.80 (2H, m, OCH$_2$), 4.74 (1H, dd, J$_{H-H}$=5.2 Hz, CHOH), 5.43 (1H, d, J$_{H-H}$=1.53 Hz, CH), 5.94 (1H, d, J$_{H-H}$=1.04 Hz, CH), 6.28 (1H, d, J$_{H-H}$=7.58 Hz, Ar—H), 7.12-7.37 (13H, m, Ar—H), 7.70 (1H, m, Ar—H$_4$); $^{13}$C NMR (75 MHz, CDCl$_3$) δ$_C$ (ppm): 18.6 (CH$_3$), 37.5 (CH$_2$), 58.2 (NCH$_2$), 61.4 (OCH$_2$), 62.9 (CH$_2$), 76.0 (CH), 82 (C), 123.3-149.5 (C—Ar), 167.3 (C=O), 169.4 (C=O). LCMS (ESI+) m/z=487, [M+H]$^+$.

4-(3-Oxo-1-phenyl-1-propoxy-1,3-dihydro-isoindolin-2-yl)butyraldehyde (80)

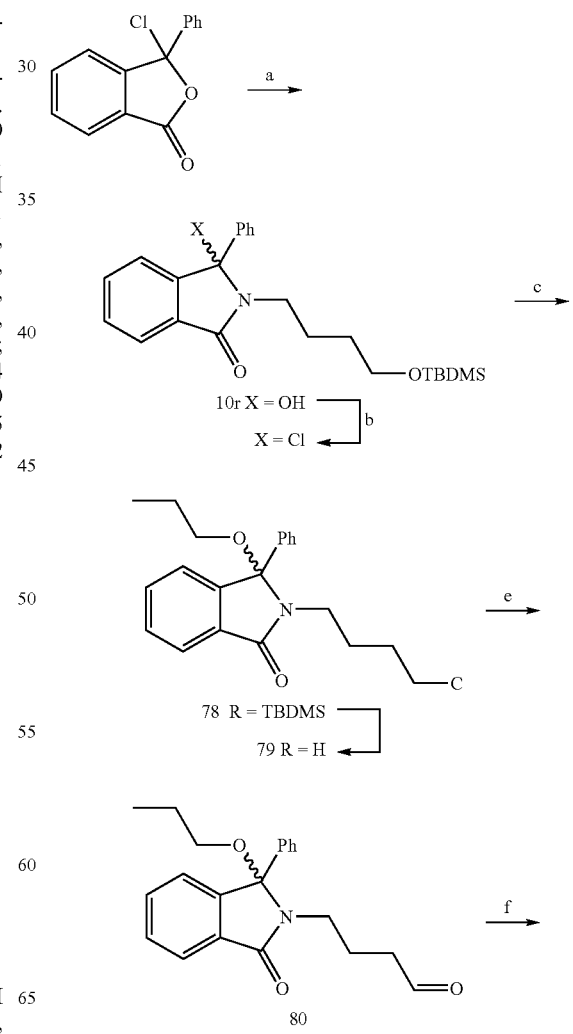

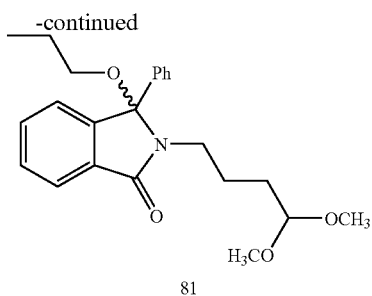

81

TBAF (1M solution in THF; 230 mg, 0.87 mmol) and 78 (250 mg, 0.43 mmol) in THF (10 mL) gave 79 (140 mg, 100%) which was used without further purification. To a solution of oxalyl chloride (72 μL, 0.83 mmol) in dry DCM (10 mL), a solution of DMSO (71 mg, 0.91 mmol) in DCM (2 mL) was added dropwise at −78° C. under nitrogen atmosphere. After 30 min, a solution of 79 (140 mg, 0.41 mmol) in DCM (10 mL) was added dropwise for 10 min. and stirring was continued at −78° C. for 30 min. Triethylamine (0.209 mg, 2.06 mmol) was added and the reaction mixture allowed to warm to rt and quenched with water (50 mL). The organic layer was separated and the aqueous layer was extracted with DCM (2×50 mL). The combined organic extracts were washed with water (3×30 mL), brine (30 mL), dried and concentrated. Chromatography (silica: 40% EtOAc, petroleum ether) gave 80 as colourless oil. (127 mg, 91%). IR ν (cm$^{-1}$) 2933, 2724, 1697, 1453, 1371, 1182, 1042, 850, 757, 694. $^1$H-NMR (300 MHz, CDCl$_3$) δ$_H$ 9.55 (1H, s, CHO); 7.78 (1H, m, Ar); 7.41 (2H, m, Ar); 7.29 (2H, m, Ar); 7.23 (3H, m, Ar); 7.07 (1H, m, Ar); 3.19 (2H, m, OCH$_2$); 3.00 (1H, m, NCH$_2$); 2.76 (1H, m, NCH$_2$); 2.26 (2H, m, CH$_2$CHO); 1.57 (4H, m, 2×CH$_2$); 0.86 (3H, t, J=7.37 Hz, CH$_3$). $^{13}$C-NMR (75 MHz, CDCl$_3$) δ$_C$ 11.21, 21.25, 23.14, 38.89, 41.84, 64.58, 95.13, 123.52, 123.65, 126.66, 128.81, 128.91, 129.97, 132.26, 132.86, 139.51, 146.19, 168.97, 201.83.

2-(4,4-Dimethoxybutyl)-3-phenyl-3-propoxy-2,3-dihydroisoindolin-1-one (81) (NU8217)

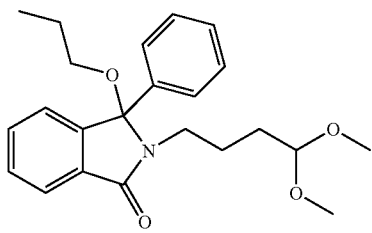

A mixture of 80 (120 mg, 0.36 mmol), dry methanol (10 mL) and ammonium chloride (cat) was heated at 50° C. for 36 h, then concentrated in vacuo and extracted with EtOAc (100 mL), washed with water (2×50 mL), brine (50 mL), dried and concentrated. Chromatography (silica: 30% EtOAc, petroleum ether) gave 81 as a colorless viscous oil (83 mg, 61%). IR ν (cm$^{-1}$): 2934, 1697, 1453, 1368, 1180, 1048, 853, 757, 693. $^1$H-NMR (300 MHz, CDCl$_3$) δ$_H$ 7.78 (1H, m, Ar), 7.39 (2H, m, Ar), 7.29 (2H, m, Ar), 7.22 (3H, m, Ar), 7.06 (1H, m, Ar), 4.16 (1H, t, J=5.55 Hz, CH(OMe)$_2$), 3.2 (1H, m, OCH$_2$), 3.16 (3H, s, OMe), 3.15 (3H, s, OMe), 3.06 (1H, m, OCH$_2$ and NCH$_2$), 2.76 (1H, m, NCH$_2$), 2.31 (2H, m, OCH$_2$CH$_2$CH$_3$), 1.43 (3H, m, NCH$_2$CH$_2$CH$_2$CH), 1.30 (1H, m, NCH$_2$CH$_2$CH$_2$CH), 0.87 (3H, t, J=7.46 Hz, OCH$_2$CH$_2$CH$_3$). $^{13}$C-NMR (75 MHz, CDCl$_3$) δ$_C$ 11.20, 23.14, 23.79, 30.61, 39.63, 52.98, 53.50, 64.50, 95.22, 104.52, 123.42, 123.62, 126.71, 128.73, 129.86, 132.44, 132.68, 139.63, 146.24, 168.77. LCMS (ESI+) 406 [M+1]$^+$.

3-((R)-2-(tert-Butyldiphenylsilyloxy)-2-(4-methoxyphenyl)ethylamino)-2-(3-(tert-butyldiphenylsilyloxy)propyl)-3-phenylisoindolinin-1-one (66)

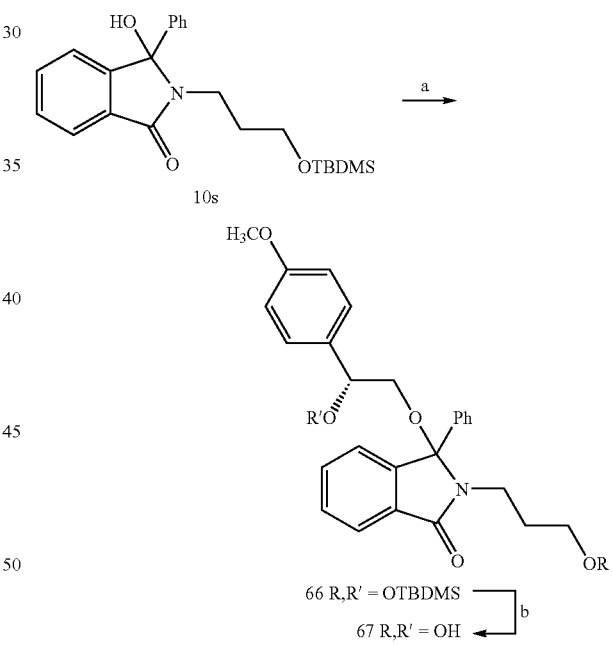

General procedure I: 10s (370 mg, 0.7 mmol), thionyl chloride (126 mg, 1.1 mmol), THF (10 mL), (R)-2-(tert-butyldiphenylsilanyloxy)-2-(4-methoxyphenyl)ethyl amine (344 mg, 0.85 mmol), triethylamine (143 mg, 1.4 mmol), DMF (10 mL). Chromatography (20% EtOAc, petrol) gave 66. $^1$H-NMR: δ$_H$ (300 MHz, CDCl$_3$): 7.82 (1H, m, Ar); 7.47-7.10 (32H, m, Ar); 6.74 (1H, dd, J=8.72 Hz, Ar); 5.03 (1H, m, —CH—OSi); 3.85-3.68 (5H, m, —OCH$_2$, —OCH$_3$); 3.06 (4H, m, —NCH$_2$); 2.03 (1H, m, —CH$_2$); 1.74 (1H, m, —CH$_2$); 1.05 (9H, s, $^t$Bu); 0.92 (9H, s, $^t$Bu). $^{13}$C-NMR: δ$_C$ (75 MHz, CDCl$_3$): 19.54, 27.06, 27.45, 31.03, 37.81, 48.01, 49.18, 55.59, 60.80, 63.30, 73.39, 74.78, 90.93, 91.43, 91.96, 113.86, 123.56, 126.58, 127.77, 128.09, 128.24, 128.98, 130.13, 135.92, 136.21, 136.58, 139.57, 149.67, 159.26, 168.35.

3-((R)-2-Hydroxy-2-(4-methoxyphenyl)ethylamino)-2-(3-hydroxypropyl)-3-phenylisoindolin-1-one (67) (NU8218)

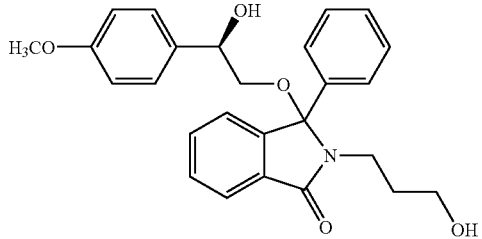

66 (400 mg, 0.44 mmol), tetrabutylammonium fluoride (345 mg, 1.32 mmol; 1M solution in THF), THF (10 mL). Chromatography (40% EtOAc, petrol) gave 67 as a white solid. IR ν (cm$^{-1}$): 3386, 3047, 2924, 1635, 1446, 1407, 1342, 1219, 1176, 1020, 934, 815, 748, 678. $^1$H-NMR: δ$_H$ (300 MHz, CD$_3$OD): 7.8 (1H, m, Ar); 7.57 (2H, m, Ar); 7.38 (5H, m, Ar); 7.25 (3H, m, Ar); 6.48 (2H, m, Ar), 4.73 (1H, dd, J=3.45 & 9.13 Hz, —CH—OH); 3.89 (1H, dd, J=8.0 & 14.4 Hz, —OCH$_2$—); 3.76 (3H, s, —OCH$_3$); 3.72 (1H, dd, —OCH$_2$—); 3.32 (4H, m, —NCH$_2$—); 3.12 (2H, m, —CH$_2$—). $^{13}$C-NMR: δ$_C$ (125 MHz, CD$_3$OD): 56.05, 73.57, 74.03, 92.79, 93.50, 115.04, 115.15, 124.39, 124.45, 127.69, 127.77, 128.83, 129.96, 130.02, 130.14, 130.98, 131.70, 131.75, 134.57, 134.61, 135.59, 135.78, 140.85, 141.00, 151.35, 151.40, 161.03, 161.14, 170.94, 171.24. Anal. Calcd. for C$_{26}$H$_{28}$N$_2$O$_4$: C, 72.20; H, 6.53; N, 6.48. Found: C, 73.11; H, 5.65; N, 3.30.

3-[(R)-2-(tert-Butyldiphenylsilanyloxy)-2-(4-methoxyphenyl)ethylamino]-2-furan-2-ylmethyl-3-phenyl-2,3-dihydroisoindolin-1-one (70)

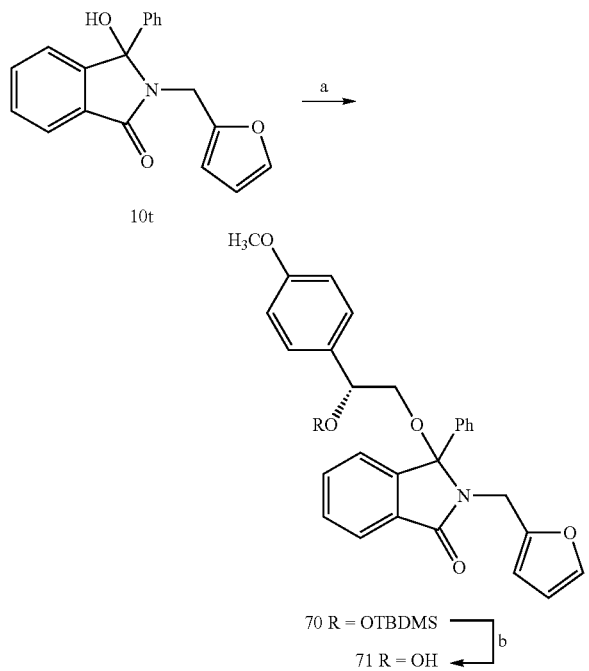

General procedure I: 10t (200 mg, 0.65 mmol), thionyl chloride (116 mg, 0.98 mmol), (R)-2-(tert-butyldiphenylsilanyloxy)-2-(4-methoxyphenyl)ethylamine (317 mg, 0.78 mmol), triethylamine (132 mg, 1.3 mmol), DMF (10 mL). Chromatography (silica: 40% EtOAc, petroleum ether) gave 70 as a light brown solid (240 mg, 53%) LCMS (ESI+) 693 [M+H]$^+$.

NU8219 2-Furan-2-ylmethyl-3-[2-hydroxy-2-(4-methoxyphenyl)ethylamino]-3-phenyl-2,3-dihydroisoindolin-1-one (71)

TBAF (1M solution in THF; 345 mg, 1.3 mmol) and 70 (400 mg, 0.44 mmol) in THF (10 mL) gave 72 as an off white solid (175 mg, 89%). IR ν=3342, 3064, 2910, 2838, 1658, 1448, 1408, 1404, 1226, 1175, 1031, 833, 748 cm$^{-1}$. $^1$H-NMR (300 MHz, CDCl$_3$) δ$_H$ 7.76 (1H, m, Ar); 7.29 (8H, m, Ar); 7.10 (2H, m, Ar); 6.95 (2H, t, J=8.44 Hz, Ar); 6.72 (2H, m, CH and NH); 6.23 (1H, m, furan); 6.17 (1H, m, furan); 4.92 (1H, dd, J=15.75 Hz, NCH$_2$); 4.30 (1H, m, CHOH), 3.92 (1H, dd, J=15.75 Hz, NCH$_2$); 3.69 (3H, d, J=3.34 Hz, OCH$_2$); 2.59 (1H, br, OH); 1.98 (2H, m, NHCH$_2$). $^{13}$C-NMR (125 MHz, CDCl$_3$) δ$_C$ 35.48, 35.59, 48.99, 49.98, 55.66, 72.92, 84.20, 109.55, 109.77, 111.04, 111.40, 114.02, 114.14, 122.99, 123.16, 124.10, 124.15, 126.44, 127.28, 127.36, 128.77, 128.94, 129.34, 129.47, 131.28, 132.91, 133.06, 133.90, 134.69, 139.79, 140.03, 142.24, 142.31, 147.75, 148.20, 151.08, 151.32, 159.47, 168.44, 168.76. LCMS (ESI+) 455 [M+H]$^+$. Anal. Calcd. for C$_{28}$H$_{26}$N$_2$O$_4$ C, 73.99; H, 5.77; N, 6.16. Found: 72.15; H, 5.67; N, 5.49.

3-Amino-2-cyclohexylmethyl-3-(4-isobutoxyphenyl)isoindolinone

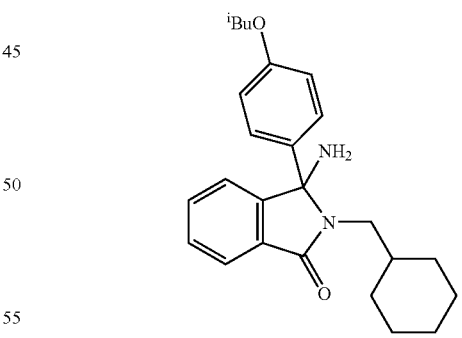

General procedure K. 4-isobutoxybenzonitrile, gave off white crystals (687 mg, 77%). Mpt 87.2-91.6° C., $^1$H-NMR: δ$_H$ (300 MHz, CDCl$_3$): 0.87 (2H, m, CH$_2$); 0.93 (6H, d, J=6.7 Hz, 2×CH$_3$); 1.07 (2H, m, CH); 1.55 (7H, m, CH); 1.99 (3H, m, CH, NH$_2$); 2.66 (1H, m, NCH$_2$), 3.37 (1H, m, NCH$_2$); 3.61 (2H, d, J=6.53 Hz, OCH$_2$); 6.67 (2H, d, J=8.9 Hz, ArH); 7.22 (3H, m, ArH); 7.35 (2H, m, ArH); 7.74 (1H, m, ArH). $^{13}$C-NMR: δ$_C$ (125 MHz, CDCl$_3$): 19.6, 26.3, 26.7, 28.6, 31.5, 31.7, 38.0, 47.1, 74.9, 79.8, 115.6, 122.5, 124.0, 127.0, 127.4, 129.0, 129.2, 130.5, 131.0, 132.5, 134.5, 148.5, 160.1, 166.8, 169.4. Anal. Calcd. for $C_{25}H_{32}N_2O_2$: C, 76.49; H, 8.22; N, 7.14. Found: C, 76.12; H, 8.27; N, 7.02

3-Amino-2-cyclohexylmethyl-3-(4-ethoxyphenyl)isoindolinone

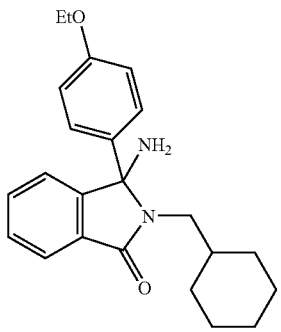

General procedure K. 4-ethoxylbenzonitrile, gave off white crystals (262 mg, 63%). Mpt 153-154° C., $^1$H-NMR: $\delta_H$ (300 MHz, CDCl$_3$): 0.97 (2H, m, CH$_2$); 1.14 (2H, m, CH$_2$); 1.41 (3H, t, J=6.99 Hz, CH$_3$); 1.66 (7H, m, CH, CH$_2$); 2.11 (2H, S, NH$_2$), 2.76 (1H, m, NCH$_2$); 3.45 (1H, m, NCH$_2$); 4.01 (2H, q, J=7.02 Hz, OCH$_2$); 6.84 (2H, m, ArH); 7.31 (3H, m, ArH); 7.46 (2H, m, ArH); 7.82 (1H, m, ArH). $^{13}$C-NMR: $\delta_C$ (125 MHz, CDCl$_3$): 14.9, 26.0, 26.1, 26.5, 31.4, 31.8, 36.6, 37.3, 80.1, 114.7, 122.5, 123.4, 127.6, 128.8, 130.7, 132.1, 132.3, 150.9, 159.0, 168.4. Anal. Calcd. for $C_{23}H_{28}N_2O_2$: C, 75.79; H, 7.74; N, 7.69. Found: C, 75.39; H, 7.99; N, 7.46.

3-Amino-2-cyclohexylmethyl-3-(4-methanesulphanylphenyl)isoindolinone

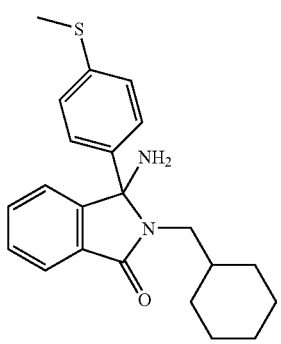

General procedure K. 4-methanesulphanylbenzonitrile, gave off white crystals (499 mg, 60%). Mpt 114-116° C., $^1$H-NMR: $\delta_H$ (300 MHz, CDCl$_3$): 0.87 (2H, m, CH$_2$); 1.07 (2H, m, CH$_2$); 1.56 (7H, m, CH); 2.03 (2H, s, NH$_2$), 2.39 (3H, s, SCH$_2$); 2.64 (1H, m, NCH$_2$); 3.39 (1H, m, NCH$_2$); 7.11 (2H, m, ArH); 7.23 (3H, m, ArH); 7.37 (2H, m, ArH); 7.75 (1H, m, ArH). $^{13}$C-NMR: $\delta_C$ (125 MHz, CDCl$_3$): 14.9, 26.0, 26.1, 26.5, 31.4, 31.8, 36.6, 37.3, 80.1, 114.7, 122.5, 123.4, 127.6, 128.8, 130.7, 132.1, 132.3, 150.9, 159.0, 168.4. Anal. Calcd. for $C_{22}H_{26}N_2OS$: C, 72.09; H, 7.31; N, 7.49. Found: C, 72.14; H, 7.31; N, 7.46.

N-[2-Cyclohexylmethyl-1-(4-isobutoxyphenyl)-3-oxo-2,3-dihydro-1H-isoindolin-1-yl]benzamide (NU8200)

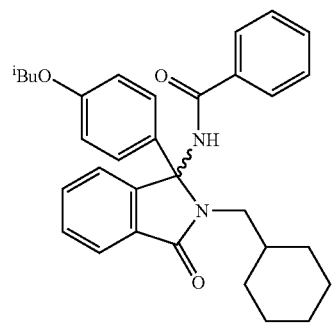

General Procedure L: 3-Amino-2-cyclohexylmethyl-3-(4-isobutoxyphenyl)isoindolininone, gave a white powder (236 mg, 93%). Mpt 138-141° C., $^1$H-NMR: $\delta_H$ (300 MHz, CDCl$_3$): 0.89 (10H, m, 2×CH$_3$, CH$_2$); 1.49 (7H, m, CH$_2$); 1.68 (1H, m, CH); 2.90 (1H, m, NCH$_2$); 3.63 (2H, d, J=6.65 Hz, OCH$_2$), 6.83 (3H, m, ArCH, NH); 7.21 (4H, m, ArH); 7.43 (4H, m, ArH); 7.73 (2H, m, ArH); 7.80 (1H, m, ArH). $^{13}$C-NMR: $\delta_C$ (125 MHz, CDCl$_3$): 19.6, 26.3, 26.7, 28.6, 31.5, 31.7, 38.0, 47.1, 74.9, 79.8, 115.6, 122.5, 124.0, 127.0, 127.4, 129.0, 129.2, 130.5, 131.0, 132.5, 134.5, 148.5, 160.1, 166.8, 169.4. Anal. Calcd. for $C_{32}H_{36}N_2O_3 \cdot 0.4H_2O$: C, 77.39; H, 7.31; N, 5.56. Found: C, 77.28; H, 7.36; N, 5.56.

N-[2-Cyclohexylmethyl 1-(4-ethoxyphenyl)-3-oxo-2,3-dihydro-1H-isoindolin-1-yl]benzamide (NU8201)

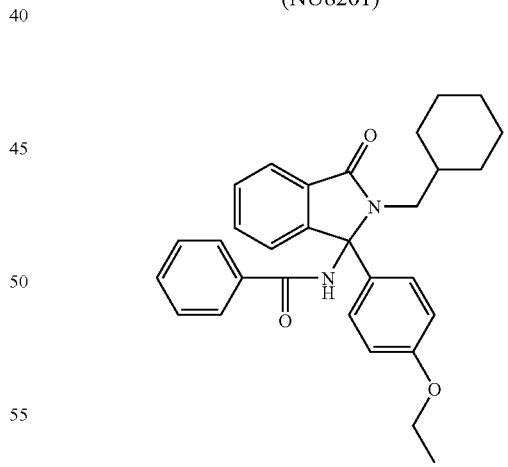

General Procedure L: 3-Amino-2-cyclohexylmethyl-3-(4-ethoxyphenyl)isoindolininone, gave a white powder (81 mg, 78%). Mpt 177-178° C., $^1$H-NMR: $\delta_H$ (300 MHz, CDCl$_3$): 0.86 (4H, m, 2×CH$_2$); 1.33 (3H, t, J=6.98, CH$_3$); 1.50 (6H, m, CH$_2$); 1.67 (1H, m, CH$_2$); 2.90 (2, m, NCH$_2$), 3.52 (1H, m, NCH$_2$); 3.95 (2H, q, J=6.85, OCH$_2$); 6.83 (3H, m, ArH); 7.21 (3H, m, ArH); 7.43 (5H, m, ArH); 7.76 (3H, m, ArH). $^{13}$C-NMR: $\delta_C$ (125 MHz, CDCl$_3$):14.8, 25.96, 25.97, 26.34, 31.17, 31.36, 37.71, 46.75, 63.66, 79.42, 155.19, 122.19, 123.61, 126.76, 127.05, 128.68, 128.87, 130.26, 130.66, 132.19, 134.20, 148.11, 159.43, 166.43, 169.08. Anal. Calcd. for $C_{30}H_{32}N_2O_3$: C, 76.82; H, 6.79; N, 5.92. Found: C, 76.90; H, 6.88; N, 5.98.

N-[2-Cyclohexylmethyl-1-(4-methylsulfanylphenyl)-3-oxo-2,3-dihydro-1H-isoindolin-1-yl]benzamide (NU8202)

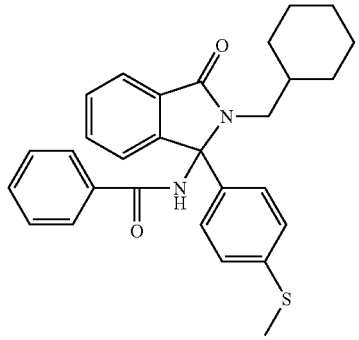

2-Benzyl-3-(4-methoxybenzyloxy)-3-phenyl-2,3-dihydroisoindolin-1-one (NU8226)

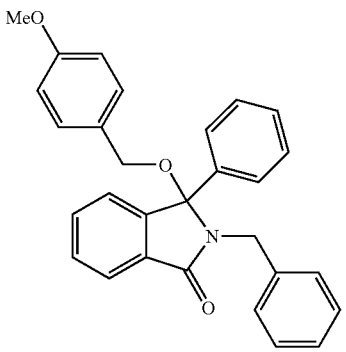

2-Benzyl-3-chloro-3-phenyl-2,3-dihydroisoindolin-1-one (316 mg, 0.95 mmol) was reacted with para-methoxybenzyl alcohol (0.26 mL, 2.1 mmol) as for general procedure C. The crude product was purified by flash column chromatography (30:70 EtOAc:petrol) to give 2-benzyl-3-(4-methoxybenzyloxy)-3-phenyl-2,3-dihydroisoindol-1-one as a colourless oil (363 mg, 0.8 mmol, 87%); $R_f$ 0.57 (40:60 EtOAc:petrol). $\lambda_{max}$ (CH$_3$OH)/nm 205, Abs 0.923. IR: 3024, 2928, 1698, 1489 cm$^{-1}$. $^1$H NMR: (300 MHz, CDCl$_3$) δ 3.56 (d, 1H, J=10.5 Hz, O—CH$_2$), 3.64 (d, 1H, J=10.6, O—CH$_2$), 3.71 (s, 3H, OMe), 3.95 (d, 1H, J=14.7 Hz, N—CH$_2$), 4.74 (d, 1H, J=14.7 Hz, N—CH$_2$), 6.68 (d, 2H, J=6.5 Hz, Ar—H), 6.75 (d, 2H, J=6.6 Hz, Ar—H), 7.10 (m, 4H, Ar—H), 7.23 (m, 7H, Ar—H), 7.42 (m, 2H, Ar—H), 7.88 (m, 1H, Ar—H). $^{13}$C NMR: (75 MHz, CDCl$_3$) δ 43.7, 55.5, 64.8, 95.9, 113.8, 123.4, 126.8, 127.4, 128.5, 128.7, 129.4, 129.7, 132, 132.9, 137.9, 138.8, 146.1, 159.3, 168.6. LC/MS-ES$^+$ m/z 298.1, 436 [MH$^+$], 458.1 [MNa$^+$]. Anal. Calcd. for $C_{29}H_{25}NO_3$·0.4H$_2$O: C, 78.84; H, 5.86; N, 3.17%. Found C, 79.33; H, 5.39; N, 2.71%.

3-(4-Chlorophenyl)-2-(4-nitrobenzyl)-3-(2,4,6-trihydroxyphenyl)-2,3-dihydro-isoindolin-1-one (NU8262)

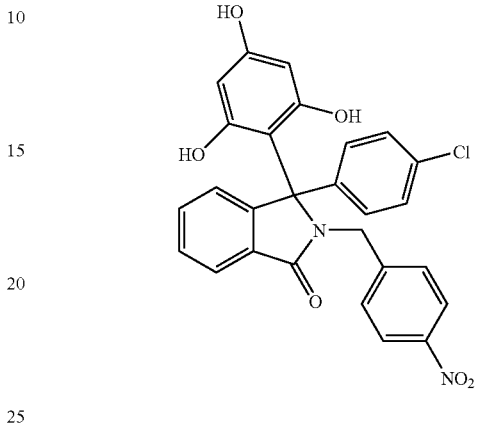

3-Chloro-3-(4-chlorophenyl)-2-(4-nitrobenzyl)-2,3-dihydroisoindolin-1-one (156 mg, 0.37 mmol) was reacted with phloroglucinol (479 mg, 3.79 mmol) as for general procedure C. The crude product was purified by HPLC (H$_2$O:MeOH, 270 nm) to give 3-(4-chlorophenyl)-2-(4-nitrobenzyl)-3-(2,4,6-trihydroxyphenyl)-2,3-dihydroisoindol-1-one as a pale yellow solid (115 mg, 0.22 mmol, 61%); $R_f$=0.14 (40:60: EtOAc: petrol). mp 196.3-198.5° C. $\lambda_{max}$ (CH$_3$OH)/nm 230.5, Abs 0.994. IR: 3218, 1654, 1603, 1515, 1340 cm$^{-1}$. $^1$H NMR: (300 MHz, d$_6$-DMSO) δ 4.78 (d, 1H, J=16.9 Hz, N—CH$_2$), 4.94 (d, 1H, J=17 Hz, N—CH$_2$), 5.58 (s, 2H, Ar—H), 7.03-7.21 (m, 6H, Ar—H), 7.36 (t, 1H, J=6.6 Hz, Ar—H), 7.48 (m, 2H, Ar—H), 7.65 (d, 1H, J=7.4 Hz, Ar—H), 7.86 (d, 1H, J=8.7 Hz, Ar—H), 9.10 (s, 2H, Ar—OH), 9.27 (bs, 1H, Ar—OH). $^{13}$C NMR: (75 MHz, d$_6$-DMSO) δ 44, 71.8, 95.5, 101.1, 122.7, 122.8, 123.9, 125.2, 127.1, 127.7, 128.5, 129.3, 130.7, 132, 144, 145.9, 147, 153.2, 158.4, 158.6, 168.2. LC/MS-ES$^+$ m/z 503.1, 504.1, 505.1. Anal. Calcd. for $C_{27}H_{19}ClN_2O_6$: C, 64.48; H, 3.81; N, 5.57%. Found C, 63.11; H, 3.97; N, 5.53%. HRMS (EI) m/z Calcd. for $C_{27}H_{19}ClN_2O_6$: 502.0931. Found 502.0912.

2-(4-Hydroxy)benzoylbenzoic acid

Phenolphthalein (7 g, 22 mmol) was dissolved in aqueous potassium hydroxide solution (7 g in 70 mL) giving a vivid purple solution. Hydroxylamine hydrochloride (1.71 g, 24 mmol) was added and the solution heated to 80° C. The reaction was monitored by acidifying a sample of the mixture with acetic acid, filtering off the precipitate and adding potassium hydroxide. When no pink colour was observed on the addition of potassium hydroxide the reaction was left stirring for another 5 min. Ethanol (14 mL) was added, and acetic acid was added dropwise until the solution was slightly acidic. A sulphur yellow precipitate formed and was washed with water and dissolved in hot sulphuric acid (10%, 140 mL) giving a bright yellow solution that was refluxed for 2 h. On cooling a deep yellow solid was obtained filtered and washed with ice cold water yielding 2-(4-Hydroxy)benzoylbenzoic acid as a light yellow solid (4.04 g, 16.6 mmol, 76%); $R_f$ 0.06 (40:60 EtOAc:petrol). mp 228.4-230.6° C. Lit. 231° C.[8] IR: 3232, 3163, 1688, 1644, 1577, 1381 cm$^{-1}$. $^1$H NMR: (300 MHz, d$_6$-DMSO) δ 6.83 (m, 2H, Ar—H), 7.34 (dd, 1H, J=7.4, 1.3 Hz, Ar—H), 7.50 (m, 2H, Ar—H), 7.58-7.71 (dtd, 2H, J=22.4, 7.4, 1.3 Hz, Ar—H), 7.95 (dd, 1H, J=7.6, 1.3 Hz, Ar—H), 10.30 (bs, 1H, COOH). $^{13}$C NMR: (75 MHz, d$_6$-DMSO) δ 115.5, 127.7, 128.6, 129.6, 130, 130.1, 131.9, 132.4, 142.2, 162.4, 167.3, 195.1. LC/MS-ES$^+$ m/z 129.3, 225.1, 264.9, 506.8.

2-(4-Hydroxybenzoyl)benzoic acid methyl ester

Acetyl chloride (2.67 mL, 37.5 mmol), was added dropwise to ice cold methanol (40 mL) whilst stirring. 2-(4-Hydroxy)benzoylbenzoic acid (3.9 g, 16.1 mmol) was added and the mixture was allowed to warm to room temperature. After 16 h the solvent was removed leaving a light green oil which was triturated with water, washed with ice cold petrol and dried in vacuo giving 2-(4-hydroxybenzoyl)benzoic acid methyl ester as a light green solid (3.8 g, 14.8 mmol, 92%); R$_f$ 0.43 (40:60 EtOAc:petrol). mp 147.1-149.3° C. Lit. 149-150° C. 9 IR: 3338, 1719, 1644, 1569, 1511, 1432 cm–1. $^1$H NMR: (300 MHz, d6-DMSO) δ 3.58 (s, 3H, COOCH$_3$), 6.84 (d, 2H, J=8.6 Hz, Ar—H), 7.41 (d, 1H, J=7.3 Hz, Ar—H), 7.51 (d, 2H, J=8.6, Ar—H), 7.61-7.74 (dt, 2H, J=24.2, 6.5 Hz, Ar—H), 7.95 (d, 1H, J=7.4 Hz, Ar—H), 10.47 (bs, 1H, COOH). $^{13}$C NMR: (75 MHz, d6-DMSO) δ 52.4, 115.7, 127.7, 128.5, 129.6, 129.9, 130.1, 131.9, 132.4, 141.9, 162.5, 166.3, 194.7. LC/MS-ES+m/z 256.9 [M+H]+.

2-[4-(2-Trimethylsilanylethoxymethoxy)benzoyl] benzoic acid methyl ester

A mixture of 2-(4-hydroxybenzoyl)benzoic acid methyl ester (3.65 g, 15 mmol), cesium carbonate (5.4 g, 16.5 mmol), and trimethylsilylethoxymethylchloride (2.9 mL, 16.5 mmol), in CH$_3$CN (50 mL) was stirred at rt 24 h, the concentrated in vacuo. The residues were dissolved in ethyl acetate (100 mL), washed with water (3×50 mL), brine (40 mL), dried (MgSO$_4$), and concentrated in vacuo. Chromatography (EtOAc:petrol; 5:95) to give the product as a yellow oil (3.94 g, 10.2 mmol, 67%). λ$_{max}$ (CH$_3$OH)/nm 282, Abs 1.072. IR: 2939, 1720, 1666, 1589, 1489 cm$^{-1}$. $^1$H NMR: (300 MHz, CDCl$_3$) δ 0.00 (s, 9H, Si—(CH$_3$)$_3$), 0.94 (m, 2H, R—O—CH$_2$—CH$_2$—Si), 3.66 (s, 3H, COOCH$_3$), 3.75 (m, 2H, O—CH$_2$—CH$_2$—Si), 5.27 (s, 2H, O—CH$_2$—O), 7.05 (m, 2H, Ar—H), 7.37 (m, 1H, Ar—H), 7.53-7.66 (dtd, 2H, J=22.4, 7.4, 1.4 Hz, Ar—H), 7.72 (m, 2H, Ar—H), 8.05 (m, 1H, Ar—H). $^{13}$C NMR: (75 MHz, d$_6$-DMSO) δ -2, 16.8, 51.5, 65.3, 91.5, 115.1, 127, 128, 129, 129.2, 129.6, 130.4, 132, 140.7, 160.2, 165.2, 194. LCMS (ESI+) m/z 387 [M+H]$^+$, 409 [M+Na]$^+$. HRMS (EI) m/z Calcd. for C$_{21}$H$_{26}$O$_5$Si: 386.1549. Found 386.1562.

2-[4-(2-Trimethylsilanylethoxymethoxy)benzoyl] benzoic acid

To a solution of 2-[4-(2-trimethylsilanylethoxymethoxy) benzoyl]-benzoic acid methyl ester (3.8 g, 9.8 mmol) in DCM (25 mL) was added potassium trimethylsilanolate (1.53 g, 10.8 mmol) and the mixture stirred 16 h, then concentrated in vacuo. The residues were dissolved in ethyl acetate (100 mL), washed with 5% HCl solution (3×30 mL), brine (30 mL), dried (MgSO$_4$) and concentrated in vacuo to give the product as a yellow oil (3.66 g, 9.8 mmol, 99%). λ$_{max}$ (CH$_3$OH)/nm 276, 217, Abs 1.799, 2.108 respectively. IR 3215, 3177, 1666, 1593 cm$^{-1}$. $^1$H NMR (300 MHz, CDCl$_3$) δ 0.00 (s, 9H, Si—(CH$_3$)$_3$), 0.96 (m, 2H, R—O—CH$_2$—CH$_2$—Si), 3.76 (m, 2H, O—CH$_2$—CH$_2$—Si), 5.27 (s, 2H, O—CH$_2$—O), 7.04 (m, 2H, Ar—H), 7.34 (m, 1H, Ar—H), 7.52-7.68 (dtd, 2H, J=30.2, 7.6, 1.3 Hz, Ar—H), 7.69 (m, 2H, Ar—H), 8.07 (m, 1H, Ar—H), 10.31 (bs, 1H, COOH). $^{13}$C NMR (75 MHz, CDCl$_3$) δ -3.2, 16.1, 64.8, 90.7, 113.8, 125.7, 126, 127.4, 128.8, 129.1, 129.9, 131.2, 140.9, 159.6, 168.8, 194. LCMS (ESI+) m/z 297.1, 373.1 [M+H]$^+$. HRMS (EI) m/z Calcd. for C$_{20}$H$_{24}$O$_5$Si: 372.1393. Found 372.1387.

2-Benzyl-3-hydroxy-3-[4-(2-trimethylsilanylethoxymethoxy)phenyl]-2,3-dihydroisoindol-1-one (NU8239)

General procedure A: 2-[4-(2-trimethylsilanylethoxymethoxy)benzoyl]benzoic acid (1.86 g, 5 mmol), thionyl chloride (0.43 mL, 6 mmol) and 3 drops of DMF in THF (10 mL), 2 h. Then benzylamine (1.1 mL, 10 mmol), and triethylamine (1.39 mL, 10 mmol), in THF (10 mL), 2 h. Chromatography (20:80 EtOAc:petrol) and (C18 silica; 20% MeOH, H$_{20}$ to 100% MeOH gradient) gave the title compound as a clear yellow oil (140 mg, 0.3 mmol, 0.6%). λ$_{max}$ (CH$_3$OH)/nm 213, Abs 1.161. IR: 3306, 2953, 1677, 1609, 1508, 1469 cm$^{-1}$. $^1$H NMR (300 MHz, CDCl$_3$) δ 0.00 (s, 9H, Si—(CH$_3$)$_3$), 0.95 (m, 2H, R—O—CH$_2$—CH$_2$—Si), 2.90 (bs, 1H, OH), 3.74 (m, 2H, O—CH$_2$—CH$_2$—Si), 4.06 (d, 1H, J=14.9 Hz, N—CH$_2$), 4.77 (d, 1H, J=14.9 Hz, N—CH$_2$), 5.19 (s, 2H, O—CH$_2$—O), 6.92 (m, 2H, Ar—H), 7.12-7.29 (m, 8H, Ar—H), 7.45 (m, 2H, Ar—H), 7.80 (m, 1H, Ar—H). $^{13}$C NMR (75 MHz, CDCl$_3$) δ -1.9, 17.4, 42.3, 65.7, 91, 92.2, 115.5, 122, 122.8, 126.4, 127, 127.6, 128.1, 128.9, 129.6, 130.5, 132.1, 137.6, 148.4, 156.9, 167. LCMS (ESI+) m/z 484 [M+Na]$^+$. HRMS (EI) m/z Calcd. for C$_{27}$H$_{31}$NO$_4$Si: 461.2022. Found 461.2017.

3-(4-Chlorophenyl)-3-hydroxy-2-(4-nitrobenzyl)-2, 3-dihydroisoindol-1-one (NU8260)

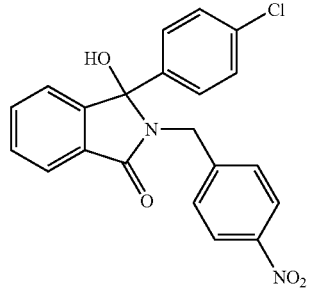

Distilled THF (25 mL) was added to 3-chloro-3-(4-chlorophenyl)-3H-isobenzofuran-1-one (3.2 g, 11.5 mmol) followed by 4-nitrobenzylamine hydrochloride (2.3 g, 12.6 mmol) and triethylamine (4.8 mL, 34.5 mmol) as for general procedure A. The crude product was recrystallised in the minimum amount of boiling ethyl acetate to give 3-(4-chlorophenyl)-3-hydroxy-2-(4-nitrobenzyl)-2,3-dihydroisoindol-1-one as a light yellow solid (2.95 g, 7.47 mmol, 65%); R$_f$=0.4 (40:60:EtOAc:petrol). 197.1-199.7° C. λ$_{max}$ (CH$_3$OH)/nm 220, Abs 0.765. IR: 3215, 1676, 1517, 1395, 1341 cm$^{-1}$. $^1$H NMR: (300 MHz, d$_6$-DMSO) δ 4.35 (d, 1H, J=16.3 Hz, N—CH$_2$), 4.61 (d, 1H, J=16.3 Hz, N—CH$_2$), 7.28 (m, 4H, Ar—H), 7.45 (m, 3H, Ar—H), 7.58 (m, 2H, Ar—H), 7.79 (m, 1H, Ar—H), 8.05 (m, 2H, Ar—H). $^{13}$C NMR: (75 MHz, d$_6$-DMSO) δ 42.1, 90.5, 123.1, 123.3, 128.4, 128.7, 129.1, 129.9, 130.3, 133.2, 133.3, 138.9, 146.4, 146.5, 149.4, 167.1. LC/MS-ES+ m/z 307.2, 368.2, 377.1. Anal. Calcd. for $C_{21}H_{15}CN_2O_4$: C, 63.89; H, 3.83; N, 7.10%. Found C, 63.78; H, 3.92; N, 7.12%. HRMS (EI) m/z Calcd. for $C_{21}H_{15}ClN_2O_4$: 394.0720. Found 394.0714.

General Procedure L: 3-Amino-2-cyclohexylmethyl-3-(4-methanesulphanylphenyl)isoindolinone, gave a white powder (112 mg, 87%). Mpt 195-199° C., $^1$H-NMR: $\delta_H$ (300 MHz, CDCl$_3$): 0.89 (4H, m, 2×CH$_2$); 1.49 (6H, m, CH$_2$); 1.74 (1H, m, CH$_2$); 1.47 (1H, m, NCH$_2$); 2.40 (1H, m, NCH$_2$); 3.51 (1H, m, NCH$_2$); 6.81 (1H, s, NH); 7.19 (5H, m, ArH); 7.40 (5H, m, ArH); 7.71 (2H, m, ArH); 7.80 (1H, m, ArH). $^{13}$C-NMR: $\delta_C$ (125 MHz, CDCl$_3$): 15.6, 26.1, 26.5, 31.3, 31.5, 37.9, 47.0, 79.7, 122.5, 123.9, 126.1, 127.1, 127.2, 129.0, 130.7, 132.4, 132.5, 135.2, 140.1, 147.9, 166.7, 169.2. Anal. Calcd. for $C_{29}H_{30}N_2O_2S$. 0.2H$_2$O: C, 73.45; H, 6.46; N, 5.91. Found: C, 73.48; H, 6.52; N, 5.81.

Compounds NU8001, NU8006 and NU8009 were prepared using method A as referred to herein.

The present invention will now be described by way of example only and with reference to the following drawing in which:

FIG. 1 shows a Western blot from SJSA cells treated with a compound of the present invention.

A potent compound from the series NU8231 (IC$_{50}$=5.3±0 μM) was selected for further evaluation. SJSA cells (MDM2 amplified) were treated with increasing concentrations of NU8231 (5, 10 and 20 μM). Cells were lysed at 6 hours and Western blots run, probing for p53, p21 and actin. The blot clearly shows a dose dependent increase in MDM2 and p21, consistent with p53 activation. No change was observed for p53 levels or the actin controls.

It is of course to be understood that the invention is not intended to be restricted to the details of the above embodiments which is described by way of example only.

REFERENCES

1. Lane, D. P. *Nature* 1992, 358, 15-16.
2. Vousden, K. H.; Lu, X. *Nat. Rev. Cancer* 2002, 2, 594-604.
3. Momand, J.; Zambetti, G. P.; Olson, D. C.; George, D.; Levine, A. *Cell* 1992, 69, 1237-1245.
4. Fuchs, S. Y.; Adler, V.; Buschmann, T.; Wu, X. W.; Ronai, Z. *Oncogene* 1998, 17, 2543-2547.
5. Oliner, J. D.; Kinzler, K. W.; Meltzer, P. S.; George, D. L.; Vogelstein, B. *Nature* 1992, 358, 80-83.
6. Kussie, P. H.; Gorina, S.; Marechal, V.; Elenbaas, B.; Moreau, J.; Levine, A. J.; Pavletich, N. P. *Science* 1996, 274, 948-953.
7. Chene, P. *Nat. Rev. Cancer* 2003, 3, 102-109.
8. Chene, P.; Fuchs, J.; Bohn, J.; Garcia-Echeverria, C.; Furet, P.; Fabbro, D. *J. Molec. Biol.* 2000, 299, 245-253.
9. Duncan, S. J.; Gruschow, S.; Williams, D. H.; McNicolas, C.; Purewal, R.; Hajek, M.; Gerlitz, M.; Martin, S.; Wrigley, S. K.; Moore, M. *J. Am. Chem. Soc.* 2001, 123, 554-560.
10. Zhao, J. H.; Wang, M. J.; Chen, J.; Luo, A. P.; Wang, X. Q.; Wu, M.; Yin, D. L.; Liu, Z. H. *Cancer Lett* 2002, 183, 69-77.
11. Vassilev, L. T.; Vu, B. T.; Graves, B.; Carvajal, D.; Podlaski, F.; Filipovic, Z.; Kong, N.; Kammlott, U.; Lukacs, C.; Klein, C.; Fotouhi, N.; Liu, E. A. *Science* 2004, 303, 844-848.

The invention claimed is:

1. A compound of formula 1:

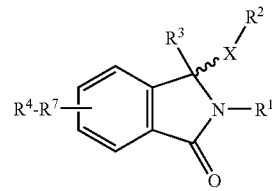

and/or a pharmaceutically acceptable salt thereof, wherein X is O;
R1 is selected from substituted or unsubstituted alkyl, substituted aryl or heteroaryl, unsubstituted heteroaryl and substituted or unsubstituted aralkyl or heteroaralkyl;
R2 is selected from substituted or unsubstituted alkyl, substituted or unsubstituted hydroxyalkyl and substituted or unsubstituted aralkyl or heteroalkyl;
R3 is selected from substituted or unsubstituted aryl; and
R4-R7, is used to represent groups R4, R5, R6 and R7 which are independently selected from H, OH, alkyl, alkoxy, hydroxyalkyl, halo, CF3, NH2, NO2, COOH,
wherein, when R1 is a substituted or an unsubstituted alkyl group having 1 to 6 carbon atoms, R2 is not an unsubstituted alkyl group having 1 to 6 carbon atoms; and
wherein when R1 is a substituted or unsubstituted benzyl or substituted aryl, R2 is not methoxybenzyl or an unsubstituted alkyl group having 1 to 6 carbon atoms.

2. A compound according to claim 1, wherein R1 is a substituted or unsubstituted alkyl group or a substituted aryl group; R2 is hydroxyalkyl, or a substituted or unsubstituted heteroaralkyl group; R3 is a substituted or unsubstituted aryl group; and R4, R5 and R6 are hydrogen atoms.

3. A compound according to claim 1, wherein R1 is selected from an alkyl group having 1 to 4 carbon atoms, a phenyl group or an alkyl group substituted with an acetamide functional group.

4. A compound according to claim 1, wherein R2 is a substituted or unsubstituted alkyl group.

5. A compound according to claim 4, wherein R2 is a substituted alkyl group.

6. A compound according to claim 1, wherein R3 is a substituted or unsubstituted aryl group selected from phenyl, 4-chlorophenyl or silylethoxymethoxyphenyl.

7. A compound of claim 1, wherein said compound inhibits the interaction of MDM2 protein with p53.

8. A medicament comprising a compound according to claim 1.

9. A pharmaceutical composition comprising an effective amount of at least one compound of claim 1.

* * * * *